US006924365B1

(12) United States Patent  (10) Patent No.: US 6,924,365 B1
Miller et al.  (45) Date of Patent: Aug. 2, 2005

(54) OPTIMIZED MESSENGER RNA

(75) Inventors: Allan M. Miller, Boxford, MA (US); Douglas A. Treco, Arlington, MA (US); Richard F Selden, Wellesley, MA (US)

(73) Assignee: Transkaryotic Therapies, Inc., Cambridge, MA (US)

( * ) Notice: Subject to any disclaimer, the term of this patent is extended or adjusted under 35 U.S.C. 154(b) by 0 days.

(21) Appl. No.: 09/407,605

(22) Filed: Sep. 28, 1999

Related U.S. Application Data

(60) Provisional application No. 60/130,241, filed on Apr. 20, 1999, and provisional application No. 60/102,239, filed on Sep. 29, 1998.

(51) Int. Cl.$^7$ .......................... C07H 21/04; C12N 15/00
(52) U.S. Cl. .................. 536/23.1; 435/69.1; 435/320.1; 435/325; 530/350; 530/381
(58) Field of Search ............................... 536/23.1, 23.5; 530/350, 381; 435/69.1, 320.1, 325

(56) References Cited

U.S. PATENT DOCUMENTS

| 4,965,199 A | | 10/1990 | Capon et al. ............... 435/69.6 |
| 5,786,464 A | | 7/1998 | Seed .......................... 536/23.5 |
| 5,795,737 A | | 8/1998 | Seed et al. .................. 435/69.1 |
| 6,034,072 A | * | 3/2000 | Ralston et al. ................. 514/44 |

FOREIGN PATENT DOCUMENTS

| WO | 96/09378 A1 | 3/1996 |
| WO | WO 96/09378 | 3/1996 |
| WO | WO 97/11086 | 3/1997 |
| WO | WO 97/26333 | 7/1997 |
| WO | WO 97/31115 | 8/1997 |
| WO | WO 97/47358 | 12/1997 |
| WO | WO 97/48370 | 12/1997 |
| WO | WO 98/12207 | 3/1998 |
| WO | 98/12207 A1 | 3/1998 |
| WO | WO 98/24922 | * 6/1998 |

OTHER PUBLICATIONS

Grantham et al., Nucleic Acid Research vol. 9, No. 1,(1981) r43–r74.*
Peter Lind et al.. "Novel forms of B–domain–deleted recombinant factor VIII molecules Construction and biochemical characterization", *European Journal of Biochemistry*, vol. 232, No. 1, pp. 19–27 (Aug. 15, 1995).
Carmel M. Lynch et al, "Sequences in the Coding Region of Clotting Factor VIII Act as Dominant Inhibitors of RNA Accumulation and Protein Production", *Human Gene Therapy*, vol. 4, No. 3, pp. 259–272 (Jun. 1, 1993).
Louise C. Wasley et al., "PACE Furin Can Process the Vitamin K–dependent Pro–factor IX Precursor within the Secretory Pathway", *Journal of Biological Chemistry*, vol. 268, No. 12, pp. 8458–8465 (Apr. 25, 1993).
Chiu et al., "Engineered GFP as a vital reporter in plants", *Current Biology*, vol. 6, No. 3, pp 325–330 (1996).

D'Onofrio et al., "Correlations between the Compositional Properties of Human Genes, Codon Usage, and Amino Acid Composition of Proteins", *Journal of Molecular Evolution*, vol. 32, No. 6, pp 504–510 (1991).
Eyre–Walker, "An Analysis of Codon Usage in Mammals: Selection or Mutation Bias?", *Journal of Molecular Evolution*, vol. 33, No. 5, pp 442–449 (1991).
Haas et al., "Codon usage limitation in the expression of HIV–1 envelope glycoprotein", *Current Biology*, vol. 6, No. 3, pp 315–324 (1996).
Hannig et al., "Strategies for optimizing heterologous protein expression in *Escherichia coli*"; *TIBTECH*, vol. 16, pp 54–60 (1998).
Herrick et al., "Identification and Comparison of Stable and Unstable MRNAs in *Saccharomyces cerevisiae*", *Molecular and Cellular Biology*, vol. 10, No. 5, pp 2269–2284 (1990).
Herrick et al., "The Half–Life of c–*myc* mRNA in Growing and Serum–Stimulated Cells: Influence of the Coding and 3' Untranslated Regions and Role of Ribosome Translocation", *Molecular and Cellular Biology*, vol. 14, No. 3, pp 2119–2128 (1994).
Hoekema et al., "Codon Replacement in the *PGK1* Gene of *Saccharomyces cerevisiae*: Experimental Approach To Study the Role of Biased Codon Usage in Gene Expression", *Molecular and Cellular Biology*, vol. 7, No. 8, pp 2914–2924 (1987).
Hubatsch et al., "Human glutathione transferase A4–4: an Alpha class Enzyme with high catalytic efficiency in the conjunction of 4–hydroxynonenal and other genotoxic products of lipid peroxidation"; *Biochem. J.*, 330, pp 175–179 (1998).
Kim et al., "Codon optimization for high–level expression of human erythropoietin (EPO) in mammalian cells"; *GENE*, pp 293–301 (1997).
Kurland, "Codon bias and gene expression", *FEBS Letters*, vol. 285, No. 2, pp 165–169 (1991).
Mehta et al., "Optimization Gene Synthesis, High Level Expression, Isotopic Enrichment, and Refolding of Human Interleukin–5"; *Protein Expression and Purification*, 11, pp 86–94 (1997).
Parker et al., "Translation and a 42–nucleotide segment within the coding region of the mRNA encoded by the *MATα1* gene are involved in promoting rapid mRNA decay in yeast", *Proc. Natl. Acad. Sci.* vol. 87, No. 7, pp 2780–2784 (1990).
Solomovici et al., "Does *Escherichia coli* Optimize the Economics of the Translation Process?"; *J. theor. Biol.*, 185, pp 511–521 (1997).

(Continued)

*Primary Examiner*—Jon Weber
*Assistant Examiner*—Chih–Min Kam
(74) *Attorney, Agent, or Firm*—Fish & Richardson P.C.

(57) ABSTRACT

The present invention is directed to a synthetic nucleic acid sequence which encodes a protein wherein at least one non-common codon or less-common codon is replaced by a common codon. The synthetic nucleic acid sequence can include a continuous stretch of at least 90 codons all of which are common codons.

30 Claims, 33 Drawing Sheets

OTHER PUBLICATIONS

Wright, "The 'Effective number of codons' used in a gene", *Gene*, vol. 87, No. 1, pp 23–29 (1990).

Yang et al., "Optimized codon usage and chromophore mutations provide enhanced sensitivity with the green fluorescent protein", *Nucleic Acids Research*, vol. 24, No. 22, pp 4592–4593 (1996).

Zhang et al., "An Enhanced Green Fluorescent Protein Allows Sensitive Detection of Gene Transfer in Mammalian Cells", *Biochemical and Biophysical Research Communications*, vol. 227, No. 3, pp 707–711 (1996).

Zhang et al., "Graphic Analysis of Codon Usage Strategy in 1490 Human Proteins", *Journal of Protein Chemistry*, vol. 12, No. 3, pp 329–335 (1993).

Andre et al., "Increased Immune Response Elicited by DNA Vaccination with a Synthetic gp120 Sequence with Optimized Codon Usage"; *Journal of Virology*, vol. 72, No. 2, pp 1497–1503 (1998).

Berg et al., "Growth Rate–optimized tRNA Abundance and Codon Usage"; *J. Mol. Biol.*, pp 544–550 (1997).

Billinton, et al., "Development of a green fluorescent protein reporter for a yeast genotoxicity biosensor"; *Biosensors& Bioelectronics* 13 pp 831–838 (1998).

* cited by examiner

Fragment A

```
EcoRI    NheI                                      AM1 Af1
GTAGAATTCGTAGGCTAGCATGCAGATGAGCTGAGCACCTGCTTCTTCCTGTGCCTGCTGCGCTTCTGC
CATCTTAAGCATCCGATCGTACGTCTGACTCGACTCGTGGACGAAGAAGGACACGGACGACGCGAAGACG
                                  AM1 Ar3
                                           3' OH 5' P

TTCAGCGCCACCCG TCGCTACTACCTGGGCGCCGTGAGCTGG GACTACATGCAGAGCGACCT
AAGTCGCGGTGGGC GGCGATGATGGACCCGCGGCACTCGACC CTGATGTACGTCTCGCTGGA
              5' P 3' OH    AM1 Af2                    AM1 Ar2

GGGCGAGCTGCCCGTGGACGCCCCGCTTCCCCCCCCGTGCCCAAGAGCTTCC TCTTCAACACCAGCGT
CCCGCTCGACGGGCACCTGCGGGGCGAAGGGGGGGGCACGGGTTCTCGAAGG GGAAGTTGTGGTCGCA
                                                5' P 3' OH
                3' OH 5' P             AM1 Af3

GGTGTACAAGAAGAC CCTGTTCGTGGAGTTCACCGACCACCTGTTCAACATCGCCAAGCCCCGCCCCCC
CCACATGTTCTTCTG GGACAAGCACCTCAAGTGGCTGGTGGACAAGTTGTAGCGGTTCGGGCGGGGGGG
                                AM1 Ar1

ApaI    HindIII
CTGGATGGGCCTGCTGGCCCC TACAAGCTTTAC
GACCTACCCGGACGACCGGGG ATGTTCGAAATG
```

FIG. 5A

Fragment B

```
EcoRI    ApaI                                                              AM1 Bf1
GTAGAATTCGTAGGGCCCCACCATCCAGGCCGAGGTGTACGACACCGTGGTGATCACCCTGAAGAACATGGCCAG
CATCTTAAGCATCCCCGGGGTGTAGGTCCGGCTCCACATGCTGTGGCACCACTAGTGGGACTTCTTGTACCGGTC
                                AM1 Br3                      3' OH 5' P
                                                                |
CCACCCCGTGAGC  TGCACGCCCGTGGGCTGAGCTACTG  GAAGGCCAGCGAGGGCCGAGTACGACGACCAGA
GGTGGGGCACTCG  GACGTGCGGGCACCCGACTCGATGAC CTTCCGGTCGCTCCCGGCTCATGCTGCTGGTCT
           5' P 3' OH            AM1 Bf2                     AM1 Br2
                                                                      3' OH 5' P
                                                                            |
CCAGCCAGCCAGCGAGAAGGAAGGAGACAAGGTGTTCCCCGG  GGCCAGCAGCCACACTGTGGCAGGTG CTGAAG
GGTCGGTCGGTCGCTCTTCCTTCCTCTGTTCCACAAGGGGCC  GCCGTCGTCGGTGTGACACCGTCCAC GACTTC
              AM1 Bf3                     5' P 3' OH                PmlI  HindIII
GAGAACGGCCCCATGGCCAGCGACCCCCTGCCTGACCTACAGCTACCTGAGCCACGTGCTACAAGCTTTAC
CTCTTGCCGGGGTACCGGTCGCTGGGGGACGGACTGGATGTCGATGGACTCGGTGCACGATGTTCGAAATG
              AM1 Br1
```

FIG. 5B

Fragment C

EcoRI    PmlI                                                                    AM1Cf1
GTAGAATTCGTAGCCACGTGGACCTGGTGAAGACCTGAAGGACCTGGTGAAGGACCTGGTGCCGCGAGGGCAGCCTG
CATCTTAAGCATCGGTGCACCTGGACCACTTCCTGGACTTCCTGGACCACGGCGACCACACGGCGCTCCGTCGGAC
                                            3' OH 5' P                     AM1Cf3                                  AM1Cf2
GCCAAGGAGAAGAC CCAGACCCTGCACAAGTTCATC CTGCTGTTCGCCGTGTTCGACGAGGGCAAGAGCTGGCACAGCGAGACC
CGGTTCCTCTTCTG GGTCTGGGACGTGTTCAAGTAG GACGACAAGCGGCACAAGCTGCTCCCGTTCTCGACCGTGTCGCTCTGG
                 5' P 3' OH                                                            AM1Cr3
                                                                                                      3' OH 5' P                                AM1Cr2
AAGAACAGCCTGATGCAGGACCGCGAGCGCCAGCGCC TGCGCCTGGCCCAAGATGCACAC CGTGAACGGCTACGTGAACCGC
TTCTTGTCGGACTACGTCCTGGCGCTCGCGGTCGCGG CGCGGACCGGGTTCTACGTGTG GCACTTGCCGATGCACTTGGCG
                                                       5' P 3' OH
                                           PmlI            HindIII
AM1Cf3                                                       PmlI            HindIII
AGCCTGCCCGGCCTGATCGGCTGCCACCGCAAGAGCGTGTACTGGCACGTGCTACAAGCTTTAC
TCGGACGGGCCGGACTAGCCGACGGTGGCGTTCTCGCACATGACCGTGCACGATGTTCGAAATG
AM1Cr1

FIG. 5C

Fragment D

```
     EcoRI    PmlI                                                        AM1Df1
GTAGAATTCGTAGACGTGATGGCATGGGCCACCACCCCGAGGTGCACAGCATCTTCCTGGAGGCCCACAC CTTCCTGGTGCGCAACCACCG
CATCTTAAGCATCTGCACTAGCCGTACCCGTGGGGGCTCCACGTGTCGTAGAAGGACCTCCCGGTGT GAAGGACCACGCGTTGGTGGC
                                            AM1Dr4                         5'P 3'OH
3'OH 5'P                                                    AM1Df2
CCAGGC CAGCCCTGGAGATCAGCCCCATCACCTTCCTGACCGGCCTGGGCTGTGATGGACCTGGGACCCGGTCAAGGACGACAA GACGGTGAGT
GGTCCG GTCGGGACCTCTAGTCGGGGTAGTGGAAGGACTGGCCGGACCCGACACTACCTGGACCCTGGGCCAGTTCCTGCTGTT CTGCCACATCA
                                            AM1Df3                                  5'P 3'OH
       3'OH 5'P
         |  |
GCAGCCACCAGCAC GACGGCATGGAGGCCTACGTGAAGGTGGACAGCTGCCCCGAGGAGCCCAGTCGCCGCATGAAGAAGAACAACGAGGAGG CC
CGTCGGTGGTCGTG CTGCCGTACCTCCGGATGCACTTCCACCTGTCGACGGGGCTCCTCGGGTCAGCGGCGTACTTCTTCTTGTTGCTCCTCC GG
                                      AM1Dr3
                3'OH 5'P                               AM1Dr2                              5'P 3'OH
                  |  |                                                  AM1Df4   BglII               BamHI
GAGGACTACGACGACCTGAC CGACAGCGAGATGGACGTGGCGCTTCGACGACGACAACAGCCCCAGCTTCATCCAGATCTCTACGGAT
CTCCTGATGCTGCTGGACTG GCTGTCGCTCTACCTGCACCACGCGAAGCTGCTGCTGTTGTCGGGGTCGAAGTAGGTCTAGAGATGCCTA
                                                        AM1Dr1

HindIII
CCTACAAGCTTTAC
GGATGTTCGAAATG
```

FIG. 5D

Fragment F

```
         HindIII       KpnI                                        AM1 Fr1
         GTAAAGCTTGTGTAGGGTACCAGCTGCGGTTCTCGTCGGATCACGTTGC  GCTTGTCGCTCATGATCTGGTTGCC
         CATTTCGAACATCCCATGGTCGACGCCAAGAGCAGCTTGTGCGACTTGTCCTAGTCAACG  CGAACAGCGAGTACTAGACCAACGG
                                                AM1 Fr3                    5' P  3' OH
                                                                AM1 Fr2
    3' OH 5' P
         G   CGCTGGTCCACGCTCTCCTTGTAGCAGATCAGGCGGGGCCGATCAGGCCGCTGGCGACCGGTGCCAGCAGTGGCCAGTGTCAG  GAAGCTG
         C  GCGACCAGGTGCGAGAGGAACATCGTCTAGTCCGTCCCCGGCTAGTCCGGCGACCGCTGGCCACGGTCGTCACCGGTCACAGTG  CTTCGAC
                                     AM1 Fr2                                   5' P  3' OH 3' OH 5' P       AM1 Fr3                           BglII
                         GCAGCGGGGGTCGCTCTTGTGTGGGCCGTCCTCCACGTCACGTCCACTTGTACTTGAAGATCTCTAC
         CTGTAGTAGCGGGTCAG   CGTCGCCCCCAGCGAGAACCACCCGGCAGGAGGTGCCAGTGCCAGTGAACATGAACTTCTAGAGATG
                                             AM1 Fr1

EcoRI
         GAATTCTCTAC
         CTTAAGATG
```

FIG. 5F

Fragment H

```
         EcoRI    BamHI                                        AM1Hf1
      GTAGAATTCGTAGGATCCTGGGCTGCCACAACAGCGACTTCCGCCACAACAGCGGACTTGAGCAGCTG TGACAAGAACACCGGCGAC
      CATCTTAAGCATCCTAGGACCCGACGGTGTTGTCGCTGAAGGCGTTGCGCCTGACTTCCACTCGTCGAC GCTGTTCTTGTGGCCGCTG
                                                AM1Hr4                              5' P 3' OH
        3' OH 5' P
         ⎯ ⎯                                         AM1Hf2
      TACTACGAG GACAGCTACGAGGACATCAGCGGCCTACCTGCTGAGGAGGAGATCACCCGACC ACCCTGCAGAG
      ATGATGCTC CTGTCGATGCTCCTGTAGTCGCCGGATGGACGACTCGTCGTTGTGCCGTAGCTCGGGGACCTCCTAGTGGGCGTG GTGGGACGTCTC
                                                  AM1Hr3                                           5' P 3' OH
        3' OH 5' P                                           AM1Hf3
         ⎯ ⎯
      CGACCAGGAG GAGATGACTACGACGACTACAGCGTGGAGATGAAGAAGGAGACTTCGACATCTACGACGAGACGAGAACCAGAGCCC CCGCAGCT
      GCTGGTCCTC CTCTAGCTGATGCTGCTGATGTCGCACCTCTACTTCTTCCTCTGAAGCTGTAGATGCTGCTGCTCTTGGTCTCGGG GGCGTCGA
                     AM1Hr2                                                                  5' P 3' OH
        3' OH 5' P                     AM1Hf4                 PmlI              HindIII
         ⎯ ⎯
      TCCAGAAGAAGACC CGCCACTACTTCATCGCCGCCTGTGGAGCGCCTGGGACTACGGCATGAGCAGCAGCCCCCACGTGCTACAAGCTTTAC
      AGGTCTTCTTCTGG GCGGTGATGAAGTAGCGGCGGACACCCTCGCGGACACCCTGATGCCGTACTCGTCGTCGGGGGTGCACGATGTTCGAAATG
                                                       AM1Hr1
```

FIG. 5H

Fragment I

```
EcoRI      PmlI                                              AM1lf1
GTAGAATTCGTAGCACGTGCTGCGCAACCGCGCCCAGAGCGCGGCAGCGGTGCCCCAGTTCAAGAAGGTGGTGTTCCAGGAGTTCACCGACGGCAG CTTCACCCAG
CATCTTAAGCATCGTGCACGACGCGTTGGCGCGGTCTCGCCCGTCGCCGTTGCCGCCGGGTCAAGTTCTTCCACCAGAAGGTCCTCAAGTGGCTGCCGTC GAAGTGGGTC
                                                                 AM1lr4                             5' P  3' OH

ApaI              AM1lf2                        BstEII
               3' OH 5' P
CCCCTGTACCGC GGCGAGCTGAACGAGCTGGGCCTGCTGGGCCTGGGCCCCTACATCCGCGCCGAGGTGAGGACACACATCATGGTGACCGTGCAGGAGTTCG CC
GGGGACATGGCG CCGCTCGACTTGCTCGTGGACCCGGACGACCCGGGATGTAGGCGCGGCTCCACTCCTGTGTAGTAGTACCACTGGCACGTCTCCAAGC GG
                                                           AM1lr3                                  5' P  3' OH

3' OH 5' P
CTGTTCTTCACCATCTTCGAC GAGACCAAGAGCTGGTACTTCACCGAGAACATGAGCGCAACATCAGATGGAGGACC CCACC
GACAAGAAGTGGTAGAAGCTG CTCTGGTTCTCGACCATGAAGTGGCTCTTGTACCTCGGTTGTAGTTCTACCTCCTGG GGTGG
                           AM1lr2                                               5' P  3' OH

3' OH 5' P                                                      AM1lf4            KpnI     HindIII
TTCAAGGAGAACTACCGCTTCCACG CCATCAACGGCTACAATCATGGACACCCCTGCCCGGCCTGGTGATGGCCAGGACCAGCGCATCCGCTGGTACCCTACAA
AAGTTCCTCTTGATGGCGAAGGTGC GGTAGTTGCCGATGTTAGTACCTGTGGGGACGGGCCGGACCACTACCGGTCCTGGTCGCGTAGGCACCATGGGATGTT
                                     AM1lr1

GCTTTTAC
CGAAAATG
```

FIG. 5I

Fragment J

```
         EcoRI      BstEII              AM1Jf1
         GTAGAATTCGTAGGGTGACCTTCCGCAACCAGCCAGCCGCCCCTACAGCTTCTACAGCCTACGAGAGGAGGACCAGCGCC
         CATCTTAAGCATCCCACTGGAAGGCGTTGGTCCGGTCGGCGGGGATGTCGGACTAGTCGATGCTCCTCCTGGTCGCGG
                                                              AM1Jr3                              AM1Jf2
                                                       3' OH 5' P
         AGG TGCGCCGAGCCCCGCAAGAACTTC GTGAAGCCCAAGAGACCAAGACCTACTTCTGGAAGGTGCAGCACCACATGGCCCCACCAA
         TCC CGCGGCTCGGGGCGTTCTTGAAG CACTTCGGGTTCTCTGGTTCTGGATGAAGACCTTCCACGTGGTGTACCGGGGTGGTT
         5' P 3' OH                                                         AM1Jr2
                                                                       3' OH 5' P
         GGACGAGTTCGACTGCAAGGCCTACTTCAG CGACGTGAGAAGGAC GTGCACAGCGGCCTGATCGGCCCCTGCTG
         CCTGCTCAAGCTGACGTTCCGGATGAAGTC GCTGCACCTGGACCTTCCTG CACGTGCCCGGACTAGCCGGGGACGAC
                                      5' P 3' OH
                      AM1Jf3           Eagl       BstEII    HindIII
         GGACGAGTTCGACTGCAAGGCCTACTTCAGCGACGTGAGAAGGACGTGCACAGCGGCCTGATCGGCCCCTGCTG
         CCTGCTCAAGCTGACGTTCCGGATGAAGTCGCTGCACCTGGACCTTCCTGCACGTGCCCGGACTAGCCGGGGACGAC
                 AM1Jr1
```

FIG. 5J

Fragment K

EcoRI   KpnI          AM1Kf1        PmlI
GTAGAATTCGTAGGGTACCTGCTGAGCATGGGCAGCAACGAGAACATCCACAGCATCCACTTCAGCGGCCACGTGTTCACCGTGCCAAGAA
CATCTTAAGCATCCCATGGACGACTCGTACCCGGTCGTTGCTCTCTTGTAGGTGTCGTAGGTGAAGTCGCCGGTGCACAAGTGGCACGCGTTCTT
                                        AM1Kr3                                AM1Kf2
                    3' OH 5' P
GGAG⌐GAGTACAAGATGGCCCTGTACAAC⌐CTGTACCCCGGCGTGTTCGAGACCGTGGAGATGCTGCCAGCAAGGCCCGGCATCTGGCGCGT
CCTC CTCATGTTCTACCGGGACATGTTG_GACATGGGGCCGCACAAGCTCTGGCACCTGGCACCTCTACGACGGTCGTTCCGGCCGTAGACCGCGCA
5' P 3' OH                                                                      AM1Kr2
                                                        3' OH 5' P
GGAGTGCCTGATCGGCGAGCACCTGCAGCGCCGGCATGAG⌐CACCCTGTTCCTGGTTGTACAG⌐CAACAAGTGCCAGACCCCCCTGGGCATGGC
CCTCACGGACTAGCCGCTCGTGGACGTCGCGGCCGTACTC GTGGGACAAGGACCACATGTC_GTTGTTCACGGTCTGGGGGACCCGTACCG
                                        5' P 3' OH
           AM1Kf3                      ApaI    HindIII
CAGCGGCCACATCCGGACTTCCAGATCACCGCGCCAGCGGCCAGTACGGCCAGTGGCCCCTACAAGCTTTAC
GTCGCCGGTGTAGGCGCTGAAGGTCTAGTGGCGCGGTCGCCGGTCATGCCGGTCACCCGGGGATGTTCGAAATG
           AM1Kr1

FIG. 5K

Fragment M

```
     EcoRI    EcoRV                              AM1Mf1
GTAGAATTCGTAGGATATCATCGCCCGCTACATCCGCCTGCACCCCACTACAGCATCCGCAGCACCCTGCGCATGGAGCTGATGGG
CATCTTAAGCATCCTATAGTAGCGGGCGATGTAGGCGGACGTGGGGTGATGTCGTAGGCGTCGTGGGACGCGTACCTCGACTACCC
                                              AM1Mr3                              AM1Mf2

3'OH 5'P
CTGCGAC  CTGAACAGCTGCAGCATGCCCCTGG   GCATGGAGAGCAAGGCCATCAGCGACGCCCAGATCACCGCCAGCTACTTCACC
GACGCTG  GACTTGTCGACGTCGTACGGGGACC  CGTACCTCTCGTTCCGGTAGTCGCTGCGGGTCTAGTGGCGGTCGTCGATGAAGTGG
        5'P 3'OH                                                           AM1Mr2

3'OH 5'P
AACATGTTCGCCACCTGGAGCCCAGCAAGGCC CGCCTGCACCTGCAGGGCCGCAG  CAACGCCTGGCGCCCCCAGTGAACAACCCA
TTGTACAAGCGGTGGACCTCGGGTCGTTCCGG  GCGGACGTGGACGTCCCGGCGTC GTTGCGGACCGCGGGGGTCACTTGTTGGGT
                                   5'P 3'OH

AM1Mf3                    BstEII        HindIII
AGGAGTGGCTGCAGGTGGACTTCCAGAGAGACCATGAAGGTGACCCTACAAGCTTTAC
TCCTCACCGACGTCCACCTGAAGGTCTTCTGGTACTTCCACTGGGATGTTCGAAATG
    AM1Mr1
```

FIG. 5M

Fragment N

```
EcoRI     BstEII                          AM1Nf1
GTAGAATTCGTAGGGTGACCGGCGTGACCACCCAGGGCGTGAAGAGCTGCTGACGTACGTGAAGGAGTTCCTGATCAGCAGCAGCCAGGACGG TCCA
CATCTTAAGCATCCCACTGGCCGCACTGGTGGGTCCCGCACTTCTCGACGACTGGTCGTACATGCACTTCCTCAAGGACTAGTCGTCGGTCCTGCC GGT
                                                                                           5' P 3' OH
                3' OH 5' P                                    AM1Nf2
                  -|                                            -|
           CAGTGGACCCTGTTCTTC CAGAACGGCAAGGTGAAGGTGTTCCAGGACAGCTTCACCCCCGTGGTGAACAGCCTGACCCCCCCCTG CTGAC
           GTCACCCTGGGACAAGAAG_GTCTTGCCGTTCCACTTCCACAAGGTCCCTGTCGAAGTGGGGCACCACTTGTCGGACCTGGGGGGGAC GACTG
                        AM1Nr3                                                 AM1Nr2                 5' P 3' OH

3' OH 5' P                AM1Nf3                  SmaI
                    -|
             CCGCTACCTGCGCATCCACCC CCAGAGCTGGGTGCACCAGATGCCCTGGCTGCGGAGGTGCTGGGCTGCGAGCCCAGGACCCTGCAGGACCTGTACTAGCTGCCCGGGCTA
             GGCGATGGACGCGTAGGTGGG_GGTCTCGACCCACGTGGTCTACGGGACCGACGCCTCCACGACCCGACGCTCCGGGTCCTGGACATGATCGACGGGCCCGAT
                                            AM1Nr1

HindIII
CAAGCTTTAC
GTTCGAAATG
```

FIG. 5N

```
        EcoRI        NheI
   1  TAGAATTCGTAGGCTAGCATGCAGATCGAGCTGAGCACCTGCTTCTTCCTGTGCCTGCTGCGCTTCTGCTTC
                   1▶ MetGlnIleGluLeuSerThrCysPhePheLeuCysLeuLeuArgPheCysPhe
  73  AGCGCCACCCGCCGCTACTACCTGGGCGCCGTGGAGCTGAGCTGGGACTACATGCAGAGCGACCTGGGCGAG
  19▶ SerAlaThrArgArgTyrTyrLeuGlyAlaValGluLeuSerTrpAspTyrMetGlnSerAspLeuGlyGlu
 145  CTGCCCGTGGACGCCCGCTTCCCCCCCCGCGTGCCCAAGAGCTTCCCCTTCAACACCAGCGTGGTGTACAAG
  43▶ LeuProValAspAlaArgPheProProArgValProLysSerPheProPheAsnThrSerValValTyrLys
 217  AAGACCCTGTTCGTGGAGTTCACCGACCACCTGTTCAACATCGCCAAGCCCCGCCCCCCCTGGATGGGCCTG
  67▶ LysThrLeuPheValGluPheThrAspHisLeuPheAsnIleAlaLysProArgProProTrpMetGlyLeu
         ApaI                                          MscI
 289  CTGGGCCCCACCATCCAGGCCGAGGTGTACGACACCGTGGTGATCACCCTGAAGAACATGGCCAGCCACCCC
  91▶ LeuGlyProThrIleGlnAlaGluValTyrAspThrValValIleThrLeuLysAsnMetAlaSerHisPro
 361  GTGAGCCTGCACGCCGTGGGCGTGAGCTACTGGAAGGCCAGCGAGGGCGCCGAGTACGACGACCAGACCAGC
 115▶ ValSerLeuHisAlaValGlyValSerTyrTrpLysAlaSerGluGlyAlaGluTyrAspAspGlnThrSer
 433  CAGCGCGAGAAGGAGGACGACAAGGTGTTCCCCGGCGGCAGCCACACCTACGTGTGGCAGGTGCTGAAGGAG
 139▶ GlnArgGluLysGluAspAspLysValPheProGlyGlySerHisThrTyrValTrpGlnValLeuLysGlu
         MscI                                          PmlI
 505  AACGGCCCCATGGCCAGCGACCCCCTGTGCCTGACCTACAGCTACCTGAGCCACGTGGACCTGGTGAAGGAC
 163▶ AsnGlyProMetAlaSerAspProLeuCysLeuThrTyrSerTyrLeuSerHisValAspLeuValLysAsp
                                                             MscI
 577  CTGAACAGCGGCCTGATCGGCGCCCTGCTGGTGTGCCGCGAGGGCAGCCTGGCCAAGGAGAAGACCCAGACC
 187▶ LeuAsnSerGlyLeuIleGlyAlaLeuLeuValCysArgGluGlySerLeuAlaLysGluLysThrGlnThr
 649  CTGCACAAGTTCATCCTGCTGTTCGCCGTGTTCGACGAGGGCAAGAGCTGGCACAGCGAGACCAAGAACAGC
 211▶ LeuHisLysPheIleLeuLeuPheAlaValPheAspGluGlyLysSerTrpHisSerGluThrLysAsnSer
 721  CTGATGCAGGACCGCGACGCCGCCAGCGCCCGCGCCTGGCCCAAGATGCACACCGTGAACGGCTACGTGAAC
 235▶ LeuMetGlnAspArgAspAlaAlaSerAlaArgAlaTrpProLysMetHisThrValAsnGlyTyrValAsn
                                                                  PmlI
 793  CGCAGCCTGCCCGGCCTGATCGGCTGCCACCGCAAGAGCGTGTACTGGCACGTGATCGGCATGGGCACCACC
 259▶ ArgSerLeuProGlyLeuIleGlyCysHisArgLysSerValTyrTrpHisValIleGlyMetGlyThrThr
 865  CCCGAGGTGCACAGCATCTTCCTGGAGGGCCACACCTTCCTGGTGCGCAACCACCGCCAGGCCAGCCTGGAG
 283▶ ProGluValHisSerIlePheLeuGluGlyHisThrPheLeuValArgAsnHisArgGlnAlaSerLeuGlu
 937  ATCAGCCCCATCACCTTCCTGACCGCCCAGACCCTGCTGATGGACCTGGGCCAGTTCCTGCTGTTCTGCCAC
 307▶ IleSerProIleThrPheLeuThrAlaGlnThrLeuLeuMetAspLeuGlyGlnPheLeuLeuPheCysHis
1009  ATCAGCAGCCACCAGCACGACGGCATGGAGGCCTACGTGAAGGTGGACAGCTGCCCCGAGGAGCCCCAGCTG
 331▶ IleSerSerHisGlnHisAspGlyMetGluAlaTyrValLysValAspSerCysProGluGluProGlnLeu
1081  CGCATGAAGAACAACGAGGAGGCCGAGGACTACGACGACGACCTGACCGACAGCGAGATGGACGTGGTGCGC
 355▶ ArgMetLysAsnAsnGluGluAlaGluAspTyrAspAspAspLeuThrAspSerGluMetAspValValArg
                    (BglII/BamHI)
1153  TTCGACGACGACAACAGCCCCAGCTTCATCCAGATCCGCAGCGTGGCCAAGAAGCACCCCAAGACCTGGGTG
 379▶ PheAspAspAspAsnSerProSerPheIleGlnIleArgSerValAlaLysLysHisProLysThrTrpVal
1225  CACTACATCGCCGCCGAGGAGGAGGACTGGGACTACGCCCCCCTGGTGCTGGCCCCCGACGACCGCAGCTAC
 403▶ HisTyrIleAlaAlaGluGluGluAspTrpAspTyrAlaProLeuValLeuAlaProAspAspArgSerTyr
                                                 EagI
1297  AAGAGCCAGTACCTGAACAACGGCCCCCAGCGCATCGGCCGCAAGTACAAGAAGGTGCGCTTCATGGCCTAC
 427▶ LysSerGlnTyrLeuAsnAsnGlyProGlnArgIleGlyArgLysTyrLysLysValArgPheMetAlaTyr
                                                                    ApaI
1369  ACCGACGAGACCTTCAAGACCCGCGAGGCCATCCAGCACGAGAGCGGCATCCTGGGCCCCCTGCTGTACGGC
 451▶ ThrAspGluThrPheLysThrArgGluAlaIleGlnHisGluSerGlyIleLeuGlyProLeuLeuTyrGly
```

FIG. 7A

1441 GAGGTGGGCGACACCCTGCTGATCATCTTCAAGAACCAGGCCAGCCGCCCCTACAACATCTACCCCCACGGC
475▶ GluValGlyAspThrLeuLeuIleIlePheLysAsnGlnAlaSerArgProTyrAsnIleTyrProHisGly
1513 ATCACCGACGTGCGCCCCCTGTACAGCCGCCGCCTGCCCAAGGGCGTGAAGCACCTGAAGGACTTCCCCATC
499▶ IleThrAspValArgProLeuTyrSerArgArgLeuProLysGlyValLysHisLeuLysAspPheProIle
                  BglII
1585 CTGCCCGGCGAGATCTTCAAGTACAAGTGGACCGTGACCGTGGAGGACGGCCCCACCAAGAGCGACCCCCGC
523▶ LeuProGlyGluIlePheLysTyrLysTrpThrValThrValGluAspGlyProThrLysSerAspProArg
1657 TGCCTGACCCGCTACTACAGCAGCTTCGTGAACATGGAGCGCGACCTGGCCAGCGGCCTGATCGGCCCCCTG
547▶ CysLeuThrArgTyrTyrSerSerPheValAsnMetGluArgAspLeuAlaSerGlyLeuIleGlyProLeu
1729 CTGATCTGCTACAAGGAGAGCGTGGACCAGCGCGGCAACCAGATCATGAGCGACAAGCGCAACGTGATCCTG
571▶ LeuIleCysTyrLysGluSerValAspGlnArgGlyAsnGlnIleMetSerAspLysArgAsnValIleLeu
                  KpnI
1801 TTCAGCGTGTTCGACGAGAACCGCAGCTGGTACCTGACCGAGAACATCCAGCGCTTCCTGCCCAACCCCGCC
595▶ PheSerValPheAspGluAsnArgSerTrpTyrLeuThrGluAsnIleGlnArgPheLeuProAsnProAla
1873 GGCGTGCAGCTGGAGGACCCCGAGTTCCAGGCCAGCAACATCATGCACAGCATCAACGGCTACGTGTTCGAC
619▶ GlyValGlnLeuGluAspProGluPheGlnAlaSerAsnIleMetHisSerIleAsnGlyTyrValPheAsp
1945 AGCCTGCAGCTGAGCGTGTGCCTGCACGAGGTGGCCTACTGGTACATCCTGAGCATCGGCGCCCAGACCGAC
643▶ SerLeuGlnLeuSerValCysLeuHisGluValAlaTyrTrpTyrIleLeuSerIleGlyAlaGlnThrAsp
2017 TTCCTGAGCGTGTTCTTCAGCGGCTACACCTTCAAGCACAAGATGGTGTACGAGGACACCCTGACCCTGTTC
667▶ PheLeuSerValPhePheSerGlyTyrThrPheLysHisLysMetValTyrGluAspThrLeuThrLeuPhe
                  BamHI
2089 CCCTTCAGCGGCGAGACCGTGTTCATGAGCATGGAGAACCCCGGCCTGTGGATCCTGGGCTGCCACAACAGC
691▶ ProPheSerGlyGluThrValPheMetSerMetGluAsnProGlyLeuTrpIleLeuGlyCysHisAsnSer
2161 GACTTCCGCAACCGCGGCATGACCGCCCTGCTGAAGGTGAGCAGCTGCGACAAGAACACCGGCGACTACTAC
715▶ AspPheArgAsnArgGlyMetThrAlaLeuLeuLysValSerSerCysAspLysAsnThrGlyAspTyrTyr
2233 GAGGACAGCTACGAGGACATCAGCGCCTACCTGCTGAGCAAGAACAACGCCATCGAGCCCGCCTGGAGGAG
739▶ GluAspSerTyrGluAspIleSerAlaTyrLeuLeuSerLysAsnAsnAlaIleGluProArgLeuGluGlu
                  BstXI
2305 ATCACCCGCACCACCCTGCAGAGCGACCAGGAGGAGATCGACTACGACGACACCATCAGCGTGGAGATGAAG
763▶ IleThrArgThrThrLeuGlnSerAspGlnGluGluIleAspTyrAspAspThrIleSerValGluMetLys
2377 AAGGAGGACTTCGACATCTACGACGAGGACGAGAACCAGAGCCCCCGCAGCTTCCAGAAGAAGACCCGCCAC
787▶ LysGluAspPheAspIleTyrAspGluAspGluAsnGlnSerProArgSerPheGlnLysLysThrArgHis
                  PmlI
2449 TACTTCATCGCCGCCGTGGAGCGCCTGTGGGACTACGGCATGAGCAGCAGCCCCCACGTGCTGCGCAACCGC
811▶ TyrPheIleAlaAlaValGluArgLeuTrpAspTyrGlyMetSerSerSerProHisValLeuArgAsnArg
2521 GCCCAGAGCGGCAGCGTGCCCCAGTTCAAGAAGGTGGTGTTCCAGGAGTTCACCGACGGCAGCTTCACCCAG
835▶ AlaGlnSerGlySerValProGlnPheLysLysValValPheGlnGluPheThrAspGlySerPheThrGln
                  ApaI
2593 CCCCTGTACCGCGGCGAGCTGAACGAGCACCTGGGCCTGCTGGGCCCCTACATCCGCGCCGAGGTGGAGGAC
859▶ ProLeuTyrArgGlyGluLeuAsnGluHisLeuGlyLeuLeuGlyProTyrIleArgAlaGluValGluAsp
                  BstEII
2665 AACATCATGGTGACCTTCCGCAACCAGGCCAGCCGCCCCTACAGCTTCTACAGCAGCCTGATCAGCTACGAG
883▶ AsnIleMetValThrPheArgAsnGlnAlaSerArgProTyrSerPheTyrSerSerLeuIleSerTyrGlu
2737 GAGGACCAGCGCCAGGGCGCCGAGCCCCGCAAGAACTTCGTGAAGCCCAACGAGACCAAGACCTACTTCTGG
907▶ GluAspGlnArgGlnGlyAlaGluProArgLysAsnPheValLysProAsnGluThrLysThrTyrPheTrp
2809 AAGGTGCAGCACCACATGGCCCCCACCAAGGACGAGTTCGACTGCAAGGCCTGGGCCTACTTCAGCGACGTG
931▶ LysValGlnHisHisMetAlaProThrLysAspGluPheAspCysLysAlaTrpAlaTyrPheSerAspVal

FIG. 7B

```
2881 GACCTGGAGAAGGACGTGCACAGCGGCCTGATCGGCCCCCTGCTGGTGTGCCACACCAACACCCTGAACCCC
 955▶ AspLeuGluLysAspValHisSerGlyLeuIleGlyProLeuLeuValCysHisThrAsnThrLeuAsnPro
          EagI       BstEII
2953 GCCCACGGCCGCCAGGTGACCGTGCAGGAGTTCGCCCTGTTCTTCACCATCTTCGACGAGACCAAGAGCTGG
 979▶ AlaHisGlyArgGlnValThrValGlnGluPheAlaLeuPhePheThrIlePheAspGluThrLysSerTrp
3025 TACTTCACCGAGAACATGGAGCGCAACTGCCGCGCCCCCTGCAACATCCAGATGGAGGACCCCACCTTCAAG
1003▶ TyrPheThrGluAsnMetGluArgAsnCysArgAlaProCysAsnIleGlnMetGluAspProThrPheLys
3097 GAGAACTACCGCTTCCACGCCATCAACGGCTACATCATGGACACCCTGCCCGGCCTGGTGATGGCCCAGGAC
1027▶ GluAsnTyrArgPheHisAlaIleAsnGlyTyrIleMetAspThrLeuProGlyLeuValMetAlaGlnAsp
          KpnI                                                      PmlI
3169 CAGCGCATCCGCTGGTACCTGCTGAGCATGGGCAGCAACGAGAACATCCACAGCATCCACTTCAGCGGCCAC
1051▶ GlnArgIleArgTrpTyrLeuLeuSerMetGlySerAsnGluAsnIleHisSerIleHisPheSerGlyHis
3241 GTGTTCACCGTGCGCAAGAAGGAGGAGTACAAGATGGCCCTGTACAACCTGTACCCCGGCGTGTTCGAGACC
1075▶ ValPheThrValArgLysLysGluGluTyrLysMetAlaLeuTyrAsnLeuTyrProGlyValPheGluThr
3313 GTGGAGATGCTGCCCAGCAAGGCCGGCATCTGGCGCGTGGAGTGCCTGATCGGCGAGCACCTGCACGCCGGC
1099▶ ValGluMetLeuProSerLysAlaGlyIleTrpArgValGluCysLeuIleGlyGluHisLeuHisAlaGly
3385 ATGAGCACCCTGTTCCTGGTGTACAGCAACAAGTGCCAGACCCCCCTGGGCATGGCCAGCGGCCACATCCGC
1123▶ MetSerThrLeuPheLeuValTyrSerAsnLysCysGlnThrProLeuGlyMetAlaSerGlyHisIleArg
                                                                        ApaI
3457 GACTTCCAGATCACCGCCAGCGGCCAGTACGGCCAGTGGGCCCCCAAGCTGGCCCGCCTGCACTACAGCGGC
1147▶ AspPheGlnIleThrAlaSerGlyGlnTyrGlyGlnTrpAlaProLysLeuAlaArgLeuHisTyrSerGly
3529 AGCATCAACGCCTGGAGCACCAAGGAGCCCTTCAGCTGGATCAAGGTGGACCTGCTGGCCCCCATGATCATC
1171▶ SerIleAsnAlaTrpSerThrLysGluProPheSerTrpIleLysValAspLeuLeuAlaProMetIleIle
3601 CACGGCATCAAGACCCAGGGCGCCCGCCAGAAGTTCAGCAGCCTGTACATCAGCCAGTTCATCATCATGTAC
1195▶ HisGlyIleLysThrGlnGlyAlaArgGlnLysPheSerSerLeuTyrIleSerGlnPheIleIleMetTyr
3673 AGCCTGGACGGCAAGAAGTGGCAGACCTACCGCGGCAACAGCACCGGCACCCTGATGGTGTTCTTCGGCAAC
1219▶ SerLeuAspGlyLysLysTrpGlnThrTyrArgGlyAsnSerThrGlyThrLeuMetValPhePheGlyAsn
                                        (SmaI/EcoRV)
3745 GTGGACAGCAGCGGCATCAAGCACAACATCTTCAACCCCCCCATCATCGCCCGCTACATCCGCCTGCACCCC
1243▶ ValAspSerSerGlyIleLysHisAsnIlePheAsnProProIleIleAlaArgTyrIleArgLeuHisPro
3817 ACCCACTACAGCATCCGCAGCACCCTGCGCATGGAGCTGATGGGCTGCGACCTGAACAGCTGCAGCATGCCC
1267▶ ThrHisTyrSerIleArgSerThrLeuArgMetGluLeuMetGlyCysAspLeuAsnSerCysSerMetPro
3889 CTGGGCATGGAGAGCAAGGCCATCAGCGACGCCCAGATCACCGCCAGCAGCTACTTCACCAACATGTTCGCC
1291▶ LeuGlyMetGluSerLysAlaIleSerAspAlaGlnIleThrAlaSerSerTyrPheThrAsnMetPheAla
3961 ACCTGGAGCCCCAGCAAGGCCCGCCTGCACCTGCAGGGCCGCAGCAACGCCTGGCGCCCCCAGGTGAACAAC
1315▶ ThrTrpSerProSerLysAlaArgLeuHisLeuGlnGlyArgSerAsnAlaTrpArgProGlnValAsnAsn
                                                                    BstEII
4033 CCCAAGGAGTGGCTGCAGGTGGACTTCCAGAAGACCATGAAGGTGACCGGCGTGACCACCCAGGGCGTGAAG
1339▶ ProLysGluTrpLeuGlnValAspPheGlnLysThrMetLysValThrGlyValThrThrGlnGlyValLys
4105 AGCCTGCTGACCAGCATGTACGTGAAGGAGTTCCTGATCAGCAGCAGCCAGGACGGCCACCAGTGGACCCTG
1363▶ SerLeuLeuThrSerMetTyrValLysGluPheLeuIleSerSerSerGlnAspGlyHisGlnTrpThrLeu
4177 TTCTTCCAGAACGGCAAGGTGAAGGTGTTCCAGGGCAACCAGGACAGCTTCACCCCCGTGGTGAACAGCCTG
1387▶ PhePheGlnAsnGlyLysValLysValPheGlnGlyAsnGlnAspSerPheThrProValValAsnSerLeu
4249 GACCCCCCCCTGCTGACCCGCTACCTGCGCATCCACCCCCAGAGCTGGGTGCACCAGATCGCCCTGCGCATG
1411▶ AspProProLeuLeuThrArgTyrLeuArgIleHisProGlnSerTrpValHisGlnIleAlaLeuArgMet
                                                SmaI           HindIII
4321 GAGGTGCTGGGCTGCGAGGCCCAGGACCTGTACTAGCTGCCCGGGCTACAAGCTTT
1435▶ GluValLeuGlyCysGluAlaGlnAspLeuTyr•••
```

FIG. 7C

```
         EcoRI       NheI
   1  TAGAATTCGTAGGCTAGCATGCAGATCGAGCTGAGCACCTGCTTCTTCCTGTGCCTGCTGCGCTTCTGCTTC
                   1▶ MetGlnIleGluLeuSerThrCysPhePheLeuCysLeuLeuArgPheCysPhe

73  AGCGCCACCCGCCGCTACTACCTGGGCGCCGTGGAGCTGAGCTGGGACTACATGCAGAGCGACCTGGGCGAG
  19▶ SerAlaThrArgArgTyrTyrLeuGlyAlaValGluLeuSerTrpAspTyrMetGlnSerAspLeuGlyGlu

145  CTGCCCGTGGACGCCCGCTTCCCCCCCCGCGTGCCCAAGAGCTTCCCCTTCAACACCAGCGTGGTGTACAAG
  43▶ LeuProValAspAlaArgPheProProArgValProLysSerPheProPheAsnThrSerValValTyrLys

217  AAGACCCTGTTCGTGGAGTTCACCGACCACCTGTTCAACATCGCCAAGCCCCGCCCCCCCTGGATGGGCCTG
  67▶ LysThrLeuPheValGluPheThrAspHisLeuPheAsnIleAlaLysProArgProProTrpMetGlyLeu
         ApaI                                                Mscl
 289  CTGGGCCCCACCATCCAGGCCGAGGTGTACGACACCGTGGTGATCACCCTGAAGAACATGGCCAGCCACCCC
  91▶ LeuGlyProThrIleGlnAlaGluValTyrAspThrValValIleThrLeuLysAsnMetAlaSerHisPro 361  GTGAGCCTGCACGCCGTGGGCGTGAGCTACTGGAAGGCCAGCGAGGGCGCCGAGTACGACGACCAGACCAGC
 115▶ ValSerLeuHisAlaValGlyValSerTyrTrpLysAlaSerGluGlyAlaGluTyrAspAspGlnThrSer 433  CAGCGCGAGAAGGAGGACGACAAGGTGTTCCCCGGCGGCAGCCACACCTACGTGTGGCAGGTGCTGAAGGAG
 139▶ GlnArgGluLysGluAspAspLysValPheProGlyGlySerHisThrTyrValTrpGlnValLeuLysGlu
         Mscl                                         PmlI
 505  AACGGCCCCATGGCCAGCGACCCCCTGTGCCTGACCTACAGCTACCTGAGCCACGTGGACCTGGTGAAGGAC
 163▶ AsnGlyProMetAlaSerAspProLeuCysLeuThrTyrSerTyrLeuSerHisValAspLeuValLysAsp
                                                     Mscl
 577  CTGAACAGCGGCCTGATCGGCGCCCTGCTGGTGTGCCGCGAGGGCAGCCTGGCCAAGGAGAAGACCCAGACC
 187▶ LeuAsnSerGlyLeuIleGlyAlaLeuLeuValCysArgGluGlySerLeuAlaLysGluLysThrGlnThr 649  CTGCACAAGTTCATCCTGCTGTTCGCCGTGTTCGACGAGGGCAAGAGCTGGCACAGCGAGACCAAGAACAGC
 211▶ LeuHisLysPheIleLeuLeuPheAlaValPheAspGluGlyLysSerTrpHisSerGluThrLysAsnSer 721  CTGATGCAGGACCGCGACGCCGCCAGCGCCCGCGCCTGGCCCAAGATGCACACCGTGAACGGCTACGTGAAC
 235▶ LeuMetGlnAspArgAspAlaAlaSerAlaArgAlaTrpProLysMetHisThrValAsnGlyTyrValAsn
                                                                          PmlI
 793  CGCAGCCTGCCCGGCCTGATCGGCTGCCACCGCAAGAGCGTGTACTGGCACGTGATCGGCATGGGCACCACC
 259▶ ArgSerLeuProGlyLeuIleGlyCysHisArgLysSerValTyrTrpHisValIleGlyMetGlyThrThr 865  CCCGAGGTGCACAGCATCTTCCTGGAGGGCCACACCTTCCTGGTGCGCAACCACCGCCAGGCCAGCCTGGAG
 283▶ ProGluValHisSerIlePheLeuGluGlyHisThrPheLeuValArgAsnHisArgGlnAlaSerLeuGlu 937  ATCAGCCCCATCACCTTCCTGACCGCCCAGACCCTGCTGATGGACCTGGGCCAGTTCCTGCTGTTCTGCCAC
 307▶ IleSerProIleThrPheLeuThrAlaGlnThrLeuLeuMetAspLeuGlyGlnPheLeuLeuPheCysHis 1009  ATCAGCAGCCACCAGCACGACGGCATGGAGGCCTACGTGAAGGTGGACAGCTGCCCCGAGGAGCCCCAGCTG
 331▶ IleSerSerHisGlnHisAspGlyMetGluAlaTyrValLysValAspSerCysProGluGluProGlnLeu 1081  CGCATGAAGAACAACGAGGAGGCCGAGGACTACGACGACGACCTGACCGACAGCGAGATGGACGTGGTGCGC
 355▶ ArgMetLysAsnAsnGluGluAlaGluAspTyrAspAspAspLeuThrAspSerGluMetAspValValArg
                   (BglII/BamHI)
1153  TTCGACGACGACAACAGCCCCAGCTTCATCCAGATCCGCAGCGTGGCCAAGAAGCACCCCAAGACCTGGGTG
 379▶ PheAspAspAspAsnSerProSerPheIleGlnIleArgSerValAlaLysLysHisProLysThrTrpVal 1225  CACTACATCGCCGCCGAGGAGGAGGACTGGGACTACGCCCCCCTGGTGCTGGCCCCCGACGACCGCAGCTAC
 403▶ HisTyrIleAlaAlaGluGluGluAspTrpAspTyrAlaProLeuValLeuAlaProAspAspArgSerTyr
                                                                         EagI
1297  AAGAGCCAGTACCTGAACAACGGCCCCCAGCGCATCGGCCGCAAGTACAAGAAGGTGCGCTTCATGGCCTAC
 427▶ LysSerGlnTyrLeuAsnAsnGlyProGlnArgIleGlyArgLysTyrLysLysValArgPheMetAlaTyr
                                                                         ApaI
1369  ACCGACGAGACCTTCAAGACCCGCGAGGCCATCCAGCACGAGAGCGGCATCCTGGGCCCCCTGCTGTACGGC
 451▶ ThrAspGluThrPheLysThrArgGluAlaIleGlnHisGluSerGlyIleLeuGlyProLeuLeuTyrGly
```

FIG. 9A

```
1441 GAGGTGGGCGACACCCTGCTGATCATCTTCAAGAACCAGGCCAGCCGCCCCTACAACATCTACCCCCACGGC
 475▶ GluValGlyAspThrLeuLeuIleIlePheLysAsnGlnAlaSerArgProTyrAsnIleTyrProHisGly
1513 ATCACCGACGTGCGCCCCCTGTACAGCCGCCGCCTGCCCAAGGGCGTGAAGCACCTGAAGGACTTCCCCATC
 499▶ IleThrAspValArgProLeuTyrSerArgArgLeuProLysGlyValLysHisLeuLysAspPheProIle
                                                                      BglII
1585 CTGCCCGGCGAGATCTTCAAGTACAAGTGGACCGTGACCGTGGAGGACGGCCCCACCAAGAGCGACCCCCGC
 523▶ LeuProGlyGluIlePheLysTyrLysTrpThrValThrValGluAspGlyProThrLysSerAspProArg
1657 TGCCTGACCCGCTACTACAGCAGCTTCGTGAACATGGAGCGCGACCTGGCCAGCGGCCTGATCGGCCCCCTG
 547▶ CysLeuThrArgTyrTyrSerSerPheValAsnMetGluArgAspLeuAlaSerGlyLeuIleGlyProLeu
1729 CTGATCTGCTACAAGGAGAGCGTGGACCAGCGCGGCAACCAGATCATGAGCGACAAGCGCAACGTGATCCTG
 571▶ LeuIleCysTyrLysGluSerValAspGlnArgGlyAsnGlnIleMetSerAspLysArgAsnValIleLeu
                                                        KpnI
1801 TTCAGCGTGTTCGACGAGAACCGCAGCTGGTACCTGACCGAGAACATCCAGCGCTTCCTGCCCAACCCCGCC
 595▶ PheSerValPheAspGluAsnArgSerTrpTyrLeuThrGluAsnIleGlnArgPheLeuProAsnProAla
1873 GGCGTGCAGCTGGAGGACCCCGAGTTCCAGGCCAGCAACATCATGCACAGCATCAACGGCTACGTGTTCGAC
 619▶ GlyValGlnLeuGluAspProGluPheGlnAlaSerAsnIleMetHisSerIleAsnGlyTyrValPheAsp
1945 AGCCTGCAGCTGAGCGTGTGCCTGCACGAGGTGGCCTACTGGTACATCCTGAGCATCGGCGCCCAGACCGAC
 643▶ SerLeuGlnLeuSerValCysLeuHisGluValAlaTyrTrpTyrIleLeuSerIleGlyAlaGlnThrAsp
2017 TTCCTGAGCGTGTTCTTCAGCGGCTACACCTTCAAGCACAAGATGGTGTACGAGGACACCCTGACCCTGTTC
 667▶ PheLeuSerValPhePheSerGlyTyrThrPheLysHisLysMetValTyrGluAspThrLeuThrLeuPhe
                                                                     BamHI
2089 CCCTTCAGCGGCGAGACCGTGTTCATGAGCATGGAGAACCCCGGCCTGTGGATCCTGGGCTGCCACAACAGC
 691▶ ProPheSerGlyGluThrValPheMetSerMetGluAsnProGlyLeuTrpIleLeuGlyCysHisAsnSer
2161 GACTTCGCAACCGCGGCATGACCGCCCTGCTGAAGGTGAGCAGCTGCGACAAGAACACCGGCGACTACTAC
 715▶ AspPheArgAsnArgGlyMetThrAlaLeuLeuLysValSerSerCysAspLysAsnThrGlyAspTyrTyr
2233 GAGGACAGCTACGAGGACATCAGCGCCTACCTGCTGAGCAAGAACAACGCCATCGAGCCCCGCAGGCGCAGG
 739▶ GluAspSerTyrGluAspIleSerAlaTyrLeuLeuSerLysAsnAsnAlaIleGluProArgArgArgArg
                                                                  BstXI
2305 CGCGAGATCACCCGCACCACCCTGCAGAGCGACCAGGAGGAGATCGACTACGACGACACCATCAGCGTGGAG
 763▶ ArgGluIleThrArgThrThrLeuGlnSerAspGlnGluGluIleAspTyrAspAspThrIleSerValGlu
2377 ATGAAGAAGGAGGACTTCGACATCTACGACGAGGACGAGAACCAGAGCCCCCGCAGCTTCCAGAAGAAGACC
 787▶ MetLysLysGluAspPheAspIleTyrAspGluAspGluAsnGlnSerProArgSerPheGlnLysLysThr
                                                                    PmlI
2449 CGCCACTACTTCATCGCCGCCGTGGAGCGCCTGTGGGACTACGGCATGAGCAGCAGCCCCCACGTGCTGCGC
 811▶ ArgHisTyrPheIleAlaAlaValGluArgLeuTrpAspTyrGlyMetSerSerSerProHisValLeuArg
2521 AACCGCGCCCAGAGCGGCAGCGTGCCCCAGTTCAAGAAGGTGGTTCCAGGAGTTCACCGACGGCAGCTTC
 835▶ AsnArgAlaGlnSerGlySerValProGlnPheLysLysValValPheGlnGluPheThrAspGlySerPhe
                                                                 ApaI
2593 ACCCAGCCCCTGTACCGCGGCGAGCTGAACGAGCACCTGGGCCTGCTGGGCCCCTACATCCGCGCCGAGGTG
 859▶ ThrGlnProLeuTyrArgGlyGluLeuAsnGluHisLeuGlyLeuLeuGlyProTyrIleArgAlaGluVal
            BstEII
2665 GAGGACAACATCATGGTGACCTTCCGCAACCAGGCCAGCCGCCCCTACAGCTTCTACAGCAGCCTGATCAGC
 883▶ GluAspAsnIleMetValThrPheArgAsnGlnAlaSerArgProTyrSerPheTyrSerSerLeuIleSer
2737 TACGAGGAGGACCAGCGCCAGGGCGCCGAGCCCCGCAAGAACTTCGTGAAGCCCAACGAGACCAAGACCTAC
 907▶ TyrGluGluAspGlnArgGlnGlyAlaGluProArgLysAsnPheValLysProAsnGluThrLysThrTyr
2809 TTCTGGAAGGTGCAGCACCACATGGCCCCCACCAAGGACGAGTTCGACTGCAAGGCCTGGGCCTACTTCAGC
 931▶ PheTrpLysValGlnHisHisMetAlaProThrLysAspGluPheAspCysLysAlaTrpAlaTyrPheSer
```

FIG. 9B

```
2881 GACGTGGACCTGGAGAAGGACGTGCACAGCGGCCTGATCGGCCCCCTGCTGGTGTGCCACACCAACACCCTG
 955▶ AspValAspLeuGluLysAspValHisSerGlyLeuIleGlyProLeuLeuValCysHisThrAsnThrLeu
           Eagl        BstEII
2953 AACCCCGCCCACGGCCGCCAGGTGACCGTGCAGGAGTTCGCCCTGTTCTTCACCATCTTCGACGAGACCAAG
 979▶ AsnProAlaHisGlyArgGlnValThrValGlnGluPheAlaLeuPhePheThrIlePheAspGluThrLys
3025 AGCTGGTACTTCACCGAGAACATGGAGCGCAACTGCCGCGCCCCCTGCAACATCCAGATGGAGGACCCCACC
1003▶ SerTrpTyrPheThrGluAsnMetGluArgAsnCysArgAlaProCysAsnIleGlnMetGluAspProThr
3097 TTCAAGGAGAACTACCGCTTCCACGCCATCAACGGCTACATCATGGACACCCTGCCCGGCCTGGTGATGGCC
1027▶ PheLysGluAsnTyrArgPheHisAlaIleAsnGlyTyrIleMetAspThrLeuProGlyLeuValMetAla
           KpnI
3169 CAGGACCAGCGCATCCGCTGGTACCTGCTGAGCATGGGCAGCAACGAGAACATCCACAGCATCCACTTCAGC
1051▶ GlnAspGlnArgIleArgTrpTyrLeuLeuSerMetGlySerAsnGluAsnIleHisSerIleHisPheSer
           PmlI
3241 GGCCACGTGTTCACCGTGCGCAAGAAGGAGGAGTACAAGATGGCCCTGTACAACCTGTACCCCGGCGTGTTC
1075▶ GlyHisValPheThrValArgLysLysGluGluTyrLysMetAlaLeuTyrAsnLeuTyrProGlyValPhe
3313 GAGACCGTGGAGATGCTGCCCAGCAAGGCCGGCATCTGGCGCGTGGAGTGCCTGATCGGCGAGCACCTGCAC
1099▶ GluThrValGluMetLeuProSerLysAlaGlyIleTrpArgValGluCysLeuIleGlyGluHisLeuHis
3385 GCCGGCATGAGCACCCTGTTCCTGGTGTACAGCAACAAGTGCCAGACCCCCCTGGGCATGGCCAGCGGCCAC
1123▶ AlaGlyMetSerThrLeuPheLeuValTyrSerAsnLysCysGlnThrProLeuGlyMetAlaSerGlyHis
           ApaI
3457 ATCCGCGACTTCCAGATCACCGCCAGCGGCCAGTACGGCCAGTGGGCCCCCAAGCTGGCCCGCCTGCACTAC
1147▶ IleArgAspPheGlnIleThrAlaSerGlyGlnTyrGlyGlnTrpAlaProLysLeuAlaArgLeuHisTyr
3529 AGCGGCAGCATCAACGCCTGGAGCACCAAGGAGCCCTTCAGCTGGATCAAGGTGGACCTGCTGGCCCCCATG
1171▶ SerGlySerIleAsnAlaTrpSerThrLysGluProPheSerTrpIleLysValAspLeuLeuAlaProMet
3601 ATCATCCACGGCATCAAGACCCAGGGCGCCCGCCAGAAGTTCAGCAGCCTGTACATCAGCCAGTTCATCATC
1195▶ IleIleHisGlyIleLysThrGlnGlyAlaArgGlnLysPheSerSerLeuTyrIleSerGlnPheIleIle
3673 ATGTACAGCCTGGACGGCAAGAAGTGGCAGACCTACCGCGGCAACAGCACCGGCACCCTGATGGTGTTCTTC
1219▶ MetTyrSerLeuAspGlyLysLysTrpGlnThrTyrArgGlyAsnSerThrGlyThrLeuMetValPhePhe
                                                         (SmaI/EcoRV)
3745 GGCAACGTGGACAGCAGCGGCATCAAGCACAACATCTTCAACCCCCCCATCATCGCCCGCTACATCCGCCTG
1243▶ GlyAsnValAspSerSerGlyIleLysHisAsnIlePheAsnProProIleIleAlaArgTyrIleArgLeu
3817 CACCCCACCCACTACAGCATCCGCAGCACCCTGCGCATGGAGCTGATGGGCTGCGACCTGAACAGCTGCAGC
1267▶ HisProThrHisTyrSerIleArgSerThrLeuArgMetGluLeuMetGlyCysAspLeuAsnSerCysSer
3889 ATGCCCCTGGGCATGGAGAGCAAGGCCATCAGCGACGCCCAGATCACCGCCAGCAGCTACTTCACCAACATG
1291▶ MetProLeuGlyMetGluSerLysAlaIleSerAspAlaGlnIleThrAlaSerSerTyrPheThrAsnMet
3961 TTCGCCACCTGGAGCCCCAGCAAGGCCCGCCTGCACCTGCAGGGCCGCAGCAACGCCTGGCGCCCCCAGGTG
1315▶ PheAlaThrTrpSerProSerLysAlaArgLeuHisLeuGlnGlyArgSerAsnAlaTrpArgProGlnVal
                                                                      BstEII
4033 AACAACCCCAAGGAGTGGCTGCAGGTGGACTTCCAGAAGACCATGAAGGTGACCGGCGTGACCACCCAGGGC
1339▶ AsnAsnProLysGluTrpLeuGlnValAspPheGlnLysThrMetLysValThrGlyValThrThrGlnGly
4105 GTGAAGAGCCTGCTGACCAGCATGTACGTGAAGGAGTTCCTGATCAGCAGCAGCCAGGACGGCCACCAGTGG
1363▶ ValLysSerLeuLeuThrSerMetTyrValLysGluPheLeuIleSerSerSerGlnAspGlyHisGlnTrp
4177 ACCCTGTTCTTCCAGAACGGCAAGGTGAAGGTGTTCCAGGGCAACCAGGACAGCTTCACCCCCGTGGTGAAC
1387▶ ThrLeuPhePheGlnAsnGlyLysValLysValPheGlnGlyAsnGlnAspSerPheThrProValValAsn
4249 AGCCTGGACCCCCCCCTGCTGACCCGCTACCTGCGCATCCACCCCCAGAGCTGGGTGCACCAGATCGCCCTG
1411▶ SerLeuAspProProLeuLeuThrArgTyrLeuArgIleHisProGlnSerTrpValHisGlnIleAlaLeu
                                                  SmaI      HindIII
4321 CGCATGGAGGTGCTGGGCTGCGAGGCCCAGGACCTGTACTAGCTGCCCGGGCTACAAGCTTTAC
1435▶ ArgMetGluValLeuGlyCysGluAlaGlnAspLeuTyr···
```

FIG. 9C

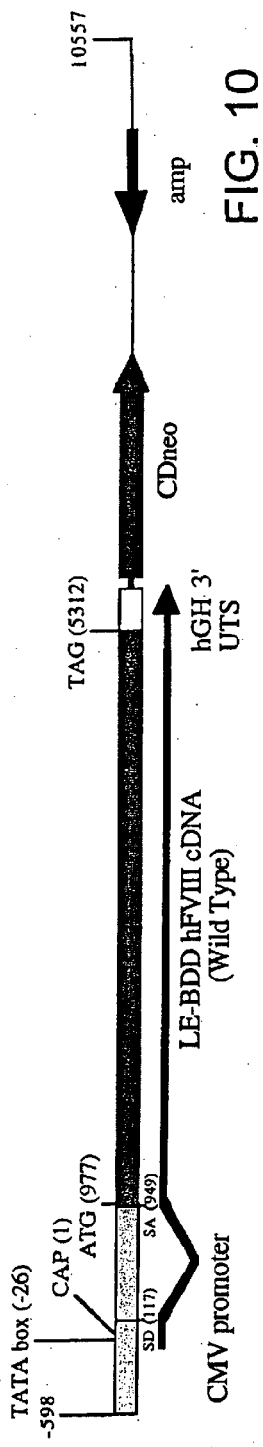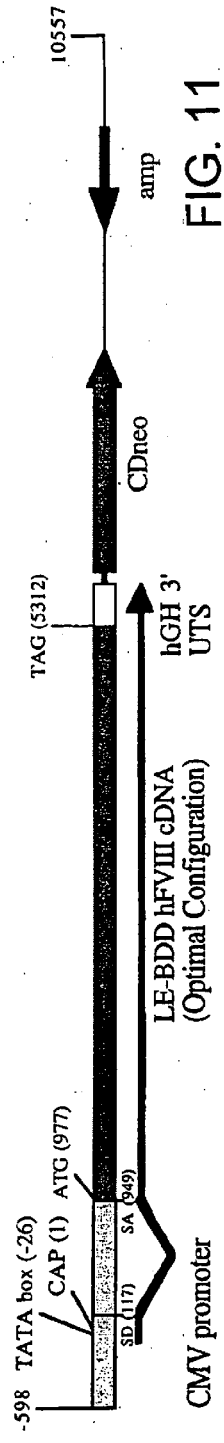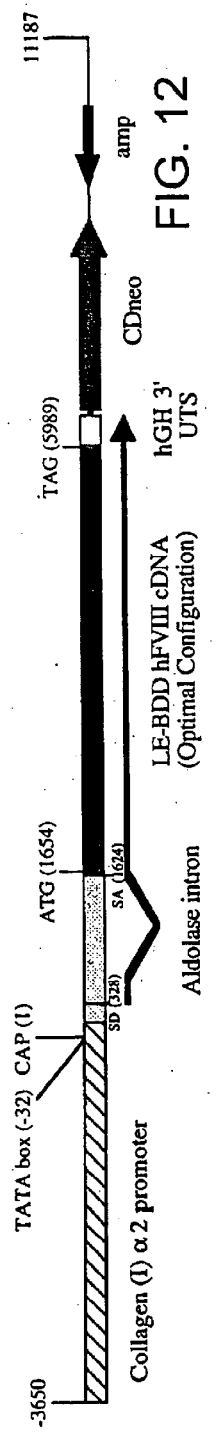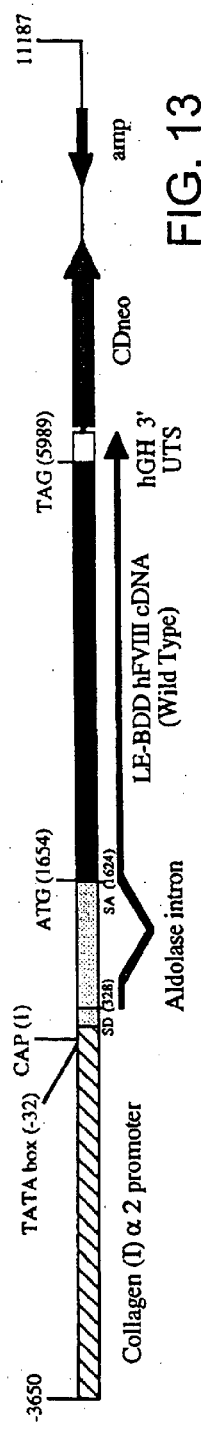

Codon Frequency in Highly Expressed Human Genes

| | | % occurrence | | | % occurrence | | | % occurrence |
|---|---|---|---|---|---|---|---|---|
| Glu | | | Cys | | | Gln | | |
| GA | A | 25 | TG | C | 68 | CA | A | 12 |
| | G | 75 | | T | 32 | | G | 88 |
| | | | | | | | | |
| Arg | | | Ala | | | Gly | | |
| CG | C | 37 | GC | C | 53 | GG | C | 50 |
| | T | 7 | | T | 17 | | T | 12 |
| | A | 6 | | A | 13 | | A | 14 |
| | G | 21 | | G | 17 | | G | 24 |
| AG | A | 10 | | | | | | |
| | G | 18 | | | | | | |
| | | | | | | | | |
| Leu | | | Ser | | | Pro | | |
| CT | C | 26 | TC | C | 28 | CC | C | 48 |
| | T | 5 | | T | 13 | | T | 19 |
| | A | 3 | | A | 5 | | A | 16 |
| | G | 58 | | G | 9 | | G | 17 |
| TT | A | 2 | AG | C | 34 | | | |
| | G | 6 | | T | 10 | | | |

FIG. 14A

Codon Frequency in Highly Expressed Human Genes

| Ile | | % occurrence | Thr | | % occurrence | Val | | % occurrence |
|---|---|---|---|---|---|---|---|---|
| AT | C | 77 | AC | C | 57 | GT | C | 25 |
|  | T | 18 |  | T | 14 |  | T | 7 |
|  | A | 5 |  | A | 14 |  | A | 5 |
|  |  |  |  | G | 15 |  | G | 64 |

| Tyr | | | Phe | | | Lys | | |
|---|---|---|---|---|---|---|---|---|
| TA | C | 74 | TT | C | 80 | AA | A | 18 |
|  | T | 26 |  | T | 20 |  | G | 82 |

| Asn | | | His | | | | | |
|---|---|---|---|---|---|---|---|---|
| AA | C | 78 | CA | C | 79 |  |  |  |
|  | T | 25 |  | T | 21 |  |  |  |

FIG. 14B

OPTIMIZED MESSENGER RNA

This application claims the benefit of prior U.S. provisional application 60/102,239, filed Sep. 29, 1998, and prior U.S. provisional application 60/130,241, filed Apr. 20, 1999, the contents of which are herein incorporated by reference.

FIELD OF THE INVENTION

The invention is directed to methods for optimizing the properties of mRNA molecules, optimized mRNA molecules, methods of using optimized mRNA molecules, and compositions which include optimized mRNA molecules.

BACKGROUND OF THE INVENTION

In Eukaroytes, gene expression is affected, in part, by the stability and structure of the messenger RNA (mRNA) molecule, mRNA stability influences gene expression by affecting the steady-state level of the mRNA; it can affect the rates at which the mRNA disappears following transcriptional repression and accumulates following transcriptional induction. The structure and nucleotide sequence of the mRNA molecule can also influence the efficiency with which these individual mRNA molecules are translated.

The intrinsic stability of a given mRNA molecule is influenced by a number of specific internal sequence elements which can exert a destabilizing effect on the mRNA. These elements may be located in any region of the transcript, and e.g., can be found in the 5' untranslated region (5'UTR), in the coding region and in the 3' untranslated region (3'UTR). It is well established that shortening of the poly(A) tail initiates mRNA decay (Ross, *Trends in Genetics*, 12:171–175, 1996). The poly(A) tract influences cytoplasmic mRNA stability by protecting mRNA from rapid degradation. Adenosine and uridine rich elements (AUREs) in the 3'UTR are also associated with unstable mammalian mRNA's. It has been demonstrated that proteins that bind to AURE, AURE-binding proteins (AUBPs), can affect mRNA stability. The coding region can also alter the half-life of many RNAs. For example, the coding region can interact with proteins that protect it from endonucleolytic attack. Furthermore, the efficiency with which individual mRNA molecules are translated has a strong influence on the stability of the mRNA molecule (Herrick et al., Mol Cell Biol. 10, 2269–2284, 1990, and Hoekema et al., Mol Cell Biol. 7, 2914–2924, 1987).

The single-stranded nature of mRNA allows it to adopt secondary and tertiary structure in a sequence-dependent manner through complementary base-pairing. Examples of such structures include RNA hairpins, stem loops and more complex structures such as bifurcations, pseudoknots and triple-helices. These structures influence both mRNA stability, e.g., the stem loop elements in the 3'UTR can serve as a endonuclease cleavage site, and affect translational efficiency.

In addition to the structure of the mRNA, the nucleotide content of the mRNA can also play a role in the efficiency with which the mRNA is translated. For example, mRNA with a high GC content at the 5'untranslated region (UTR) may be translated with low efficiency and a reduced translational effect can reduce message stability. Thus, altering the sequence of a mRNA molecule can ultimately influence mRNA transcript stability, by influencing the translational stability of the message.

Factor VIII and Factor IX are important plasma proteins that participate in the intrinsic pathway of blood coagulation. Their dysfunction or absence in individuals can result in blood coagulation disorders, e.g., a deficiency of Factor VIII or Factor IX results in Hemophilia A or B, respectively. Isolating Factor VIII or Factor IX from blood is difficult, e.g., the isolation of Factor VIII is characterized by low yields, and also has the associated danger of being contaminated with infectious agents such as Hepatitis B virus, Hepatitis C virus or HIV. Recombinant DNA technology provides an alternative method for producing biologically active Factor VIII or Factor IX. While these methods have had some success, improving the yield of Factor VIII or Factor IX is still a challenge.

An approach to increasing protein yield using recombinant DNA technology is to modify the coding sequence of a protein of interest, e.g., Factor VIII or Factor IX, without altering the amino acid sequence of the gene product. This approach involves altering, for example, the native Factor VIII or Factor IX gene sequence such that codons which are not so frequently used in mammalian cells are replaced with codons which are overrepresented in highly expressed mammalian genes. Seed et al., (WO 98/12207) used this approach with a measure of success. They found that substituting the rare mammalian codons with those frequently used in mammalian cells results in a four fold increase in Factor VIII production from mammalian cells.

SUMMARY OF THE INVENTION

In one aspect, the invention features, a synthetic nucleic acid sequence which encodes a protein, or a portion thereof, wherein at least one non-common codon or less-common codon has been replaced by a common codon, and wherein the synthetic nucleic acid sequence includes a continuous stretch of at least 90 codons all of which are common codons.

The synthetic nucleic acid can direct the synthesis of an optimized messenger mRNA. In a preferred embodiment the continuous stretch of common codons can include: the sequence of a pre-pro-protein; the sequence of a pro-protein; the sequence of a mature protein; the "pre" sequence of a pre-pro-protein; the "pre-pro" sequence of a pre-pro-protein; the "pro" sequence of a pre-pro or a pro-protein; or a portion of any of the aforementioned sequences.

In a preferred embodiment, the synthetic nucleic acid sequence includes a continuous stretch of at least 90, 95, 100, 125, 150, 200, 250, 300 or more codons all of which are common codons.

In another preferred embodiment, the nucleic acid sequence encoding a protein has at least 30, 50, 60, 75, 100, 200 or more non-common or less-common codons replaced with a common codon.

In a preferred embodiment, the number of non-common or less-common codons replaced is less than 15, 14, 13, 12, 11, 10, 9, 8, 7, 6, 5, 4, 3, 2 or 1.

In a preferred embodiment, the number of non-common or less-common codons remaining is less than 15, 14, 13, 12, 11, 10, 9, 8, 7, 6, 5, 4, 3, 2 or 1.

In preferred embodiments, the non-common and less-common codons replaced, taken together, are equal or less then 6%, 5%, 4%, 3%, 2%, 1% of the codons in the synthetic nucleic acid sequence.

In preferred embodiments, the non-common and less-common codons remaining, taken together, are equal or less then 6%, 5%, 4%, 3%, 2%, 1% of the codons in the synthetic nucleic acid sequence.

In a preferred embodiment, all of the non-common or less-common codons of the synthetic nucleic acid sequence encoding a protein have been replaced with common codons.

In a preferred embodiment, the synthetic nucleic acid sequence encodes a protein of at least about 90, 95, 100, 105, 110, 120, 130, 150, 200, 500, 700, 1000 or more amino acids in length.

In various preferred embodiments, at least 94%, 95%, 96%, 97%, 98%, 99%, or all, of the codons in the synthetic nucleic acid sequence are common codons. Preferably, all of the codons in the synthetic nucleic acid sequence are common codons.

In preferred embodiments, the protein is expressed in a eukaryotic cell, e.g., a mammalian cell, e.g., a human cell, and the protein is a mammalian protein, e.g., a human protein.

In another aspect, the invention features, a synthetic nucleic acid sequence which encodes a protein, or a portion thereof, wherein at least one non-common codon or less-common codon has been replaced by a common codon, and wherein the synthetic nucleic acid sequence includes a continuous stretch of common codons, which continuous stretch includes at least 33% or more of the codons in the synthetic nucleic acid sequence.

The synthetic nucleic acid can direct the synthesis of an optimized messenger mRNA. In a preferred embodiment the continuous stretch of common codons can include: the sequence of a pre-pro-protein; the sequence of a pro-protein; the sequence of a mature protein; the "pre" sequence of a pre-pro-protein; the "pre-pro" sequence of a pre-pro-protein; the "pro" sequence of a pre-pro or a pro-protein; or a portion of any of the aforementioned sequences.

In a preferred embodiment, the synthetic nucleic acid sequence includes a continuous stretch of common codons wherein the continuous stretch includes at least 35%, 40%, 50%, 60%, 70%, 80%, 90%, 95% or 100% of codons in the synthetic nucleic acid sequence.

In a preferred embodiment, the number of non-common or less-common codons replaced is less than 15, 14, 13, 12, 11, 10, 9, 8, 7, 6, 5, 4, 3, 2 or 1.

In a preferred embodiment, the number of non-common or less-common codons remaining is less than 15, 14, 13, 12, 11, 10, 9, 8, 7, 6, 5, 4, 3, 2 or 1.

In preferred embodiments, the non-common and less-common codons replaced, taken together, are equal or less then 6%, 5%, 4%, 3%, 2%, 1% of the codons in the synthetic nucleic acid sequence.

In preferred embodiments, the non-common and less-common codons remaining, taken together, are equal or less then 6%, 5%, 4%, 3%, 2%, 1% of the codons in the synthetic nucleic acid sequence.

In a preferred embodiment, all of the non-common or less-common codons of the synthetic nucleic acid sequence encoding a protein have been replaced with common codons.

In a preferred embodiment, all non-common and less-common codons are replaced with common codons.

In a preferred embodiment, the synthetic nucleic acid sequence encodes a protein of at least about 90, 95, 100, 105, 110, 120, 130, 150, 200, 500, 700, 1000 or more amino acids in length.

In various preferred embodiments, at least 94%, 95%, 96%, 97%, 98%, 99%, or all, of the codons in the synthetic nucleic acid sequence are common codons. Preferably, all of the codons in the synthetic nucleic acid sequence are common codons.

In preferred embodiments, the protein is expressed in a eukaryotic cell, e.g., a mammalian cell, e.g., a human cell, and the protein is a mammalian protein, e.g., a human protein.

In another aspect, the invention features, a synthetic nucleic acid sequence which encodes a protein, or a portion thereof, wherein at least one non-common codon or less-common codon has been replaced by a common codon, and wherein the number of non-common and less-common codons, taken together, is less than n/x, wherein nix is a positive integer, n is the number of codons in the synthetic nucleic acid sequence and x is chosen from 2, 4, 6, 10, 15, 20, 50, 150, 250, 500 and 1000. (Fractional values for n/x are rounded to the next highest of lowest integer, positive values below 0.5 are rounded down and values above 0.5 are rounded up).

The synthetic nucleic acid can direct the synthesis of an optimized messenger mRNA. In a preferred embodiment the continuous stretch of common codons can include: the sequence of a pre-pro-protein; the sequence of a pro-protein; the sequence of a mature protein; the "pre" sequence of a pre-pro-protein; the "pre-pro" sequence of a pre-pro-protein; the "pro" sequence of a pre-pro or a pro-protein; or a portion of any of the aforementioned sequences.

In a preferred embodiment, the number of codons in the synthetic nucleic acid sequence (n) is at least 50, 60, 70, 80, 90, 100, 120, 150, 200, 350, 400, 500 or more.

In a preferred embodiment, the number of non-common or less-common codons replaced is less than 15, 14, 13, 12, 11, 10, 9, 8, 7, 6, 5, 4, 3, 2 or 1.

In a preferred embodiment, the number of non-common or less-common codons remaining is less than 15, 14, 13, 12, 11, 10, 9, 8, 7, 6, 5, 4, 3, 2 or 1.

In preferred embodiments, the non-common and less-common codons replaced, taken together, are equal or less then 6%, 5%, 4%, 3%, 2%, 1% of the codons in the synthetic nucleic acid sequence.

In preferred embodiments, the non-common and less-common codons remaining, taken together, are equal or less then 6%, 5%, 4%, 3%, 2%, 1% of the codons in the synthetic nucleic acid sequence.

In a preferred embodiment, all non-common or less-common codons are replaced with common codons.

In various preferred embodiments, at least 94%, 95%, 96%, 97%, 98%, 99%, or all of the codons in the synthetic nucleic acid sequence are common codons. Preferably, all of the codons in the synthetic nucleic acid sequence are common codons.

In preferred embodiments, the protein is expressed in a eukaryotic cell, e.g., a mammalian cell, e.g., a human cell, and the protein is a mammalian protein, e.g., a human protein.

In another aspect, the invention features, a synthetic nucleic acid sequence which encodes a protein, or a portion thereof, wherein at least one non-common codon or less-common codon has been replaced by a common codon in the sequence that has not been optimized (non-optimized) which encodes the protein, wherein at least 94% or more of the codons in the sequence encoding the protein are common codons and wherein the synthetic nucleic acid sequence encodes a protein of at least about 90, 100 or 120 amino acids in length.

The synthetic nucleic acid can direct the synthesis of an optimized messenger mRNA. In a preferred embodiment the continuous stretch of common codons can include: the sequence of a pre-pro-protein; the sequence of a pro-protein; the sequence of a mature protein; the "pre" sequence of a pre-pro-protein; the "pre-pro" sequence of a pre-pro-protein; the "pro" sequence of a pre-pro or a pro-protein; or a portion of any of the aforementioned sequences.

In preferred embodiments, at least 94%, 95%, 96%, 97%, 98%, 99%, 99.5% or more of non-common or less-common codons in the non-optimized nucleic acid sequence encoding the protein have been replaced by a common codon encoding the same amino acid. Preferably, all non-common or less-common codon are replaced by a common codon encoding the same amino acid as found in the non-optimized sequence.

In a preferred embodiment, the synthetic nucleic acid sequence encodes a protein of at least about 90, 95, 100, 105, 110, 120, 130, 150, 200, 500, 700, 1000 or more amino acids in length.

In other preferred embodiments, at least 94%, 95%, 96%, 97%, 98%, 98.5%, 99%, 99.5% of the non-common codons in the non-optimized nucleic acid sequence are replaced with common codons. Preferably, all of the non-common codons are replaced with the common codons.

In other preferred embodiments at least 94%, 95%, 96%, 97%, 98%, 98%, 99%, 99.5% of the less-common codons in the non-optimized nucleic acid sequence are replaced with common codons. Preferably, all of the less-common codons are replaced with the common codons.

In preferred embodiments, at least 94% or more of the non-common and less common codons are replaced with common codons.

In preferred embodiments, the number of codons replaced which are not common codons is equal to or less than 15, 10, 9, 8, 7, 6, 5, 4, 3, 2, or 1.

In preferred embodiments, the number of codons remaining which are not common codons is equal to or less than 15, 10, 9, 8, 7, 6, 5, 4, 3, 2, or 1.

In preferred embodiments, the protein is expressed in a eukaryotic cell, e.g., a mammalian cell, e.g., a human cell, and the protein is a mammalian protein, e.g., a human protein.

The synthetic nucleic acid can direct the synthesis of an optimized messenger mRNA. In a preferred embodiment the continuous stretch of common codons can include: the sequence of a pre-pro-protein; the sequence of a pro-protein; the sequence of a mature protein; the "pre" sequence of a pre-pro-protein; the "pre-pro" sequence of a pre-pro-protein; the "pro" sequence of a pre-pro or a pro-protein; or a portion of any of the aforementioned sequences.

In a preferred embodiment the synthetic nucleic acid sequence is at least 100, 110, 120, 150, 200, 300, 500, 700, 1000 or more base pairs in length.

In another aspect, a synthetic nucleic acid sequence that directs the synthesis of an optimized message which encodes a Factor VIII protein having one or more of the following characteristics:

a) the B domain is deleted (BDD Factor VIII);
b) the synthetic nucleic acid sequence has a recognition site for an intracellular protease of the PACE/furin class, e.g., X—Arg—X—X—Arg (Molloy et al., J. Biol. Chem. 267:1639616401, 1992); a short-peptide linker, e.g., a two peptide linker, e.g., a leucine-glutamic acid peptide linker (LE), a three, or a four peptide linker, inserted at the heavy-light chain junction;
c) the synthetic nucleic acid sequence is introduced into a cell, e.g., a primary cell, a secondary cell a transformed or an immortalized human cell line. Examples of an immortalized human cell line useful in the present method include, but are not limited to; a Bowes Melanoma cell (ATCC Accession No. CRL 9607), a Daudi cell (ATCC Accession No. CCL 213), a HeLa cell and a derivative of a HeLa cell (ATCC Accession Nos. CCL 2, CCL2.1, and CCL 2.2), a HL-60 cell (ATCC Accession No. CCL 240), a HT1080 cell (ATCC Accession No. CCL 121), a Jurkat cell (ATCC Accession No. TIB 152), a KB carcinoma cell (ATCC Accession No. CCL 17), a K-562 leukemia cell (ATCC Accession No. CCL 243), a MCF-7 breast cancer cell (ATCC Accession No. BTH 22), a MOLT-4 cell (ATCC Accession No. 1582), a Namalwa cell (ATCC Accession No. CRL 1432), a Raji cell (ATCC Accession No. CCL 86), a RPMI 8226 cell (ATCC Accession No. CCL 155), a U-937 cell (ATCC Accession No. CRL 1593), WI-38VA13 sub line 2R4 cells (ATCC Accession No. CLL 75.1), a CCRF-CEM cell (ATCC Accession No. CCL 119) and a 2780AD ovarian carcinoma cell (Van Der Blick et al., Cancer Res. 48: 5927–5932, 1988), as well as heterohybridoma cells produced by fusion of human cells and cells of another species. In another embodiment, the immortalized cell line can be cell line other than a human cell line, e.g., a CHO cell line. In a preferred embodiment, the cell is a non-transformed cell. In various preferred embodiments, the cell is a mammalian cell, e.g., a primary or secondary mammalian cell, e.g., a fibroblast, a hematopoietic stem cell, a myoblast, a keratinocyte, an epithelial cell, an endothelial cell, a glial cell, a neural cell, a cell comprising a formed element of the blood, a muscle cell and precursors of these somatic cells. In a most preferred embodiment, the cell is a secondary human fibroblast.

In a preferred embodiment, the synthetic nucleic acid sequence which encodes a factor VIII protein has at least one, preferably at least two, and most preferably, all of the characteristics a, b, and c described above.

In preferred embodiments, at least one non-common codon or less-common codon of the synthetic nucleic acid has been replaced by a common codon and the synthetic nucleic acid has one or more of the following properties: it has a continuous stretch of at least 90 codons all of which are common codons; it has a continuous stretch of common codons which comprise at least 33% of the codons of the synthetic nucleic acid sequence; at least 94% or more of the codons in the sequence encoding the protein are common codons and the synthetic nucleic acid sequence encodes a protein of at least about 90, 100, or 120 amino acids in length; it is at least 80 base pairs in length and which is free of unique restriction endonuclease sites that would occur in the message optimized sequence.

In a preferred embodiment, the number of non-common or less-common codons replaced is less than 15, 14, 13, 12, 11, 10, 9, 8, 7, 6, 5, 4, 3, 2 or 1.

In a preferred embodiment, the number of non-common or less-common codons remaining is less than 15, 14, 13, 12, 11, 10, 9, 8, 7, 6, 5, 4, 3, 2 or 1.

In preferred embodiments, the non-common and less-common codons replaced, taken together, are equal or less then 6%, 5%, 4%, 3%, 2%, 1% of the codons in the synthetic nucleic acid sequence.

In preferred embodiments, the non-common and less-common codons remaining, taken together, are equal or less then 6%, 5%, 4%, 3%, 2%, 1% of the codons in the synthetic nucleic acid sequence.

In a preferred embodiment, all non-common or less-common codons are replaced with common codons.

In a preferred embodiment, all non-common and less-common codons are replaced with common codons.

In various preferred embodiments, at least 94%, 95%, 96%, 97%, 98%, 99%, or all of the codons in the synthetic nucleic acid sequence are common codons.

Preferably, all of the codons in the synthetic nucleic acid sequence are common codons.

In preferred embodiments, the protein is expressed in a eukaryotic cell, e.g., a mammalian cell, e.g., a human cell, and the protein is a mammalian protein, e.g., a human protein.

In a preferred embodiment, the synthetic nucleic acid sequence includes a continuous stretch of common codons wherein the continuous stretch comprises at least 35%, 40%, 50%, 60%, 70%, 80%, 90%, 95% or 100% of codons in the synthetic nucleic acid sequence.

In another aspect, the invention features, a synthetic nucleic acid sequence which can direct the synthesis of an optimized message which encodes a Factor IX protein having one or more of the following characteristics:
 a) it has a PACE/furin, such as a X—Arg—X—X—Arg site, at a pro-peptide mature protein junction; or
 b) is inserted, e.g., via transfection, into a non-transformed cell, e.g., a primary or secondary cell, e.g., a primary human fibroblast.

In a preferred embodiment, the synthetic nucleic acid sequence which encodes a factor IX protein has at least one, and preferably, both of the characteristics a and b described above.

In preferred embodiments, at least one non-common codon or less-common codon of the synthetic nucleic acid has been replaced by a common codon and the synthetic nucleic acid has one or more of the following properties: it has a continuous stretch of at least 90 codons all of which are common codons; it has a continuous stretch of common codons which comprise at least 33% of the codons of the synthetic nucleic acid sequence; at least 94% or more of the codons in the sequence encoding the protein are common codons and the synthetic nucleic acid sequence encodes a protein of at least about 90, 100, or 120 amino acids in length; it is at least 80 base pairs in length and is free of unique restriction endonuclease sites that occur in the message optimized sequence.

In a preferred embodiment, the number of non-common or less-common codons replaced is less than 15, 14, 13, 12, 11, 10, 9, 8, 7, 6, 5, 4, 3, 2 or 1.

In a preferred embodiment, the number of non-common or less-common codons remaining is less than 15, 14, 13, 12, 11, 10, 9, 8, 7, 6, 5, 4, 3, 2 or 1.

In preferred embodiments, the non-common and less-common codons replaced, taken together, are equal or less then 6%, 5%, 4%, 3%, 2%, 1% of the codons in the synthetic nucleic acid sequence.

In preferred embodiments, the non-common and less-common codons remaining, taken together, are equal or less then 6%, 5%, 4%, 3%, 2%, 1% of the codons in the synthetic nucleic acid sequence.

In a preferred embodiment, all non-common or less common codons are replaced with common codons.

In a preferred embodiment, all non-common and less-common codons are replaced with common codons.

In various preferred embodiments, at least 94%, 95%, 96%, 97%, 98%, 99%, or all of the codons in the synthetic nucleic acid sequence are common codons.

Preferably, all of the codons in the synthetic nucleic acid sequence are common codons.

In preferred embodiments, the protein is expressed in a eukaryotic cell, e.g., a mammalian cell, e.g., a human cell, and the protein is a mammalian protein, e.g., a human protein.

In a preferred embodiment, the synthetic nucleic acid sequence includes a continuous stretch of common codons wherein the continuous stretch comprises at least 35%, 40%, 50%, 60%, 70%, 80%, 90%, 95% or 100% of codons in the synthetic nucleic acid sequence.

In another aspect, the invention features, a plasmid or a DNA construct, e.g., an expression plasmid or a DNA construct, which includes a synthetic nucleic acid sequence described herein.

In yet another aspect, the invention features, a synthetic nucleic acid sequence described herein introduced into the genome of an animal cell. In a preferred embodiment, the animal cell is a primate cell, e.g., a mammal cell, e.g., a human cell.

In still another aspect, the invention features, a cell harboring a synthetic nucleic acid sequence described herein, e.g., a cell from a primary or secondary cell strain, or a cell from a continuous cell line, e.g., a Bowes Melanoma cell (ATCC Accession No. CRL 9607), a Daudi cell (ATCC Accession No. CCL 213), a HeLa cell and a derivative of a HeLa cell (ATCC Accession Nos. CCL 2, CCL2.1, and CCL 2.2), a HL-60 cell (ATCC Accession No. CCL 240), a HT1080 cell (ATCC Accession No. CCL 121), a Jurkat cell (ATCC Accession No. TIB 152), a KB carcinoma cell (ATCC Accession No. CCL 17), a K-562 leukemia cell (ATCC Accession No. CCL 243), a MCF-7 breast cancer cell (ATCC Accession No. BTH 22), a MOLT-4 cell (ATCC Accession No. 1582), a Namalwa cell (ATCC Accession No. CRL 1432), a Raji cell (ATCC Accession No. CCL 86), a RPMI 8226 cell (ATCC Accession No. CCL 155), a U-937 cell (ATCC Accession No. CRL 1593), a WI-38VA13 sub line 2R4 cell (ATCC Accession No. CLL 75.1), a CCRF-CEM cell (ATCC Accession No. CCL 119) and a 2780AD ovarian carcinoma cell (Van Der Blick et al., Cancer Res. 48: 5927–5932, 1988), as well as heterohybridoma cells produced by fusion of human cells and cells of another species. In another embodiment, the immortalized cell line can be a cell line other than a human cell line, e.g., a CHO cell line In a preferred embodiment, the cell is a non-transformed cell. In various preferred embodiments, the cell is a mammalian cell, e.g., a primary or secondary mammalian cell, e.g., a fibroblast, a hematopoietic stem cell, a myoblast, a keratinocyte, an epithelial cell, an endothelial cell, a glial cell, a neural cell, a cell comprising a formed element of the blood, a muscle cell and precursors of these somatic cells. In a most preferred embodiment, the cell is a secondary human fibroblast.

In another aspect, the invention features, a method for preparing a synthetic nucleic acid sequence encoding a protein which is, preferably, at least 90 codons in length, e.g., a synthetic nucleic acid sequence described herein. The method includes identifying non-common and less-common codons in the non-optimized gene encoding the protein and replacing at least, 94%, 95%, 96%, 97%, 98%, 99% or more of the non-common and less-common codons with a common codon encoding the same amino acid as the replaced codon. Preferably, all non-common and less-common codons are replaced with common codons.

In a preferred embodiment, the synthetic nucleic acid sequence encodes a protein of at least about 90, 95, 100, 105, 110, 120, 130, 150, 200, 500, 700, 1000 or more codons in length.

In preferred embodiments, the protein is expressed in a eukaryotic cell, e.g., a mammalian cell, e.g., a human cell, and the protein is a mammalian protein, e.g., a human protein.

In another aspect, the invention features, a method for making a nucleic acid sequence which directs the synthesis of a optimized message of a protein of at least 90, 100, or 120 amino acids in length, e.g., a synthetic nucleic acid sequence described herein. The method includes: synthesizing at least two fragments of the nucleic acid sequence, wherein the two fragments encode adjoining portions of the protein and wherein both fragments are mRNA optimized, e.g., as described herein; and joining the two fragments such that a non-common codon is not created at a junction point, thereby making the mRNA optimized nucleic acid sequence.

In a preferred embodiment, the two fragments are joined together such that a unique restriction endonuclease site used to create the two fragments is not recreated at the junction point. In another preferred embodiment, the two fragments are joined together such that a unique restriction site is created.

In a preferred embodiment, the synthetic nucleic acid sequence encodes a protein of at least about 90, 95, 100, 105, 110, 120, 130, 150, 200, 500, 700, 1000 or more codons in length.

In a preferred embodiment, at least 3, 4, 5, 6, 7, 8, 9, 10 or more fragments of the nucleic acid sequence are synthesized.

In a preferred embodiment, the fragments are joined together by a fission, e.g., a blunt end fusion.

In various preferred embodiments, at least 94%, 95%, 96%, 97%, 98%, 99%, or all of the codons in the synthetic nucleic acid sequence are common codons. Preferably, all of the codons in the synthetic nucleic acid sequence are common codons.

In preferred embodiments, the number of codons which are not common codons is equal to or less than 15, 10, 9, 8, 7, 6, 5, 4, 3, 2, or 1.

In preferred embodiments, each fragment is at least 30, 40, 50, 75, 100, 120, 150 or more codons in length.

In another aspect, the invention features, a method of providing a subject, e.g., a human, with a protein. The methods includes: providing a synthetic nucleic acid sequence that can direct the synthesis of an optimized message for a protein, e.g., a synthetic nucleic acid sequence described herein; introducing the synthetic nucleic acid sequence that directs the synthesis of an optimized message for a protein into the subject; and allowing the subject to express the protein, thereby providing the subject with the protein.

In preferred embodiments, the method further includes inserting the nucleic acid sequence that can direct the synthesis of an optimized message into a cell. The cell can be an autologous, allogeneic, or xenogeneic cell, but is preferably autologous. A preferred cell is a fibroblast, a hematopoietic stem cell, a myoblast, a keratinocyte, an epithelial cell, an endothelial cell, a glial cell, a neural cell, a cell comprising a formed element of the blood, a muscle cell and precursors of these somatic cells. The mRNA optimized synthetic nucleic acid sequence can be inserted into the cell ex vivo or in vivo. If inserted ex vivo, the cell can be introduced into the subject.

In preferred embodiments, at least 94%, 95%, 96%, 97%, 98%, 99%, or all of the codons in the synthetic nucleic acid sequence are common codons. Preferably, all of the codons in the synthetic nucleic acid sequence are common codons.

In preferred embodiments, the number of codons which are not common codons is equal to or less than 15, 10, 9, 8, 7, 6, 5, 4, 3, 2, or 1.

The invention also features synthetic nucleic acid fragments which encode a portion of a protein. Such synthetic nucleic acid fragments are similar to the synthetic nucleic acid sequences of the invention except that they encode only a portion of a protein. Such nucleic acid fragments preferably encode at least 50, 60, 70, 80, 100, 110, 120, 130, 150, 200, 300, 400, 500, or more contiguous amino acids of the protein.

The invention also features transfected or infected primary and secondary somatic cells of vertebrate origin, particularly of mammalian origin, e.g., of human, mouse, or rabbit origins, e.g., primary human cells, secondary human cells, or primary or secondary rabbit cells. The cells are transfected or infected with exogenous synthetic nucleic acid, e.g., DNA, described herein. The synthetic nucleic acid can encode a protein, e.g., a therapeutic protein, e.g., an enzyme, a cytokine, a hormone, an antigen, an antibody, a clotting factor, e.g., Factor VIII, Factor IX, or a regulatory protein. The invention also includes methods by which primary and secondary cells are transfected or infected to include exogenous synthetic DNA, methods of producing clonal cell strains or heterogenous cell strains, and methods of gene therapy in which the transfected or infected primary or secondary cells are used. The synthetic nucleic acid directs the synthesis of an optimized message, e.g., an optimized message as described herein.

The present invention includes primary and secondary somatic cells, which have been transfected or infected with an exogenous synthetic nucleic acid described herein, which is stably integrated into their genomes or is expressed in the cells episomally. In preferred embodiments the cells are fibroblasts, keratinocytes, epithelial cells, endothelial cells, glial cells, neural cells, cells comprising a formed element of the blood, muscle cells, other somatic cells which can be cultured, or somatic cell precursors. The resulting cells are referred to, respectively, as transfected or infected primary cells and transfected or infected secondary cells. The exogenous synthetic DNA encodes a protein, or a portion thereof, e.g., a therapeutic protein (e.g., Factor VIII or Factor IX). In an embodiment in which the exogenous synthetic DNA encodes a protein, or a portion thereof, to be expressed by the recipient cells, the resulting protein can be retained within the cell, incorporated into the cell membrane or secreted from the cell. In this embodiment, the exogenous synthetic DNA encoding the protein is introduced into cells along with additional DNA sequences sufficient for expression of the exogenous synthetic DNA in the cells. The additional DNA sequences may be of viral or non-viral origin. Primary cells modified to express exogenous synthetic DNA are referred to herein as transfected or infected primary cells, which include cells removed from tissue and placed on culture medium for the first time. Secondary cells modified to express or render available exogenous DNA are referred to herein as transfected or infected secondary cells.

Primary and secondary cells transfected or infected by the subject method, e.g., cloned cell strains, can be seen to fall into three types or categories: 1) cells which do not, as obtained, make or contain the therapeutic protein, 2) cells which make or contain the therapeutic protein but in lower quantities than normal (in quantities less than the physiologically normal lower level) or in defective form, and 3) cells which make the therapeutic protein at physiologically normal levels, but are to be augmented or enhanced in their content or production. Examples of proteins that can be made by the present method include cytokines or clotting factors.

Exogenous synthetic DNA is introduced into primary or secondary cell by a variety of techniques. For example, a DNA construct which includes exogenous synthetic DNA encoding a therapeutic protein and additional DNA sequences necessary for expression in recipient cells can be introduced into primary or secondary cells by electroporation, microinjection, or other means (e.g., calcium phosphate precipitation, modified calcium phosphate precipitation, polybrene precipitation, liposome fusion, receptor-mediated DNA delivery). Alternatively, a vector, such as a retroviral or other vector which includes exogenous synthetic DNA can be used and cells can be genetically modified as a result of infection with the vector.

In addition to the exogenous synthetic DNA, transfected or infected primary and secondary cells may optionally contain DNA encoding a selectable marker, which is expressed and confers upon recipients a selectable phenotype, such as antibiotic resistance, resistance to a cytotoxic agent, nutritional prototrophy or expression of a surface protein. Its presence makes it possible to identify and select cells containing the exogenous DNA. A variety of selectable marker genes can be used, such as neo, gpt, dhfr, ada, pac, hyg, mdr and hisD.

Transfected or infected cells of the present invention are useful, as populations of transfected or infected primary cells or secondary cells, transfected or infected clonal cell strains, transfected or infected heterogenous cell strains, and as cell mixtures in which at least one representative cell of one of the three preceding categories of transfected or infected cells is present, (e.g., the mixture of cells contains essentially transfected or infected primary or secondary cells and may include untransfected or uninfected primary or secondary cells) as a delivery system for treating an individual with an abnormal or undesirable condition which responds to delivery of a therapeutic protein, which is either: 1) a therapeutic protein (e.g., a protein which is absent, underproduced relative to the individual's physiologic needs, defective, or inefficiently or inappropriately utilized in the individual, e.g., Factor VIII; or 2) a therapeutic protein with novel functions, such as enzymatic or transport functions. In the method of the present invention of providing a therapeutic protein, transfected or infected primary cells or secondary cells, clonal cell strains or heterogenous cell strains, are administered to an individual in whom the abnormal or undesirable condition is to be treated or prevented, in sufficient quantity and by an appropriate route, to express the exogenous synthetic DNA at physiologically relevant levels. A physiologically relevant level is one which either approximates the level at which the product is produced in the body or results in improvement of the abnormal or undesirable condition.

Clonal cell strains of transfected or infected secondary cells (referred to as transfected or infected clonal cell strains) expressing exogenous synthetic DNA (and, optionally, including a selectable marker gene) can be produced by the method of the present invention. The method includes the steps of: 1) providing a population of primary cells, obtained from the individual to whom the transfected or infected primary cells will be administered or from another source; 2) introducing into the primary cells or into secondary cells derived from primary cells a DNA construct which includes exogenous DNA as described above and the necessary additional DNA sequences described above, producing transfected or infected primary or secondary cells; 3) maintaining transfected or infected primary or secondary cells under conditions appropriate for their propagation; 4) identifying a transfected or infected primary or secondary cell; and 5) producing a colony from the transfected or infected primary or secondary cell identified in (4) by maintaining it under appropriate culture conditions until a desired number of cells is obtained. The desired number of clonal cells is a number sufficient to provide a therapeutically effective amount of product when administered to an individual, e.g., an individual with hemophilia A is provided with a population of cells that produce a therapeutically effective amount of Factor VIII, such that that the condition is treated. The number of cells required for a given therapeutic dose depends on several factors including the expression level of the protein, the condition of the host animal and the limitations associated with the implantation procedure. In general, the number of cells required for implantation are in the range of $1 \times 10^6$ to $5 \times 10^9$, and preferably $1 \times 10^8$ to $5 \times 10^8$. In one embodiment of the method, the cell identified in (4) undergoes approximately 27 doublings (i.e., undergoes 27 cycles of cell growth and cell division) to produce 100 million clonal transfected or infected cells In another embodiment of the method, exogenous synthetic DNA is introduced into genomic DNA by homologous recombination between DNA sequences present in the DNA construct and genomic DNA. In another embodiment, the exogenous synthetic DNA is present episomally in a transfected cell, e.g., primary or secondary cell.

In one embodiment of producing a clonal population of transfected secondary cells, a cell suspension containing primary or secondary cells is combined with exogenous synthetic DNA encoding a therapeutic protein and DNA encoding a selectable marker, such as the neo gene. The two DNA sequences are present on the same DNA construct or on two separate DNA constructs. The resulting combination is subjected to electroporation, generally at 250–300 volts with a capacitance of 960 $\mu$Farads and an appropriate time constant (e.g., 14 to 20 m sec) for cells to take up the DNA construct. In an alternative embodiment, microinjection is used to introduce the DNA construct into primary or secondary cells. In either embodiment, introduction of the exogenous DNA results in production of transfected primary or secondary cells. The exogenous synthetic DNA introduced into the cell can be stably integrated into genomic DNA or is present episomally in the cell.

In the method of producing heterogenous cell strains of the present invention, the same steps are carried out as described for production of a clonal cell strain, except that a single transfected primary or secondary cell is not isolated and used as the founder cell. Instead, two or more transfected primary or secondary cells are cultured to produce a heterogenous cell strain. A heterogenous cell strain can also contain in addition to two or more transfected primary or secondary cells, untransfected primary or secondary cells.

The methods described herein have wide applicability in treating abnormal or undesired conditions and can be used to provide a variety of proteins in an effective amount to an individual. For example, they can be used to provide secreted proteins (with either predominantly systemic or predominantly local effects, e.g., Factor VIII and Factor IX), membrane proteins (e.g., for imparting new or enhanced cellular responsiveness, facilitating removal of a toxic product or for marking or targeting to a cell) or intracellular proteins (e.g., for affecting gene expression or producing autocrine effects).

A method described herein is particularly advantageous in treating abnormal or undesired conditions in that it: 1) is curative (one gene therapy treatment has the potential to last a patient's lifetime); 2) allows precise dosing (the patient's cells continuously determine and deliver the optimal dose of the required protein based on physiologic demands, and the stably transfected or infected cell strains can be characterized extensively in vitro prior to implantation, leading to accurate predictions of long term function in vivo); 3) is simple to apply in treating patients; 4) eliminates issues concerning patient compliance (following a one-time gene therapy treatment, daily protein injections are no longer necessary); and 5) reduces treatment costs (since the therapeutic protein is synthesized by the patient's own cells, investment in costly protein production and purification is unnecessary).

As used herein, the term "optimized messenger RNA" refers to a synthetic nucleic acid sequence encoding a protein wherein at least one non-common codon or less-common codon in the sequence encoding the protein has been replaced with a common codon.

By "common codon" is meant the most common codon representing a particular amino acid in a human sequence. The codon frequency in highly expressed human genes is outlined below in Table 1. Common codons include: Ala (gcc); Arg (cgc); Asn (aac); Asp (gac); Cys (tgc); Gln (cag); Gly (ggc); His (cac); Ile (atc); Leu (ctg); Lys (aag); Pro (ccc); Phe (ttc); Ser (agc); Thr (acc); Tyr (tac); Glu (gag); and Val (gtg) (see Table 1). "Less-common codons" are codons that occurs frequently in humans but are not the common codon: Gly (ggg); Ile (att); Leu (etc); Ser (tcc); Val (gtc); and Arg (agg). All codons other than common codons and less-common codons are "non-common codons".

TABLE 1

Codon Frequency in Highly Expressed Human Genes

| | | | % occurance | | | | % occurance |
|---|---|---|---|---|---|---|---|
| Ala | | | | Cys | | | |
| GC | | C | 53 | TG | | C | 68 |
| | | T | 17 | | | T | 32 |
| | | A | 13 | | | | |
| | | G | 17 | Gln | | | |
| | | | | CA | | A | 12 |
| Arg | | | | | | G | 88 |
| CG | | C | 37 | | | | |
| | | T | 7 | Glu | | | |
| | | A | 6 | GA | | A | 25 |
| | | G | 21 | | | G | 75 |
| AG | | A | 10 | | | | |
| | | G | 18 | Gly | | | |
| | | | | GG | | C | 50 |
| Asn | | | | | | T | 12 |
| AA | | C | 78 | | | A | 14 |
| | | T | 25 | | | G | 24 |
| Leu | | | | His | | | |
| CT | | C | 26 | CA | | C | 79 |
| | | T | 5 | | | T | 21 |
| | | A | 3 | | | | |
| | | G | 58 | Ile | | | |
| TT | | A | 2 | AT | | C | 77 |
| | | G | 6 | | | T | 18 |
| | | | | | | A | 5 |
| Lys | | | | | | | |
| AA | | A | 18 | Ser | | | |
| | | G | 82 | TC | | C | 28 |
| | | | | | | T | 13 |
| Pro | | | | | | A | 5 |
| CC | | C | 48 | | | G | 9 |
| | | T | 19 | AG | | C | 34 |
| | | A | 16 | | | T | 10 |
| | | G | 17 | | | | |
| | | | | Thr | | | |
| Phe | | | | AC | | C | 57 |
| TT | | C | 80 | | | T | 14 |
| | | T | 20 | | | A | 14 |
| | | | | | | G | 15 |
| | | | | Tyr | | | |
| | | | | TA | | C | 74 |
| | | | | | | T | 26 |
| | | | | Val | | | |
| | | | | GT | | C | 25 |
| | | | | | | T | 7 |
| | | | | | | A | 5 |
| | | | | | | G | 64 |

Codon frequency in Table 1 was calculated using the GCG program established by the University of Wisconsin Genetics Computer Group. Numbers represent the percentage of cases in which the particular codon is used.

The term "primary cell" includes cells present in a suspension of cells isolated from a vertebrate tissue source (prior to their being plated i.e., attached to a tissue culture substrate such as a dish or flask), cells present in an explant derived from tissue, both of the previous types of cells plated for the first time, and cell suspensions derived from these plated cells. The term secondary cell or cell strain refers to cells at all subsequent steps in culturing. That is, the first time a plated primary cell is removed from the culture substrate and replated (passaged), it is referred to herein as a secondary cell, as are all cells in subsequent passages. Secondary cells are cell strains which consist of secondary cells which have been passaged one or more times. A cell strain consists of secondary cells that: 1) have been passaged one or more times; 2) exhibit a finite number of mean population doublings in culture; 3) exhibit the properties of contact-inhibited, anchorage dependent growth (anchorage-dependence does not apply to cells that are propagated in suspension culture); and 4) are not immortalized. A "clonal cell strain" is defined as a cell strain that is derived from a single founder cell. A "heterogenous cell strain" is defined as a cell strain that is derived from two or more founder cells.

The term "tansfected cell" refers to a cell into which an exogenous synthetic nucleic acid sequence, e.g., a sequence which encodes a protein, is introduced. Once in the cell, the synthetic nucleic acid sequence can integrate into the recipients cells chromosomal DNA or can exist episomally. Standard transfection methods can be used to introduce the synthetic nucleic acid sequence into a cell, e.g., transfection mediated by liposome, polybrene, DEAE dextran-mediated transfection, electroporation, calcium phosphate precipitation or mircoinjection. The term "transfection" does not include delivery of DNA or RNA into a cell by a virus The term "infected cell" refers to a cell into which an exogenous synthetic nucleic acid sequence, e.g., a sequence which encodes a protein, is introduced by a virus. Viruses known to be useful for gene transfer include an *adenovirus*, an adeno-associated virus, a herpes virus, a mumps virus, a *poliovirus*, a *retrovirus*, a Sindbis virus, a *lentivirus* and a vaccinia virus such as a canary pox virus. Other features and advantages of the invention will be apparent from the following detailed description and the claims.

DETAILED DESCRIPTION

The drawings are first briefly described.

FIGS. 7A–7C, depict the nucleotide sequence and the corresponding amino acid sequence of the LE B-domain-deleted-Factor VIII (FVIII)insert contained in pAM1-1 (SEQ ID NO:1).

FIGS. 9A–9C, depict the nucleotide sequence and the corresponding amino acid sequence of the 5 Arg B-domain-deleted-FVIII insert (SEQ ID NO:2).

Figure 1:
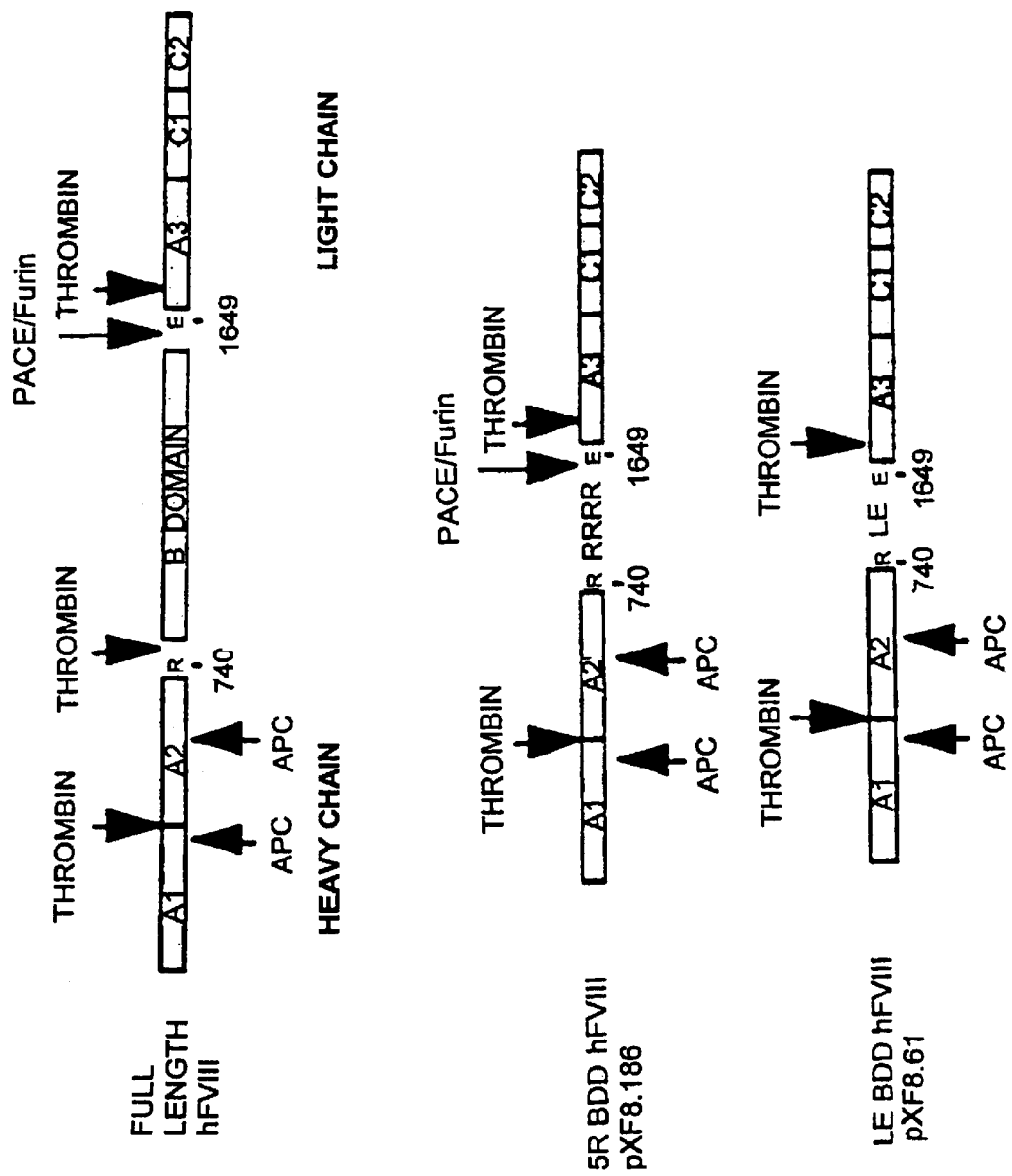
FIG. 1 is a schematic representation of domain structures of full-length and B-domain deleted human Factor VIII (hFVIII).

FIG. 10 is a schematic representation of the Factor VIII expression plasmid, pXF8.36. The cytomegalovirus immediate early I (CMV) promoter is depicted as a lightly shaded box. Positions of splice donor (SD) and splice acceptor (SA) sites are indicated below the shaded box. The Factor VIII cDNA sequence is depicted as a solid dark box. The hGH 3'UTS region is depicted as an open box. The new expression cassette is depicted as a shaded box with an arrowhead which corresponds to the direction of transcription. The thin dark line represents the plasmid backbone sequences. The position and direction of transcription of the β-lactamase gene (amp) is indicated by the solid boxed arrow.

FIG. 11 is a schematic representation of the Factor VIII expression plasmid, pXF8.38. The cytomegalovirus immediate early I (CMV) promoter is depicted as a lightly shaded box. Positions of splice donor (SD) and splice acceptor (SA) sites are indicated below the shaded box. The Factor VIII cDNA sequence is depicted as a solid dark box. The hGH 3'UTS region is depicted as an open box. The neo expression cassette is depicted as a shaded box with an arrowhead which corresponds to the direction of transcription. The thin dark line represents the plasmid backbone sequences. The position and direction of transcription of the β-lactamase gene (amp) is indicated by the solid boxed arrow.

FIG. 12 is a schematic representation of the Factor VIII expression plasmid, pXF8.269. The collagen (I) α 2 promoter is depicted as a striped box. The region representing aldolase-derived 5'untranslated sequences are depicted as a lightly shaded box. Positions of splice donor (SD) and splice acceptor (SA) sites are indicated below the shaded box. The Factor VIII cDNA sequence is depicted as a solid dark box. The hGH 3'UTS region is depicted as an open box. The neo expression cassette is depicted as a shaded box with an arrowhead which corresponds to the direction of transcription. The thin dark line represents the plasmid backbone sequences. The position and direction of transcription of the β-lactamase gene (amp) is indicated by the solid boxed arrow.

FIG. 13 is a schematic representation of the Factor VIII expression plasmid, pXF8.224. The collagen (I) α 2 promoter is depicted as a striped box. The region representing aldolase-derived 5'untranslated sequences are depicted as a lightly shaded box. Positions of splice donor (SD) and splice acceptor (SA) sites are indicated below the shaded box. The Factor VIII cDNA sequence is depicted as a solid dark box. The hGH 3'UTS region is depicted as an open box. The neo expression cassette is depicted as a shaded box with an arrowhead which corresponds to the direction of transcription. The thin dark line represents the plasmid backbone sequences. The position and direction of transcription of the β-lactamase gene (amp) is indicated by the solid boxed arrow.

FIGS. 14A–B is Table 1: Codon Frequency In Highly Expressed Human Genes.

Message Optimization

Methods of the invention are directed to optimized messages and synthetic nucleic acid sequences which direct the production of optimized mRNAs. An optimized mRNA can direct the synthesis of a protein of interest, e.g., a human protein, e.g. a human Factor VIII. A message for a protein of interest, e.g., human Factor VIII, can be optimized as described herein, e.g., by replacing at least 94%, 95%, 96%, 97%, 98%, 99%, and preferably all of the non-common codons or less-common codons with a common codon encoding the same amino acid as outlined in Table 1.

The coding region of a synthetic nucleic acid sequence can include the sequence "cg" without any discrimination, if the sequence is found in the common codon for that amino acid. Alternatively, the sequence "cg" can be limited in various regions, e.g., the first 20% of the coding sequence can be designed to have a low incidence of the sequence "cg".

Optimizing a message (and its synthetic DNA sequence) can negatively or positively affect gene expression or protein production. For example, replacing a less-common codon with a more common codon may affect the half life of the mRNA or alter its structure by introducing a secondary structure that interferes with translation of the message. It may therefore be necessary, in certain instances, to alter the optimized message.

All or a portion of a message (or its gene) can be optimized. In some cases the desired modulation of expression is achieved by optimizing essentially the entire message. In other cases, the desired modulation will be achieved by optimizing part but not all of the message or gene.

The codon usage of any coding sequence can be adjusted to achieve a desired property, for example high levels of expression in a specific cell type. The starting point for such an optimization may be a coding sequence with 100% common codons, or a coding sequence which contains a mixture of common and non-common codons.

Two or more candidate sequences that differ in their codon usage are generated and tested to determine if they possess the desired property. Candidate sequences may be evaluated initially by using a computer to search for the presence of regulatory elements, such as silencers or enhancers, and to search for the presence of regions of coding sequence which could be converted into such regulatory elements by an alteration in codon usage. Additional criteria may include enrichment for particular nucleotides, e.g., A, C, G or U, codon bias for a particular amino acid, or the presence or absence of particular mRNA secondary or tertiary structure. Adjustment to the candidate sequence can be made based on a number of such criteria.

Promising candidate sequences are constructed and then evaluated experimentally. Multiple candidates may be evaluated independently of each other, or the process can be iterative, either by using the most promising candidate as a new starting point, or by combining regions of two or more candidates to produce a novel hybrid. Further rounds of modification and evaluation can be included.

Modifying the codon usage of a candidate sequence can result in the creation or destruction of either a positive or negative element. In general, a positive element refers to any element whose alteration or removal from the candidate sequence could result in a decrease in expression of the therapeutic protein, or whose creation could result in an increase in expression of a therapeutic protein. For example, a positive element can include an enhancer, a promoter, a downstream promoter element, a DNA binding site for a positive regulator (e.g., a transcriptional activator), or a sequence responsible for imparting or removing mRNA secondary or tertiary structure. A negative element refers to any element whose alteration or removal from the candidate sequence could result in an increase in expression of the therapeutic protein, or whose creation would result in a decrease in expression of the therapeutic protein. A negative element includes a silencer, a DNA binding site for a negative regulator (e.g., a transcriptional repressor), a transcriptional pause site, or a sequence that is responsible for imparting or removing mRNA secondary or tertiary structure. In general, a negative element arises more frequently than a positive element. Thus, any change in codon usage that results in an increase in protein expression is more likely to have arisen from the destruction of a negative element rather than the creation of a positive element. In addition, alteration of the candidate sequence is more likely to destroy a positive element than create a positive element. In one embodiment, a candidate sequence is chosen and modified so as to increase the production of a therapeutic protein. The candidate sequence can be modified, e.g., by sequentially altering the codons or by randomly altering the codons in the candidate sequence. A modified candidate sequence is then evaluated by determining the level of expression of the resulting therapeutic protein or by evaluating another parameter, e.g., a parameter correlated to the level of expression. A candidate sequence which produces an increased level of a therapeutic protein as compared to an unaltered candidate sequence is chosen.

In another approach, one or a group of codons can be modified, e.g., without reference to protein or message structure and tested. Alternatively, one or more codons can be chosen on a message-level property, e.g., location in a region of predetermined, e.g., high or low, GC or AU content, location in a region having a structure such as an enhancer or silencer, location in a region that can be modified to introduce a structure such as an enhancer or silencer, location in a region having, or predicted to have, secondary or tertiary structure, e.g., intra-chain pairing, inter-chain pairing, location in a region lacking, or predicted to lack, secondary or tertiary structure, e.g., intra-chain or inter-chain pairing. A particular modified region is chosen if it produces the desired result.

Methods which systematically generate candidate sequences are useful. For example, one or a group, e.g., a contiguous block of codons, at various positions of a synthetic nucleic acid sequence can be replaced with common codons (or with non common codons, if for example, the starting sequence has been optimized) and the resulting sequence evaluated. Candidates can be generated by optimizing (or de-optimizing) a given "window" of codons in the sequence to generate a first candidate, and then moving the window to a new position in the sequence, and optimizing (or de-optimizing) the codons in the new position under the window to provide a second candidate. Candidates can be evaluated by determining the level of expression they provide, or by evaluating another parameter, e.g., a parameter correlated to the level of expression. Some parameters can be evaluated by inspection or computationally, e.g., the possession or lack thereof of high or low GC or AU content; a sequence element such as an enhancer or silencer; secondary or tertiary structure, e.g., intra-chain or inter-chain paring.

Thus, hybrid messages, i.e., messages having a region which is optimized and a region which is not optimized, can be evaluated to determine if they have a desired property. The evaluation can be effected by, e.g., synthesing the candidate message or messages, and determining a property such as its level of expression. Such a determination can be made in a cell-free system or in a cell-based system. The generation and testing of one or more candidates can also be performed, by computational methods, e.g., on a computer. For example, a computer program can be used to generate a number of candidate messages and those messages analysed by a computer program which predicts the existence of primary structure elements or secondary or tertiary structure.

A candidate message can be generated by dividing a region into subregions and optimizing each subregion. An optimized subregion is then combined with a non-optimized subregion to produce a candidate. For example, a region is divided into three subregions, a, b and c, each of which is then optimized to provide optimized subregions a', b' and c'. The optimized subregions, a', b', and c' can then be combined with one or more of the non-optimized subregions, e.g., a, b and c. For example, ab'c could be formed and tested. Different combinations of optimized and non-optimized subregions can be generated. By evaluating a series of such hybrid candidate sequences, it is possible to analyze the effect of modification of different subregions and, e.g., to define the particular version of each subregion that contributes most to the desired property. A preferred candidate can include the versions of each subregion that performed best in a series of such experiments.

An algorithm for creating an optimized candidate sequence is as follows:

1. Provide a message sequence (an entire message or a portion thereof). Go to step 2.
2. Generate a novel candidate sequence by modifying the codon usage of a candidate sequence by using, the most promising candidate sequence previously identified, or by combining regions of two or more candidates previously identified to produce a novel hybrid. Go to step 3.
3. Evaluate the candidate sequence and determine if it has a predetermined property. If the candidate has the predetermined property, then proceed to step 4, otherwise proceed to step 2.
4. Use the candidate sequence as an optimized message.

Methods can include first optimizing a mammalian synthetic nucleic acid sequence which encodes a protein of interest or a portion thereof, e.g., human Factor VIII, etc. The synthetic nucleic acid sequence can be optimized such that 94%, 95%, 96%, 97%, 98%, 99%, or all, of the codons of the synthetic DNA are replaced with common codons. The next step involves determining the amount of protein produced as a result of message optimization compared to the amount of protein produced using the wild type sequence. In instances where the amount of protein produced is not of the desired or expected level, it may be desirable to replace one or more of the common codons of the protein coding region with a less-common codon or non-common codon. A mammalian optimized message which is re-engineered such that common codons are replaced with less-common or non-common mammalian codons, or common codons of other eukaryotic species can result in at least 1%, 5%, 10%, 20% or more of the common codons being replaced. Re-engineering the optimized message can be done, for example, systematically by replacing a single common codon with a less-common or non-common codon. Alternatively, a block of 2, 4, 6, 10, 20, 40 or more codons may be replaced with a less-common or non-common codons. The level of protein produced by these "re-engineered optimized" messages determines which re-engineered optimized message is chosen.

Another approach of optimizing a message for increased protein expression includes altering the specific nucleotide content of an optimized synthetic nucleic acid sequence. The synthetic nucleic acid sequence can be altered by increasing or decreasing specific nucleotide(s) content, e.g., G, C, A, T, GC or AT content of the sequence. Increasing or decreasing the specific nucleotide content of a synthetic nucleotide sequence can be done by substituting the nucleotide of interest with another nucleotide. For example, a sequence that has a large number of codons that have a high GC content, e.g., glycine (GGC), can be substituted with codons that have a less GC rich content, e.g., glycine (GGT) or an AT rich codon. Similarly, a sequence that has a large number of codons that have a high AT content, can be substituted with codons that have a less AT rich content, e.g., a GC rich codon. Any region, or all, of a synthetic nucleic acid sequence can be altered in this manner, e.g., the 5'UTR (e.g., the promoter-proximal coding region), the coding region, the intron sequence, or the 3'UTR. Preferably, nucleotide substitutions in the coding region do not result in an alteration of the amino acid sequence of the expressed product. Preferably, the nucleotide content, e.g., GC or AT content, of a sequence is increased or reduced by 10%, 20%, 30%, 40% or more.

The synthetic nucleic acid sequence can encode a mammalian, e.g., a human protein. The protein can be, e.g., one which is endogenously a human, or an engineered protein. Engineered proteins include proteins which differ from the native protein by one or more amino acid residues. Examples of such proteins include fragments, e.g., internal fragments or truncations, deletions, fusion proteins, and proteins having one or more amino acid replacements.

A sequence which encodes the protein can have one or more introns. The synthetic nucleic acid sequence can include introns, as they are found in the non-optimized sequence or can include introns from a non-related gene. In other embodiments the intronic sequences can be modified. For example, all or part of one or more introns present in the gene can be removed or introns not found in the sequence can be added. In preferred embodiments, one or more entire introns present in the gene are not present in the synthetic nucleic acid. In another embodiment, all or part of an intron present in a gene is replaced by another sequence, e.g., an intronic sequence from another protein.

The synthetic nucleic acid sequence can encode: any protein including a blood factor, e.g., blood clotting factor V, blood clotting factor VII, blood clotting factor VIII, blood clotting factor IX, blood clotting factor X, or blood clotting factor XIII; an interleukin, e.g., interleukin 1, interleukin 2, interleukin 3, interleukin 6, interleukin 11, or interleukin 12; erthropoietin; calcitonin; growth hormone; insulin; insulinotropin; insulin-like growth factors; parathyroid hormone; β-interferon; γ-interferon; nerve growth factors; FSHβ; tumor necrosis factor; glucagon; bone growth factor-2; bone growth factor-7 TSH-β; CSF-granulocyte; CSF-macrophage; CSF-granulocyte/macrophage; immunoglobulins; catalytic antibodies; protein kinase C; glucoccrebroasidase; superoxide dismantase; tissue plasminogen activator; urokinase; antithrombin III; DNAse; α-galactosidase; tyrosine hydroxylase; apolipoprotein E; apolipoproetin A-I; globins; low density lipoprotein receptor; IL-2 receptor; IL-2 antagonists; alpha-1 antitrypsin; immune response modifiers; soluble CD4; a protein expressed under disease conditions; and proteins encoded by viruses, e.g., proteins which are encoded by a virus (including a retrovirus) which are expressed in mammalian cells post-infection.

In preferred embodiments, the synthetic nucleic acid sequence can express its protein, e.g., a eukaryotic e.g., mammalian, protein, at a level which is at least 110%, 150%, 200%, 500%, 1,000%, 5,000% or even 10,000% of that expressed by nucleic acid sequence that has not been optimized. This comparison can be made, e.g., in an in vitro mammalian cell culture system wherein the non-optimized and optimized sequence are expressed under the same conditions (e.g., the same cell type, same culture conditions, same expression vector).

Suitable cell culture systems for measuring expression of the synthetic nucleic acid sequence and corresponding non-optimized nucleic acid sequence are known in the art. (e.g., the pBS phagemic vectors, Stratagene, La Jolla, Calif.) and are described in, for example, the standard molecular biology reference books. Vectors suitable for expressing the synthetic and non-optimized nucleic acid sequences encoding the protein of interest are described below and in the standard reference books described below. Expression can be measured using an antibody specific for the protein of interest (e.g., ELISA). Such antibodies and measurement techniques are known to those skilled in the art.

In a preferred embodiment the protein is a human protein. In more preferred embodiments, the protein is human Factor VIII and the protein is a B domain deleted human Factor VII. In another preferred embodiment the protein is B domain deleted human Factor VIII with a sequence which includes a recognition site for an intracellular protease of the PACE/furin class, such as X—ARG—X—X—ARG site, a short-peptide linker, e.g., a two peptide linker, e.g., a leucine-glutamic acid peptide linker (LE), or a three, or four peptide linker, inserted at the heavy-light chain junction (see FIG. 1).

A large fraction of the codons in the human messages encoding Factor VIII and Factor IX are non-common codons or less common codons. Replacement of at least 98% of these codons with common codons will yield nucleic acid sequences capable of higher level expression in a cell culture. Preferably, all of the codons are replaced with common codons and such replacement results in at least a 5 fold, more preferably a 10 fold and most preferably a 20 fold increase in expression when compared to an expression of the corresponding native sequence in the same expression system.

The synthetic nucleic acid sequences of the invention can be introduced into the cells of a living organism. The sequences can be introduced directly, e.g., via homologous recombination, or via a vector. For example, DNA constructs or vectors can be used to introduce a synthetic nucleic acid sequence into cells of a living organism for gene therapy. Sec, e.g., U.S. Pat. No. 5,460,959; and co-pending U.S. applications U.S. Ser. No. 08/334,797; U.S. Ser. No. 08/231,439; U.S. Ser. No. 08/334,455; and U.S. Ser. No. 08/928,881 which are hereby expressly incorporated by reference in their entirety.

Transfected or Infected Cells

Primary and secondary cells to be transfected can be obtained from a variety of tissues and include cell types which can be maintained and propagated in culture. For example, primary and secondary cells which can be transfected include fibroblasts, keratinocytes, epithelial cells (e.g., mammary epithelial cells, intestinal epithelial cells), endothelial cells, glial cells, neural cells, a cell comprising a formed element of the blood (e.g., lymphocytes, bone marrow cells), muscle cells and precursors of these somatic cell types. Primary cells are preferably obtained from the individual to whom the transfected primary or secondary cells are administered. However, primary cells may be obtained from a donor (other than the recipient) of the same species or another species (e.g., mouse, rat, rabbit, cat, dog, pig, cow, bird, sheep, goat, horse).

Primary or secondary cells of vertebrate, particularly mammalian, origin can be transfected with exogenous synthetic DNA encoding a therapeutic protein and produce an encoded therapeutic protein stably and reproducibly, both in vitro and in vivo, over extended periods of time. In addition, the transfected primary and secondary cells can express the encoded product in vivo at physiologically relevant levels, cells can be recovered after implantation and, upon reculturing, to grow and display their preimplantation properties.

The transfected primary or secondary cells may also include DNA encoding a selectable marker which confers a selectable phenotype upon them, facilitating their identification and isolation. Methods for producing transfected primary, secondary cells which stably express exogenous synthetic DNA, clonal cell strains and heterogenous cell strains of such transfected cells, methods of producing the clonal and heterogenous cell strains, and methods of treating or preventing an abnormal or undesirable condition through the use of populations of transfected primary or secondary cells are part of the present invention. Primary and secondary cells which can be transfected include fibroblasts, keratinocytes, epithelial cells (e.g., mammary epithelial cells, intestinal epithelial cells), endothelial cells, glial cells, neural cells, a cell comprising a formed element of the blood (e.g., a lymphocyte, a bone marrow cell), muscle cells and precursors of these somatic cell types. Primary cells are preferably obtained from the individual to whom the transfected primary or secondary cells are administered. However, primary cells may be obtained from a donor (other than the recipient) of the same species or another species (e.g., mouse, rat, rabbit, cat, dog, pig, cow, bird, sheep, goat, horse). Transformed or immortalized cells can also be used e.g., a Bowes Melanoma cell (ATCC Accession No. CRL 9607), a Daudi cell (ATCC Accession No. CCL 213), a HeLa cell and a derivative of a HeLa cell (ATCC Accession Nos. CCL 2, CCL2.1, and CCL 2.2), a HL-60 cell (ATCC Accession No. CCL 240), a HT1080 cell (ATCC Accession No. CCL 121), a Jurkat cell (ATCC Accession No. TIB 152), a KB carcinoma cell (ATCC Accession No. CCL 17), a K-562 leukemia cell (ATCC Accession No. CCL 243), a MCF-7 breast cancer cell (ATCC Accession No. BTH 22), a MOLT-4 cell (ATCC Accession No. 1582), a Namalwa cell (ATCC Accession No. CRL 1432), a Raji cell (ATCC Accession No. CCL 86), a RPMI 8226 cell (ATCC Accession No. CCL 155), a U-937 cell (ATCC Accession No. CRL 1593), WI-38VA13 sub line 2R4 cells (ATCC Accession No. CLL 75.1), a CCRF-CEM cell (ATCC Accession No. CCL 119) and a 2780AD ovarian carcinoma cell (Van Der Blick et al., Cancer Res. 48: 5927–5932, 1988), as well as heterohybridoma cells produced by fusion of human cells and cells of another species. In another embodiment, the immortalized cell line can be a cell line other than a human cell line, e.g., a CHO cell line. In a preferred embodiment, the cell is a non-transformed cell. In various preferred embodiments, the cell is a mammalian cell, e.g., a primary or secondary mammalian cell, e.g., a fibroblast, a hematopoietic stem cell, a myoblast, a keratinocyte, an epithelial cell, an endothelial cell, a glial cell, a neural cell, a cell comprising a formed element of the blood, a muscle cell and precursors of these somatic cells. In a most preferred embodiment, the cell is a secondary human fibroblast.

Alternatively, DNA can be delivered into any of the cell types discussed above by a viral vector infection. Viruses known to be useful for gene transfer include adenoviruses, adeno-associated virus, herpes virus, mumps virus, poliovirus, retroviruses, Sindbis virus, and vaccinia virus such as canary pox virus. Use of viral vectors is well known in the art: see e.g., Robbins and Ghizzani, "Viral Vectors for Gene Therapy", *Mol. Med. Today* 1:410–417, 1995. A cell which has an exogenous DNA introduced into it by a viral vector is referred to as an "infected cell."

The invention also includes the genetic manipulation of a cell which normally produces a therapeutic protein. In this instance, the cell is manipulated such that the endogenous sequence which encodes the therapeutic protein is replaced with an optimized coding sequence, e.g., by homologous recombination.

Exogenous Synthetic DNA

Exogenous synthetic DNA incorporated into primary or secondary cells by the present method can be a synthetic DNA which encodes a protein, or a portion thereof, useful to treat an existing condition or prevent it from occurring.

Synthetic DNA incorporated into primary or secondary cells can be an entire gene encoding an entire desired protein or a gene portion which encodes, for example, the active or functional protion(s) of the protein. The protein can be, for example, a hormone, a cytokine, an antigen, an antibody, an enzyme, a clotting factor, e.g., Factor VIII or Factor XI, a transport protein, a receptor, a regulatory protein, a structural protein, or a protein which does not occur in nature. The DNA can be produced, using genetic engineering techniques or synthetic processes. The DNA introduced into primary or secondary cells can encode one or more therapeutic proteins. After introduction into primary or secondary cells, the exogenous synthetic DNA is stably incorporated into the recipient cell's genome (along with the additional sequences present in the DNA construct used), from which it is expressed or otherwise functions. Alternatively, the exogenous synthetic DNA may exist episomally within the primary or secondary cells.

Selectable Markers

A variety of selectable markers can be incorporated into primary or secondary cells. For example, a selectable marker which confers a selectable phenotype such as drug resistance, nutritional auxotrophy, resistance to a cytotoxic agent or expression of a surface protein, can be used. Selectable marker genes which can be used include neo, gpt, dhfr, ada, pac (puromycin), hyg and hisD. The selectable phenotype conferred makes it possible to identify and isolate recipient primary or secondary cells.

DNA Constructs

DNA constructs, which include exogenous synthetic DNA and, optionally, DNA encoding a selectable marker, along with additional sequences necessary for expression of the exogenous synthetic DNA in recipient primary or secondary cells, are used to transfect primary or secondary cells in which the encoded protein is to be produced. Alternatively, infectious vectors, such as retroviral, herpes, *lentivirus, adenovirus, adenovirus*-associated, mumps and poliovirus vectors, can be used for this purpose.

A DNA construct which includes the exogenous synthetic DNA and additional sequences, such as sequences necessary for expression of the exogenous synthetic DNA, can be used. A DNA construct which includes DNA encoding a selectable marker, along with additional sequences, such as a promoter, polyadenylation site and splice junctions, can be used to confer a selectable phenotype upon introduction into primary or secondary cells. The two DNA constructs are introduced into primary or secondary cells, using methods described herein. Alternatively, one DNA construct which includes exogenous synthetic DNA, a selectable marker gene and additional sequences (e.g., those necessary for expression of the exogenous synthetic DNA and for expression of the selectable marker gene) can be used.

Transfection of Primary or Secondary Cells and Production of Clonal or Heterogenous Cell Strains Vertebrate tissue can be obtained by standard methods such as punch biopsy or other surgical methods of obtaining a tissue source of the primary cell type of interest. For example, punch biopsy is used to obtain skin as a source of fibroblasts or keratinocytes. A mixture of primary cells is obtained from the tissue, using known methods, such as enzymatic digestion. If enzymatic digestion is used, enzymes such as collagenase, hyaluronidase, dispase, pronase, trypsin, elastase and chymotrypsin can be used.

The resulting primary cell mixture can be transfected directly or it can be cultured first, removed from the culture plate and resuspended before transfection is carried out. Primary cells or secondary cells are combined with exogenous synthetic DNA to be stably integrated into their genomes and, optionally, DNA encoding a selectable marker, and treated in order to accomplish transfection. The exogenous synthetic DNA and selectable marker-encoding DNA are each on a separate construct or on a single construct and an appropriate quantity of DNA to ensure that at least one stably transfected cell containing and appropriately expressing exogenous DNA is produced. In general, 0.1 to 500 ug DNA is used.

Primary or secondary cells, can be transfected by electroporation. Electroporation is carried out at appropriate voltage and capacitance (and time constant) to result in entry of the DNA construct(s) into the primary or secondary cells. Electroporation can be carried out over a wide range of voltages (e.g., 50 to 2000 volts) and capacitance values (e.g., 60–300 μFarads). Total DNA of approximately 0.1 to 500 ug is generally used.

Primary or secondary cells can be transfected using microinjection. Alternatively, known methods such as calcium phosphate precipitation, modified calcium phosphate precipitation and polybrene precipitation, liposome fusion and receptor-mediated gene delivery can be used to transfect cells. A stably, transfected cell is isolated and cultured and subcultivated, under culturing conditions and for sufficient time, to propagate the stably transfected secondary cells and produce a clonal cell strain of transfected secondary cells. Alternatively, more than one transfected cell is cultured and subculturated, resulting in production of a heterogenous cell strain.

Transfected primary or secondary cells undergo a sufficient number of doublings to produce either a clonal cell strain or a heterogenous cell strain of sufficient size to provide the therapeutic protein to an individual in effective amounts. In general, for example, 0.1 cm$^2$ of skin is biopsied and assumed to contain 100,000 cells; one cell is used to produce a clonal cell strain and undergoes approximately 27 doublings to produce 100 million transfected secondary cells. If a heterogenous cell strain is to be produced from an original transfected population of approximately 100,000 cells, only 10 doublings are needed to produce 100 million transfected cells.

The number of required cells in a transfected clonal or heterogenous cell strain is variable and depends on a variety of factors, including but not limited to, the use of the transfected cells, the functional level of the exogenous DNA in the transfected cells, the site of implantation of the transfected cells (for example, the number of cells that can be used is limited by the anatomical site of implantation), and the age, surface area, and clinical condition of the patient. To put these factors in perspective, to deliver therapeutic levels of human growth hormone in an otherwise healthy 10 kg patient with isolated growth hormone deficiency, approximately one to five hundred million transfected fibroblasts would be necessary (the volume of these cells is about that of the very tip of the patient's thumb).

Episomal Expression of Exogenous Synthetic DNA

DNA sequences that are present within the cell yet do not integrate into the genome are referred to as episomes. Recombinant episomes may be useful in at least three settings: 1) if a given cell type is incapable of stably integrating the exogenous synthetic DNA; 2) if a given cell type is adversely affected by the integration of synthetic DNA; and 3) if a given cell type is capable of improved therapeutic function with an episomal rather than integrated synthetic DNA.

Using transfection and culturing as described herein, exogenous synthetic DNA in the form of episomes can be introduced into vertebrate primary and secondary cells. Plasmids can be converted into such an episome by the addition DNA sequences for the Epstein-Barr virus origin of replication and nuclear antigen (Yates, J. L. *Nature* 319:780–7883 (1985)). Alternatively, vertebrate autonomously replicating sequences can be introduced into the construct (Weidle, U. H. *Gene* 73(2):427–437 (1988)). These and other episomally derived sequences can also be included in DNA constructs without selectable markers, such as pXGH5 (Selden et al., *Mol Cell Biol.* 6:3173–3179, 1986). The episomal synthetic exogenous DNA is then introduced into primary or secondary vertebrate cells as described in this application (if a selective marker is included in the episome a selective agent is used to treat the transfected cells).

Implantation of Clonal Cell Strain or Heterogenous Cell Strain of Transfected Secondary Cells The transfected cells produced as described above can be introduced into an individual to whom the therapeutic protein is to be delivered, using known methods. The clonal cell strain or heterogenous cell strain is then introduced into an individual, using known methods, using various routes of administration and at various sites (e.g., renal subcapsular, subcutaneous, central nervous system (including intrathecal), intravascular, intrahepatic, intrasplanchnic, intraperitoneal (including intraomental, or intramuscular implantation). In a preferred embodiment, the clonal cell strain or heterogeneous cell strain is introduced into the omentum. The omentum is a membranous structure containing a sheet of fat. Usually, the omentum is a fold of peritoneum extending from the stomach to adjacent abdominal organs. The greater omentim is attached to the inferior edge of the stomach and hangs down in front of the intestines. The other edge is attached to the transverse colon. The lesser omentum is attached to the superior edge of the stomach and extends to the undersurface of the liver. The cells may be introduced into any part of the omentum by surgical implantation, laparoscopy or direct injection, e.g., via CT-guided needle or ultrasound. Once implanted in the individual, the cells produce the therapeutic product encoded by the exogenous synthetic DNA or are affected by the exogenous synthetic DNA itself. For example, an individual who has been diagnosed with Hemophilia A, a bleeding disorder that is caused by a deficiency in Factor VIII, a protein normally found in the blood, is a candidate for a gene therapy treatment. In another example, an individual who has been diagnosed with Hemophilia B, a bleeding disorder that is caused by a deficiency in Factor IX, a protein normally found in the blood, is a candidate for a gene therapy treatment The patient has a small skin biopsy performed; this is a simple procedure which can be performed on an out-patient basis. The piece of skin, approximately the size of a matchhead, is taken, for example, from under the arm and requires about one minute to remove. The sample is processed, resulting in isolation of the patient's cells and genetically engineered to produce the missing Factor IX or Factor VIII. Based on the age, weight, and clinical condition of the patient, the required number of cells are grown in large-scale culture. The entire process requires 4–6 weeks and, at the end of that time, the appropriate number, e.g., approximately 100–500 million genetically-engineered cells are introduced into the individual, once again as an outpatient (e.g., by injecting them back under the patient's skin). The patient is now capable of producing his or her own Factor IX or Factor VIII and is no longer a hemophiliac.

A similar approach can be used to treat other conditions or diseases. For example, short stature can be treated by administering human growth hormone to an individual by implanting primary or secondary cells which express human growth hormone; anemia can be treated by administering erythropoietin (EPO) to an individual by implanting primary or secondary cells which express EPO; or diabetes can be treated by administering glucogen-like peptide-1 (GLP-1) to an individual by implanting primary or secondary cells which express GLP-1. A lysosomal storage disease (LSD) can be treated by this approach. LSD's represent a group of at least 41 distinct genetic diseases, each one representing a deficiency of a particular protein that is involved in lysosomal biogenesis. A particular LSD can be treated by administering a lysosomal enzyme to an individual by implanting primary or secondary cells which express the lysosomal enzyme, e.g., Fabry Disease can be treated by administering α-galactosidase to an individual by implanting primary or secondary cells which express α-galactosidase; Gaucher disease can be treated by administering β-glucoceramidase to an individual by implanting primary or secondary cells which express β-glucoceramidase; MPS (mucopolysaccharidosis) type 1 (Hurley-Scheie syndrome) can be treated by administering α-iduronidase to an individual by implanting primary or secondary cells which express α-iduronidase; MPS type II (Hunter syndrome) can be treated by administering α-L-iduronidase to an individual by implanting primary or secondary cells which express α-L-iduronidase; MPS type III-A (Sanfilipo A syndrome) can be treated by administering glucosamine-N-sulfatase to an individual by implanting primary or secondary cells which express glucosamine-N-sulfatase; MPS type III-B (Sanfilipo B syndrome) can be treated by administering alpha-N-acetylglucosaminidase to an individual by implanting primary or secondary cells which express alpha-N-acetylglucosaminidase; MPS type III-C (Sanfilipo C syndrome) can be treated by administering acetylcoenzyme A:α-glucosmainide-N-acetyltransferase to an individual by implanting primary or secondary cells which express acetylcoenzyme A:α-glucosmainide-N-acetyltransferase; MPS type 111-D (Sanfilippo D syndrome) can be treated by administering N-acetylglucosamine-6-sulfatase to an individual by implanting primary or secondary cells which express N-acetylglucosamine-6-sulfatase; MPS type IV-A (Morquip A syndrome) can be treated by administering N-Acetylglucosamine-6-sulfatase to an individual by implanting primary or secondary cells which express N-acetylglucosamine-6-sulfatase; MPS type IV-B (Morquio B syndrome) can be treated by administering β-galactosidase to an individual by implanting primary or secondary cells which express β-galactosidase; MPS type VI (Maroteaux-Larry syndrome) can be treated by administering N-acetylgalactosamine-6-sulfatase to an individual by implanting primary or secondary cells which express N-acetylgalactosamine-6-sulfatase; MPS type VII (Sly syndrome) can be treated by administering β-glucuronidase to an individual by implanting primary or secondary cells which express β-glucuronidase.

The cells used for implantation will generally be patient-specific genetically-engineered cells. It is possible, however, to obtain cells from another individual of the same species or from a different species. Use of such cells might require administration of an immunosuppressant, alteration of histocompatibility antigens, or use of a barrier device to prevent rejection of the implanted cells. For many diseases, this will be a one-time treatment and, for others, multiple gene therapy treatments will be required.

Uses of Transfected or Infected Primary and Secondary Cells and Cell Strains

Transfected or infected primary or secondary cells or cell strains have wide applicability as a vehicle or delivery system for therapeutic proteins, such as enzymes, hormones, cytokines, antigens, antibodies, clotting factors, anti-sense RNA, regulatory proteins, transcription proteins, receptors, structural proteins, novel (non-optimized) proteins and nucleic acid products, and engineered DNA. For example, transfected primary or secondary cells can be used to supply a therapeutic protein, including, but not limited to, Factor VIII, Factor IX, erythropoietin, alpha-I antitrypsin, calcitonin, glucocerebrosidase, growth hormone, low density lipoprotein (LDL), receptor IL-2 receptor and its antagonists, insulin, globin, immunoglobulins, catalytic antibodies, the interleukins, insulin-like growth factors, superoxide dismutase, immune responder modifiers, parathyroid hormone and interferon, nerve growth factors, tissue plasminogen activators, and colony stimulating factors. Alternatively, transfected primary and secondary cells can be used to immunize an individual (i.e., as a vaccine).

The wide variety of uses of cell strains of the present invention can perhaps most conveniently be summarized as shown below. The cell strains can be used to deliver the following therapeutic products.

1. a secreted protein with predominantly systemic effects;
2. a secreted protein with predominantly local effects;
3. a membrane protein imparting new or enhanced cellular responsiveness;
4. membrane protein facilitating removal of a toxic product;
5. a membrane protein marking or targeting a cell;
6. an intracellular protein;
7. an intracellular protein directly affecting gene expression; and
8. an intracellular protein with autocrine effects.

Transfected or infected primary or secondary cells can be used to administer therapeutic proteins (e.g., hormones, enzymes, clotting factors) which are presently administered intravenously, intramuscularly or subcutaneously, which requires patient cooperation and, often, medical staff participation. When transfected or infected primary or secondary cells are used, there is no need for extensive purification of the polypeptide before it is administered to an individual, as is generally necessary with an isolated polypeptide. In addition, transfected or infected primary or secondary cells of the present invention produce the therapeutic protein as it would normally be produced.

An advantage to the use of transfected or infected primary or secondary cells is that by controlling the number of cells introduced into an individual, one can control the amount of the protein delivered to the body. In addition, in some cases, it is possible to remove the transfected or infected cells if there is no longer a need for the product. A further advantage of treatment by use of transfected or infected primary or secondary cells of the present invention is that production of the therapeutic product can be regulated, such as through the administration of zinc, steroids or an agent which affects transcription of a protein, product or nucleic acid product or affects the stability of a nucleic acid product.

Transgenic Animals

A number of methods have been used to obtain transgenic, non-human mammals. A transgenic non-human mammal refers to a mammal that has gained an additional gene through the introduction of an exogenous synthetic nucleic acid sequence, i.e., transgene, into its own cells (e.g., both the somatic and germ cells), or into an ancestor's germ line.

There are a number of methods to introduce the exogenous DNA into the germ line (e.g., introduction into the germ or somatic cells) of a mammal. One method is by microinjection of a the gene construct into the pronucleus of an early stage embryo (e.g., before the four-cell stage) (Wagner, et al., *Proc. Natl. Acad. Sci.* USA 78:5016 (1981); Brinster, et al., Proc Natl Acad Sci USA 82:4438 (1985)). The detailed procedure to produce such transgenic mice has been described (see e.g., Hogan, et al., Manipulating the Mouse Embryo, Cold Spring Harbour Laboratory, Cold Spring Harbour, N.Y. (1986); U.S. Pat. No. 5,175,383 (1992)). This procedure has also been adapted for other mammalian species (e.g., Hammer, et al., Nature 315:680 (1985); Murray, et al., Reprod. Fert. Devl. 1:147 (1989); Pursel, et al., Vet. Immunol. Histopath. 17:303 (1987); Rexroad, et al., J. Reprod. Fert. 41 (suppl): 119 (1990); Rexroad, et al., Molec. Reprod. Devl. 1:164 (1989); Simons, et al., BioTechnology 6:179 (1988); Vize, et al., J. Cell. Sci. 90:295 (1988); and Wagner, J. Cell. Biochem. 13B (suppl) :164 (1989).

Another method for producing germ-line transgenic mammals is through the use of embryonic stem cells. The gene construct may be introduced into embryonic stem cells by homologous recombination (Thomas, et al., Cell 51:503 (1987); Capecchi, Science 244:1288 (1989); Joyner, et al., Nature 338: 153 (1989)). A suitable construct may also be introduced into the embryonic stem cells by DNA-mediated transfection, such as electroporation (Ausubel, et al., Current Protocols in Molecular Biology, John Wiley & Sons (1987)). Detailed procedures for culturing embryonic stem cells (e.g. ESD-3, ATCC# CCL-1934, ES-E14TG-2a, ATCC# CCL-1821, American Type Culture Collection, Rockville, Md.) and the methods of making transgenic mammals from embryonic stem cells can be found in Teratocarcinomas and Embryonic Stem Cells, A Practical Approach, ed. E. J. Robertson (IRL Press, 1987).

In the above methods for the generation of a germ-line transgenic mammals, the construct may be introduced as a linear construct, as a circular plasmid, or as a vector which may be incorporated and inherited as a transgene integrated into the host genome. The transgene may also be constructed so as to permit it to be inherited as an extrachromosomal plasmid (Gassmann, M. et al., *Proc. Natl. Acad. Sci.* USA 92:1292 (1995)).

Figure 2:
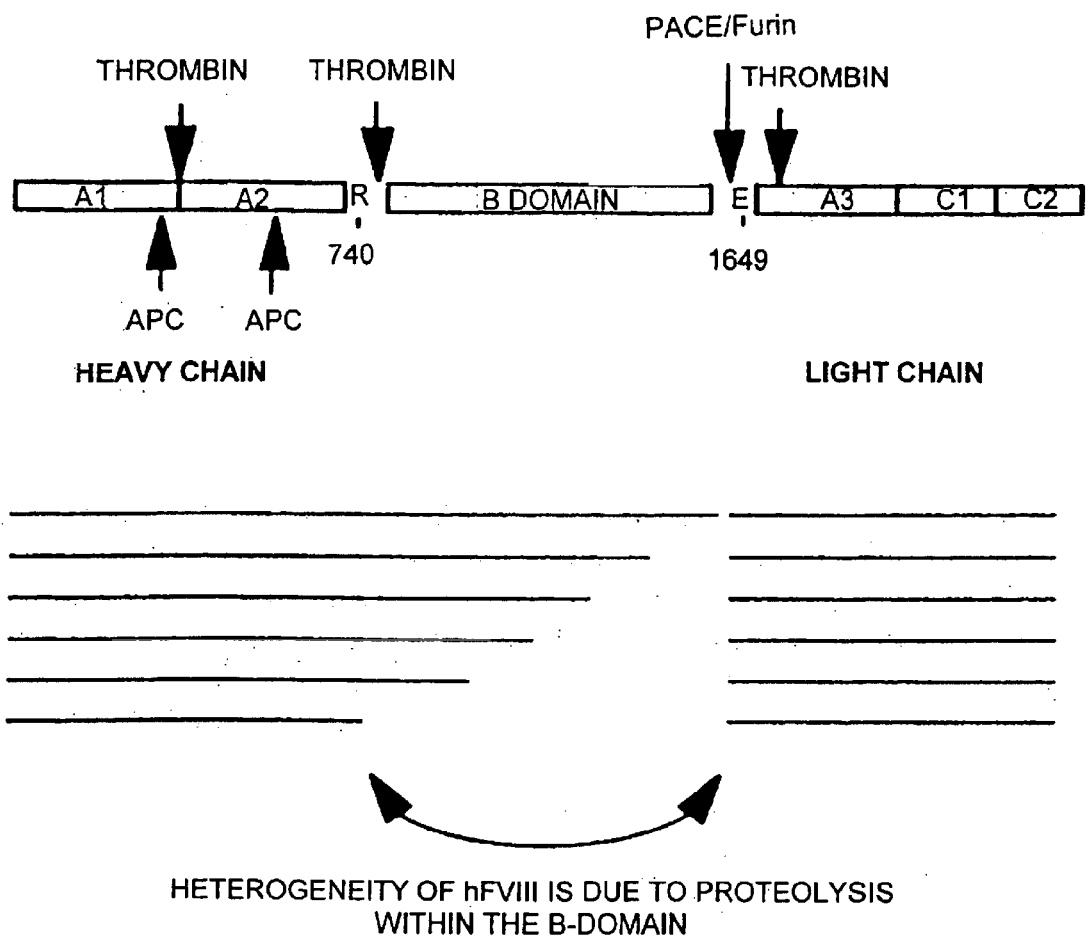
FIG. 2 is a schematic representation of full-length hFVIII.

Human Factor VIE hFVIII is encoded by a 186 kilobase (kb) gene, with the coding region distributed among 26 exons (Gitchier et al., *Nature,* 312:326–330, (1984)). Transcription of the gene and splicing of the resulting primary transcript results in an mRNA of approximately 9 kb which encodes a primary translation product containing 2351 amino acids (aa), including a 19 aa signal peptide. Excluding the signal peptide, the 2332 aa protein has a domain structure which can be represented as NH2-A1-A2-B-A3-C1-C2-COOH, with a predicted molecular mass of 265 kilodaltons (kD). Glycosylation of this protein results in a product with a molecular mass of approximately 330 kD as determined by SDS-PAGE. In plasma, hFVIII is a heterodimeric protein consisting of a heavy chain that ranges in size from 90 kD to 200 kD in a metal ion complex with an 80 kD light chain. The heterodimeric complex is further stabilized by interactions with vWF. The heavy chain is comprised of domains A1-A2-B and the light chain is comprised of domains A3-C1-C2 (FIG. 2). Protease cleavage sites in the B-domain account for the size variation of the heavy chain, with the 90 kD species containing no B-domain sequences and the 200 kD species containing a complete or nearly complete B-domain. The B-domain has no known function and it is fully removed upon hFVIII activation by thrombin.

Figure 3:
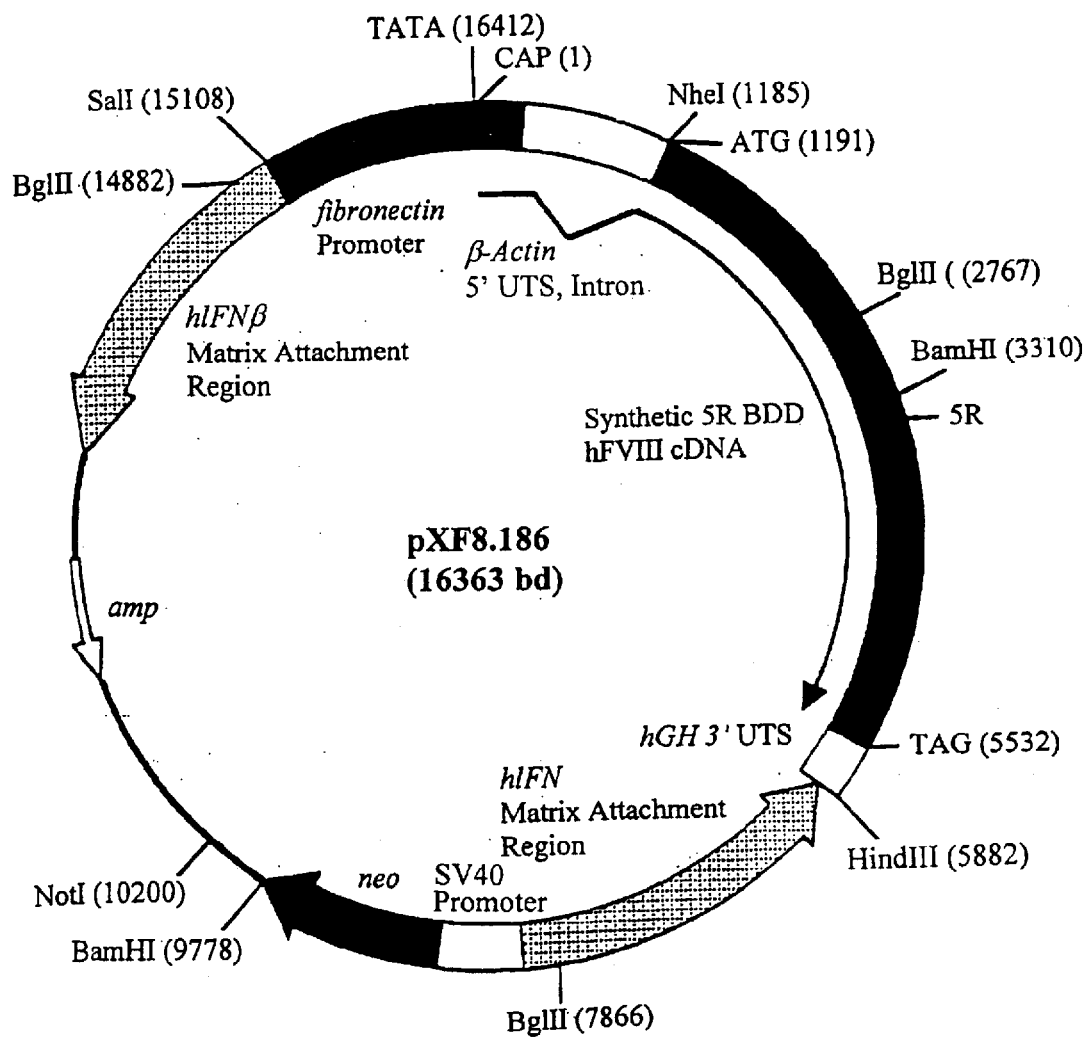
FIG. 3 is a schematic representation of 5R BDD hFVIII expression plasmid pXF8.186.
Figure 4:
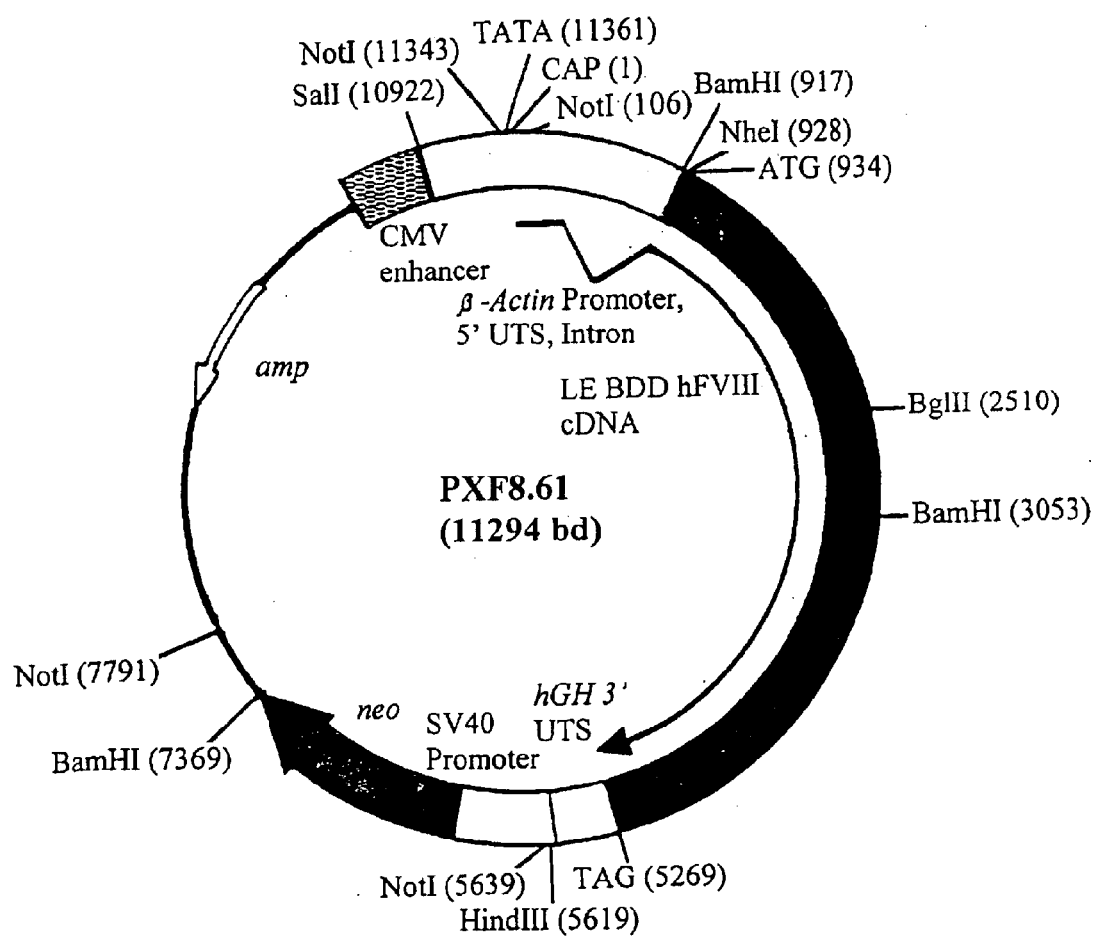
FIG. 4 is a schematic representation of LE BDD hFVIII expression plasmid pXF8.61.

Human Factor VIII expression plasmids, plasmids pXF8.186 (FIG. 3), pXF8.61 (FIG. 4), pXF8.38 (FIG. 11) and pXF8.224 (FIG. 13) are described below. The hFVIII expression construct plasmid pXF8.186, was developed based on detailed optimization studies which resulted in high level expression of a functional hFVIII. Given the extremely large size of the hFVIII gene and the need to transfer the entire coding region into cells, cDNA expression plasmids were developed for the production of stably transfected clonal cell strains. It has proven difficult to achieve high level expression of hFVIII using the wild-type 9 kb cDNA. Three potential reasons for the poor expression are as follows. First, the wild-type cDNA encodes the 909 aa, heavily glycosylated B-domain which is transiently attached to the heavy chain and has no known function (FIG. 1). Removal of the region encoding the B-domain from hFVIII expression constructs leads to greatly improved expression of a functional protein. Analysis of hFVIII derivatives lacking the B-domain has demonstrated that hFVIII function is not adversely affected and that such molecules have biochemical, immunologic, and in vivo functional properties which are very similar to the wild-type protein. Two different BDD hFVIII expression constructs have been developed, which encode proteins with different amino acid sequences flanking the deletion. Plasmid pXF8.186 contains a complete deletion of the B-domain (amino acids 741–1648 of the wild-type mature protein sequence), with the sequence Arg—Arg—Arg—Arg (RRRR; SEQ ID NO:135) inserted at the heavy chain-light chain junction (FIG. 1). This results in a string of five consecutive arginine residues (RRRRR or 5R; SEQ ID NO:136) at the heavy chain-light chain junction, which comprises a recognition site for an intracellular protease of the PACE/furin class, and was predicted to promote cleavage to produce the correct heavy and light chains. Plasmid pXF8.61 also contains a complete deletion of the B-domain with a synthetic XhoI site at the junction. This linker results in the presence of the dipeptide sequence Leu-Glu (LE) at the heavy chain-light chain junction in the two forms of BDD hFVIII, the expressed proteins are referred to herein as 5R and LE BDD hFVIII.

The second feature which has been reported to adversely affect hFVIII expression in transfected cells relates to the observation that one or more regions of the coding region have been identified which effectively function to block transcription of the cDNA sequence. The inventors have now discovered that the negative influence of the sequence elements can be reduced or eliminated by altering the entire coding sequence. To this end, a completely synthetic B-domain deleted hFVIII cDNA was prepared as described in greater detail below. Silent base changes were made in all codons which did not correspond to the triplet sequence most frequently found for that amino acid in highly expressed human proteins, and such codons were converted to the codon sequence most frequently found in humans for the corresponding amino acid. The resulting coding sequence has a total of 1094 of 4335 base pairs which differ from the wild-type sequence, yet it encodes a protein with the wild-type hFVIII sequence (with the exception of the deletion of the B-domain). 25.2% of the bases were changed, and the GC content of the sequence increased from 44% to 64%. This sequence-altered BDD hFVIII cDNA is expressed at least 5.3-fold more efficiently than a non-altered control construct.

The third feature which was optimized to improve hFVIII expression was the intron-exon structure of the expression construct. The cDNA is, by definition, devoid of introns. While this reduces the size of the expression construct, it has been shown that introns can have strong positive effects on gene expression when added to cDNA expression constructs. The 5'untranslated region of the human beta-actin gene, which contains a complete, functional intron was incorporated into the BDD hFVIII expression constructs pXF8.61 and pXF8.186.

The fourth feature which can adversely affect hFVIII expression is the stability of the Factor VIII mRNA. The stability of the message can affect the steady-state level of the Factor VIII mRNA, and influence gene expression. Specific sequences within Factor VIII can be altered so as to increase the stability of the mRNA, e.g., the removal of AURE from the 3'UTR can result in a more stable Factor VIII mRNA. The data presented below show that coding sequence re-engineering has general utility for the improvement of expression of mammalian and non-mammalian eukaryotic genes in mammalian cells. The results obtained here with human Factor VIII suggest that systemic codon optimization (with disregard to CpG content) provides a fruitful strategy for improving the expression in mammalian cells of a wide variety of eukaryotic genes.

Methods of Making Synthetic Nucleotide Sequences

A synthetic nucleic acid sequence which directs the synthesis of an optimized message of the invention can be made, e.g., by any of the methods described herein. The methods described below are advantageous for making optimized messages for the following reasons:

1) they allow for production of a highly optimized protein, e.g., a protein having at least 94 to 100% of codons as common codons, especially for proteins larger than 90 amino acids in length. The final product can be 100% optimized, i.e., every single nucleotide is as chosen, without the need to introduce undesirable alterations every 100–300 bp. A gene can be synthesized with 100% optimized codons, or it can be synthesized with 100% the codons that are desired. Additional DNA sequence elements can be introduced or avoided without any limitations imposed by the need to introduce restriction enzyme sites. Such sequence elements could include:

Transcriptional signals, such as enhancers or silencers.

Splicing signals, for example avoiding cryptic splice sites in a cDNA, or optimizing the splice site context in an intron-containing gene. Adding an intron to a cDNA may aid expression and allows the introduction of transcriptional signals within the gene.

Instability signals—the creation or avoidance of sequences that direct mRNA breakdown.

Secondary structure—the creation or avoidance of secondary structures in the mRNA that may affect mRNA stability, transcriptional termination, or translation.

Translational signals—Codon choice. A gene can be synthesized with 100% optimal codons, or the codon bias for any amino acid can be altered without restriction to make gene expression sensitive to the concentration of an amino-acyl-tRNA, whose concentration may vary with growth or metabolic conditions.

In each case, the goal may be to increase or decrease expression to bring expression under a particular form of regulation.

2) they improve accuracy of the synthetic sequence because they avoid PCR amplification which introduces errors into the amplified sequence; and 3) they reduce the cost of making the synthetic sequence of the invention.

The synthetic nucleic acid sequence which direct the synthesis of the optimized messages of the invention can be prepared, e.g., by using the strategy which is outlined in greater detail below.

Strategy for Building a Sequence

The initial step is to devise a cloning protocol.

A sequence file containing 100% the desired DNA sequence is generated. This sequence is analyzed for restriction sites, including fusion sites.

Fusion sites are, in order of preference:

A) Sequences resulting from the ligation of two complementary overhangs normally generated by available restriction enzymes, e.g.,

| | |
|---|---|
| SalI/XhoI = | G^TCGAG |
| | CAGCT^C |
| or BspDI/BstBI = | AT^CGAA |
| | TAGC^TT |
| or BstBI/AccI = | TT^CGAC |
| | AAGC^TG. |

B) Sequences resulting from the ligation of two overhangs generated by partially filling-in the overhangs of available restriction enzymes, e.g.,

| | |
|---|---|
| XhoI(+TC)/BamHI(+GA) = | CTC^GATCC. |
| | GAGCT^AGG |

C) Sequences resulting from the blunt ligation of two blunt ends normally generated by available restriction enzymes, e.g.,

| | |
|---|---|
| EheI/SmaI = | GGC^GGG |
| | CCG^CCC. |

D) Sequences resulting from the blunt ligation of two blunt ends, where one or both blunt ends have been generated by filling in an overhang, e.g.,

| | |
|---|---|
| BamHI(+GATC)/SmaI = | GGATC^GGG |
| | CCTAG^CCC |

The filling-in of a 5' overhang generated by a restriction enzyme is performed using a DNA polymerase, for example the Klenow fragment of DNA Polymerase I. If the overhang is to be filled in completely, then all four nucleotides, dATP, dCTP, dGTP, and dTTP, are included in the reaction. If the overhang is to be only partially filled in, then the requisite nucleotides are omitted from the reaction, In item (B) above, the XhoI-digested DNA would be filled in by Klenow in the presence of dCTP and dTTP and by omitting dATP and dGTP. An order of cloning steps is determined that allows the use of sites about 150–500 bp apart. Note that a fragment must lack the recognition sequence for an enzyme, only if that enzyme is used to clone the fragment. For example, the strategy for the construction of the "desired" Factor VIII coding sequence can use ApaLI in a number of different places, because of the order of assembly of the fragments—ApaLI is not used in any of the later cloning steps.

If there is a region where no useful sites are available, then a sequence-independent strategy can be used: fragments are cloned into a DNA construct that contain recognition sequences for restriction enzymes that cleave outside of their recognition sequence,

| e.g. BseRI = | GAGGAGNNNNNNNNNN^ (SEQ ID NO:5) |
| | CTCCTCNNNNNNNN^NN (SEQ ID NO:6) |

DNA construct cloning site gene fragment.

The recognition sequence of the enzyme used to clone the fragment will be removed when the fragment is released by digestion with, e.g. BseRI, leaving a fragment consisting of 100% of the desired sequence, which can then be ligated to a similarly generated adjacent gene fragment.

The next step is to synthesize initial restriction fragments.

The synthesis of the initial restriction fragments can be achieved in a number of ways, including, but not limited to:

1. Chemical synthesis of the entire fragment.
2. Synthesize two oligonucleotides that are complementary at their 3' ends, anneal them, and use DNA polymerase Klenow fragment, or equivalent, to extend, giving a double-stranded fragment.
3. Synthesize a number of smaller oligonucleotides, kinase those oligo's that have internal 5' ends, anneal all oligo's and ligate, viz.

```
5'____p_____p_____3'
3'_____p_____p____5'
```

Techniques 2 and 3 can be used in subsequent steps to join smaller fragments to each other. PCR can be used to increase the quantity of material for cloning, but it may lead to an increase in the number of mutations. If an error-free fragment is not obtained, then site-directed mutagenesis can be used to correct the best isolate. This is followed by concatenation of error-free fragments and sequencing of junctions to confirm their precision.

Use

The synthetic nucleic acid sequences of the invention are useful for expressing a protein normally expressed in a mammalian cell, or in cell culture (e.g. for commercial production of human proteins such as GH, tPA, GLP-1, EPO, α-galactosidase, β-glucoceramidase, α-iduronidase; α-L-iduronidase, glucosamine-N-sulfatase, alpha-N-acetylglucosaminidase, acetylcoenzyme A:α-glucosmainide-N-acetyltransferase, N-acetylglucosamine-6-sulfatase, N-acetylglucosamine-6-sulfatase, β-galactosidase, N-acetylgalactosamine-6sulfatase, β-glucuronidase. Factor VIII, and Factor IX). The synthetic nucleic acid sequences of the invention are also useful for gene therapy. For example, a synthetic nucleic acid sequence encoding a selected protein can be introduced directly, e.g., via non-viral cell transfection or via a vector in to a cell, e.g., a transformed or a non-transformed cell, which can express the protein to create a cell which can be administered to a patient in need of the protein. Such cell-based gene therapy techniques are described in greater detail in co-pending US applications: U.S. Ser. No. 08/334,797; U.S. Ser. No. 08/231,439; U.S. Ser. No. 08/334,455; and U.S. Ser. No. 08/928,881, which are hereby expressly incorporated by reference in their entirety.

EXAMPLES

Construction of pXF8.61

Figure 5E:
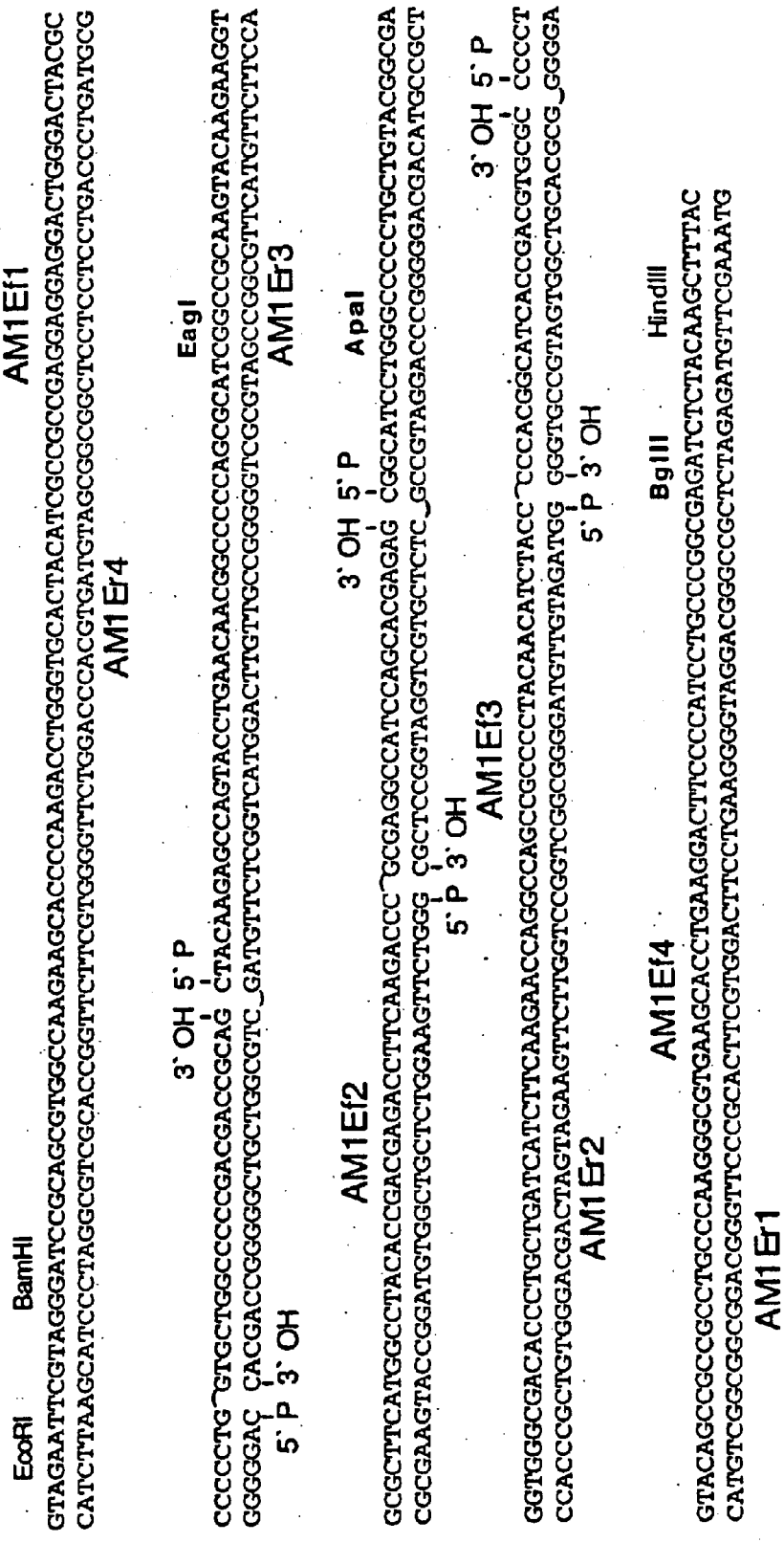
FIGS. 5A–5N, are a schematic representation of the fourteen fragments (Fragments A-Fragment N) assembled to construct pXF8.61.
Figure 5G:
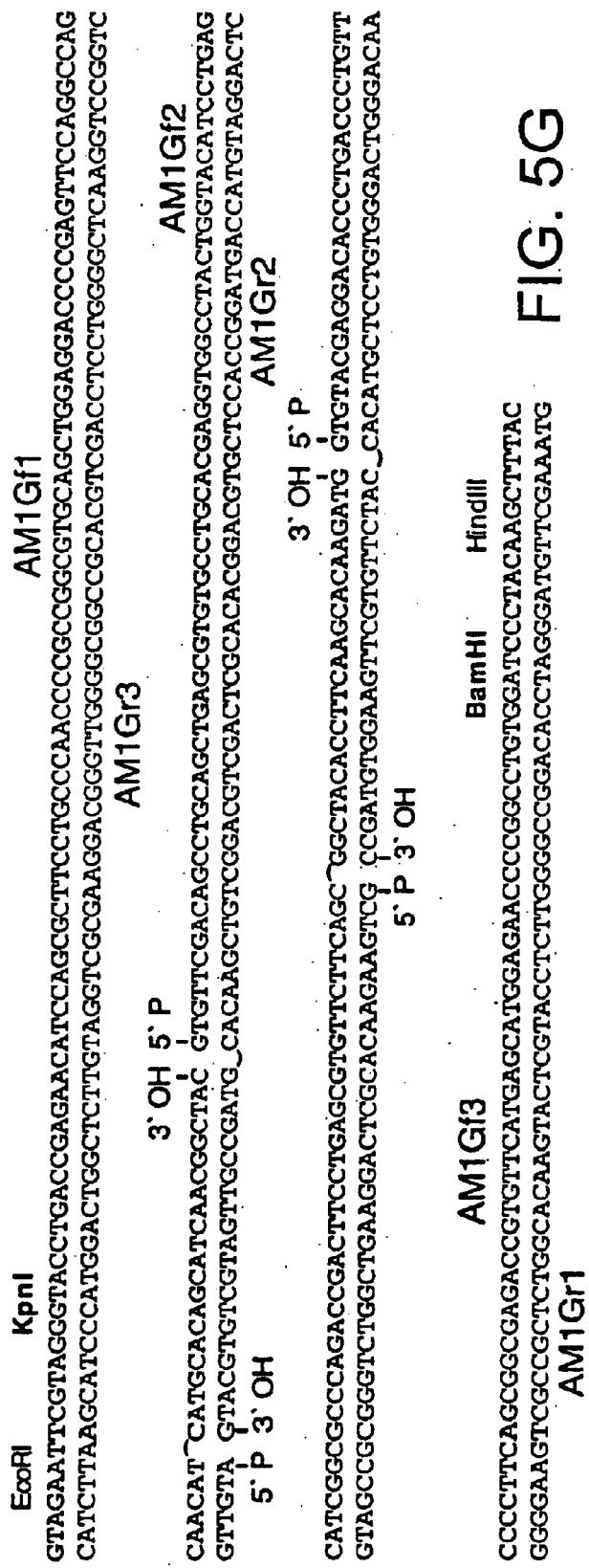
Figure 5L:
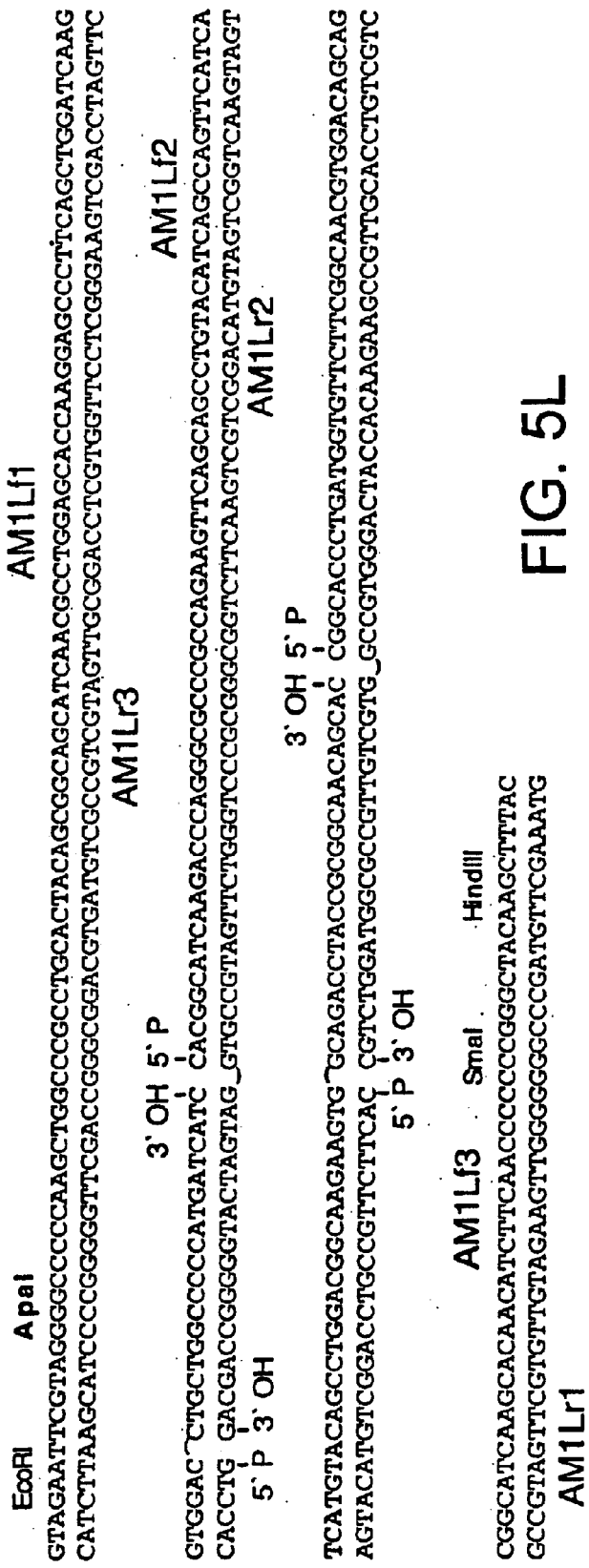
Figure 6A:
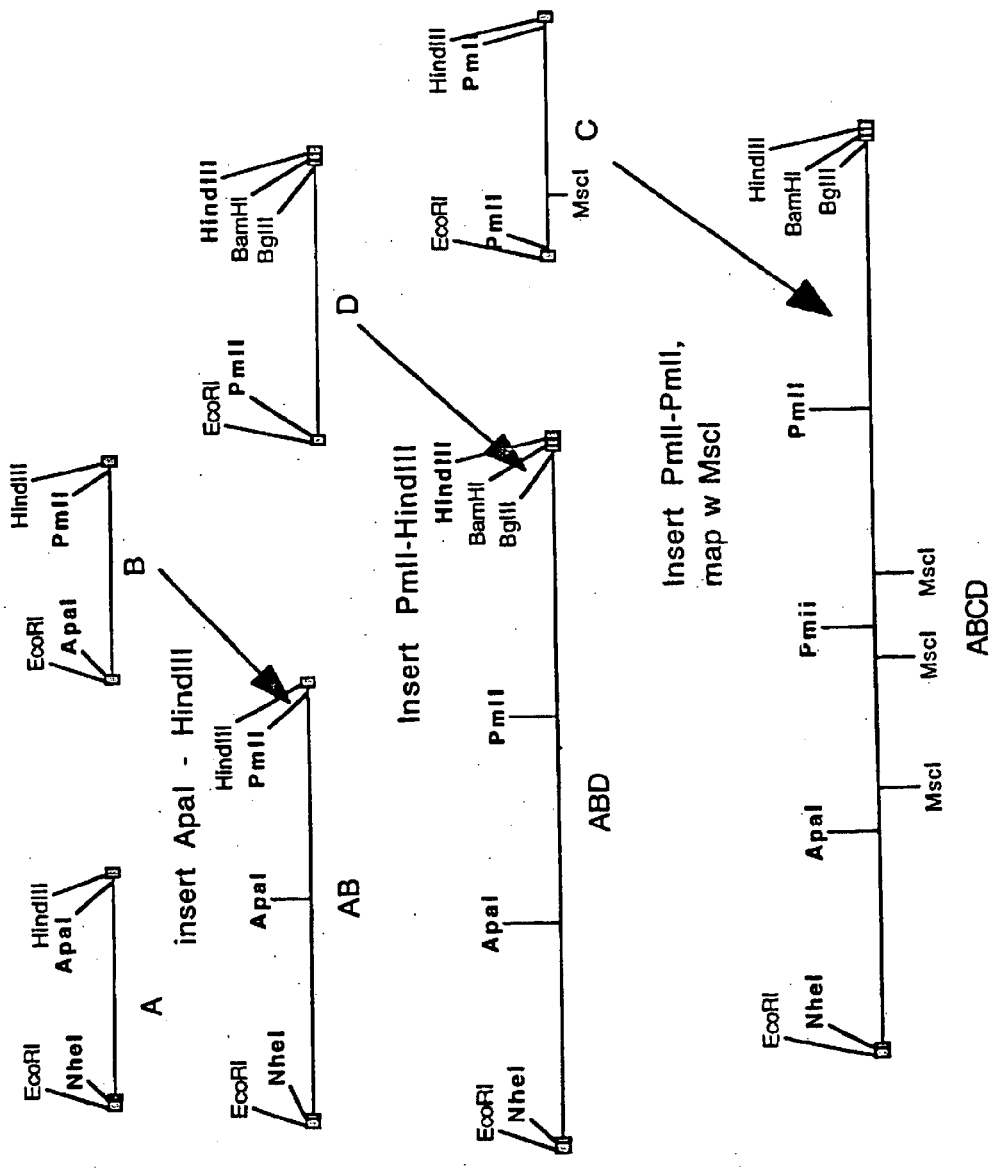
FIGS. 6A–6E, are a schematic representation of the assembly of pXF8.61.
Figure 6B:
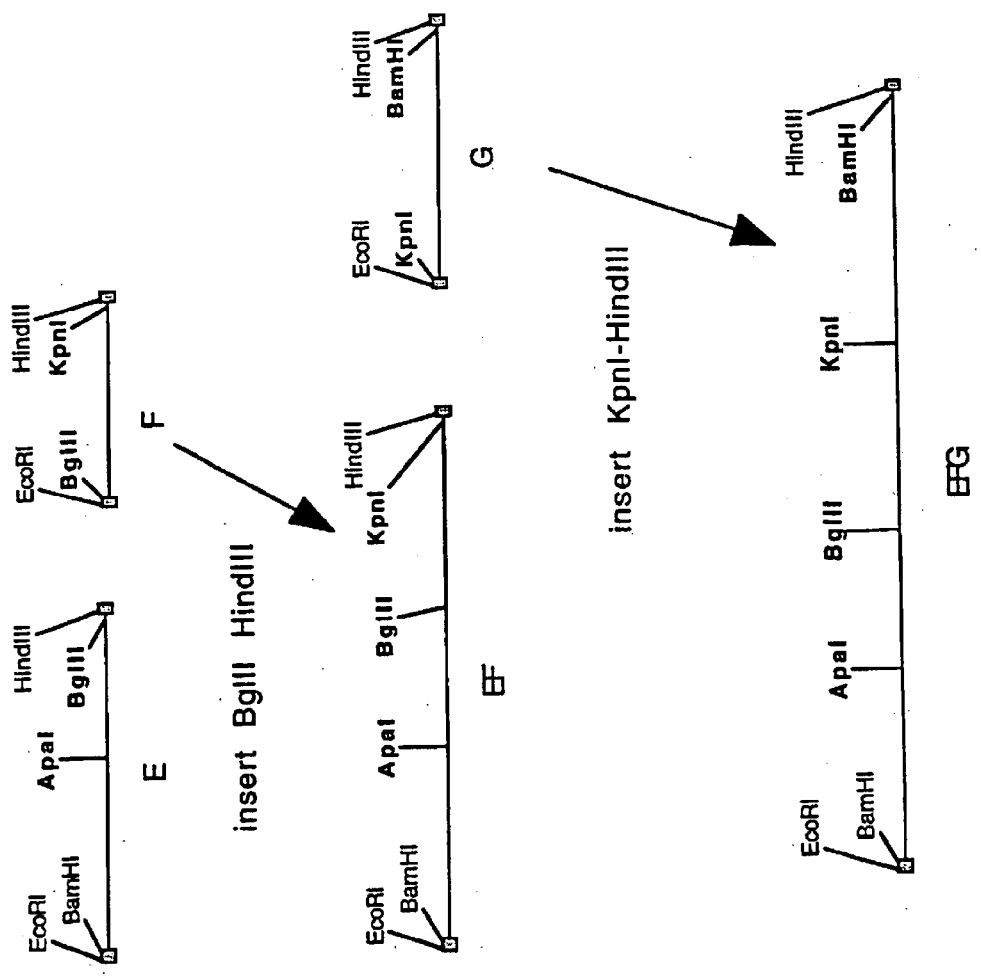
Figure 6C:
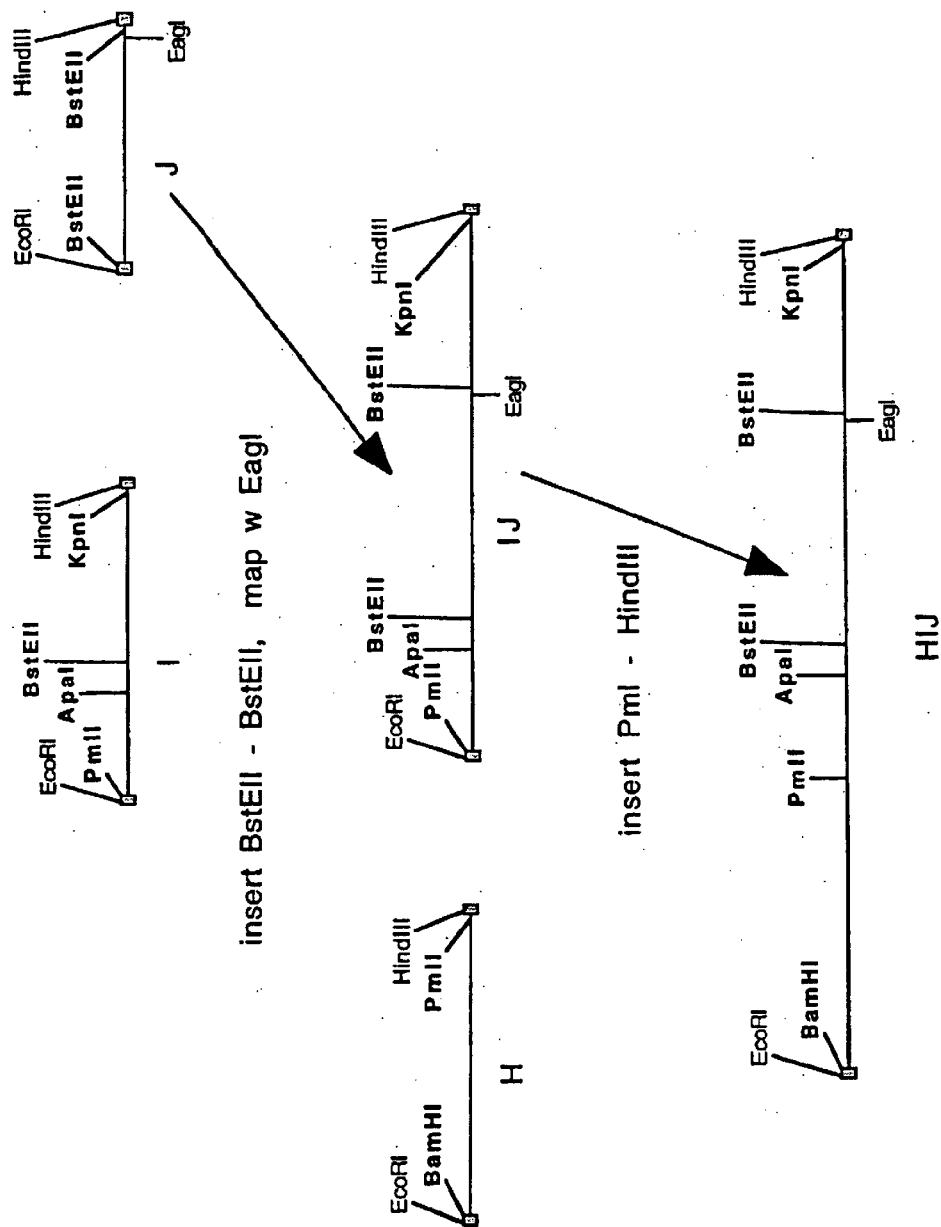
Figure 6D:
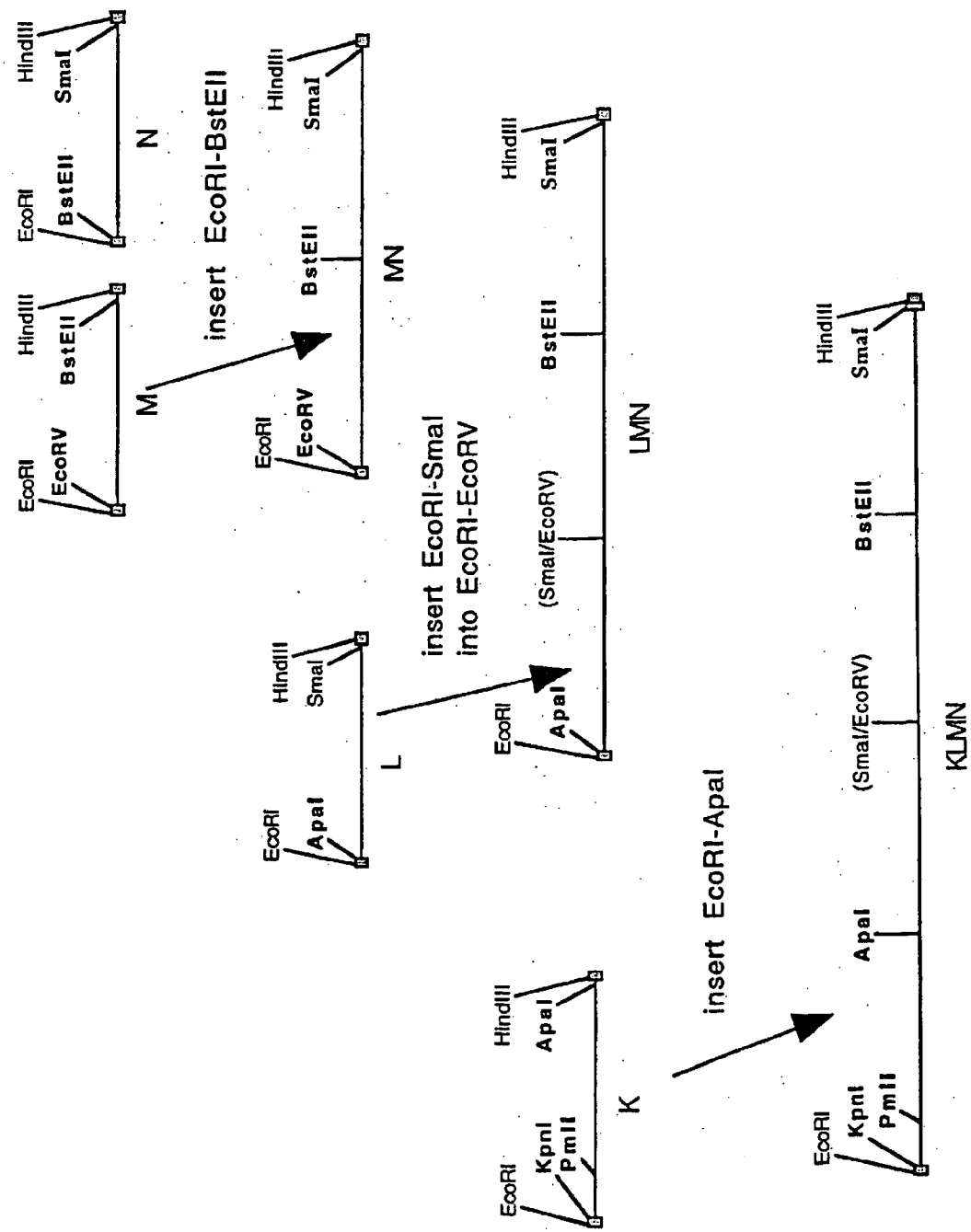
Figure 6E:
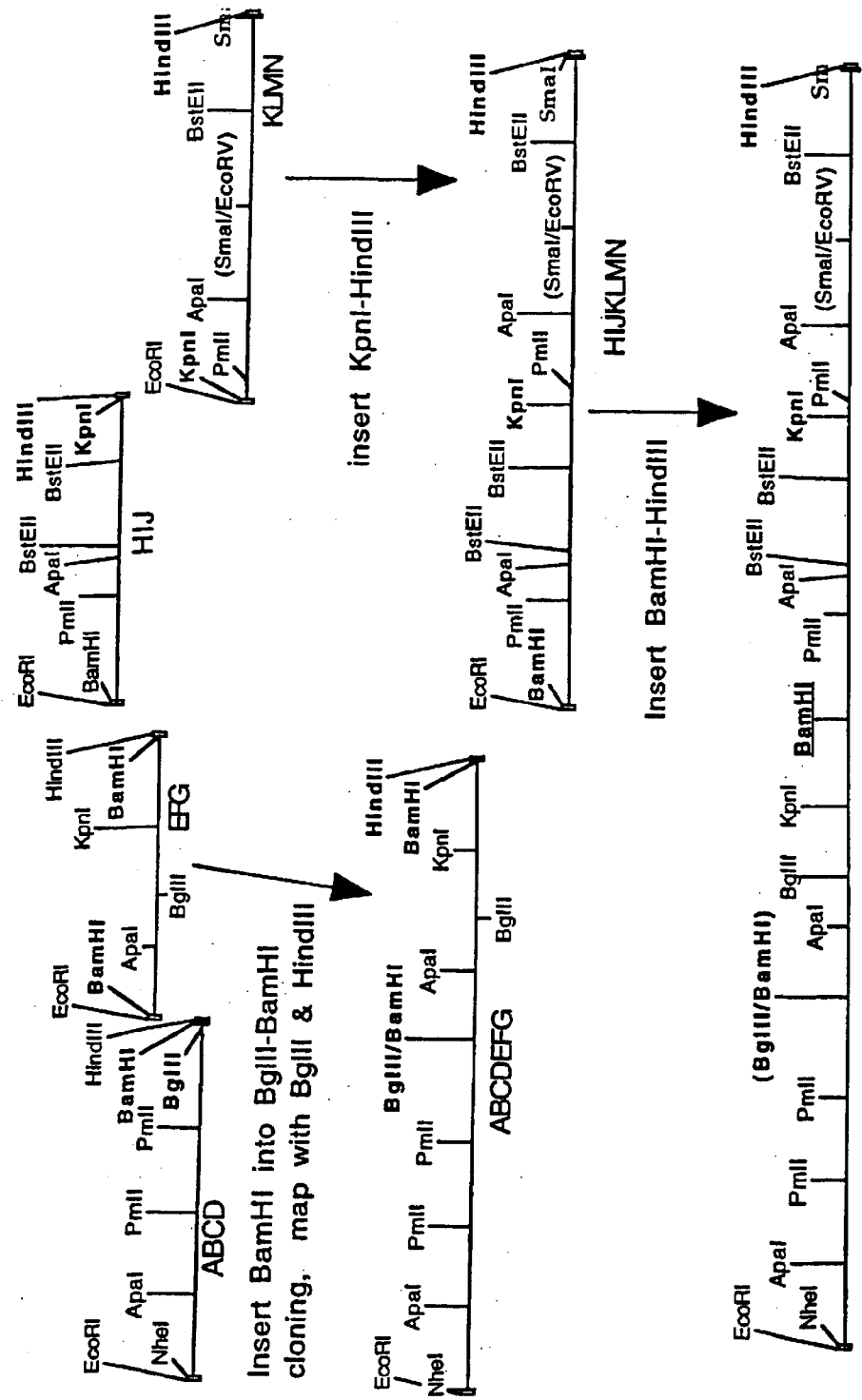

The fourteen gene fragments of the B-domain-deleted-FVIII optimized cDNA listed in Table 2 and shown in FIGS. 5A–5N (Fragment A-Fragment N) were made as follows. 92 oligonucleotides were made by oligonucleotide synthesis on an ABI 391 synthesizer (Perkin Elmer). The 92 oligonucleotides are listed in Table 3. FIGS. 5A–5N show how these 92 oligonucleotides anneal to form the fourteen gene fragments of Table 2. For each strand of each gene fragment, the first oligonucleotide (i.e. the most 5') was manufactured with a 5'-hydroxyl terminus, and the subsequent oligonucleotides were manufactured as 5'-phosphorylated to allow the ligation of adjacent annealed oligonucleotides. For gene fragments A,B,C,F,G,J,L,M and N, six oligonucleotides were annealed, ligated, digested with EcoRI and HindIII and cloned into pUC18 digested with EcoRI and HindIII. For gene fragments D, E, H and I, eight oligonucleotides were annealed, ligated, digested with EcoRI and HindIII and cloned into pUC18 digested with EcoRI and HindIII. This procedure generated fourteen different plasmids—pAM1A through pAM1N.

TABLE 2

| Fragment | 5' end | | 3' end | | Note |
|---|---|---|---|---|---|
| A | NheI | 1 | ApaI | 279 | |
| B | ApaI | 279 | PmlI | 544 | |
| C | PmlI | 544 | PmlI | 829 | |
| D | PmlI | 829 | BglII (/BamHI) | 1172 | BamHI site 3' to seq |
| E | (BglII/) BamHI | 1172 | BglII | 1583 | |
| F | BglII | 1583 | KpnI | 1817 | |
| G | KpnI | 1817 | BamHI | 2126 | |
| H | BamHI | 2126 | PmlI | 2491 | |
| I | PmlI | 2491 | BstEII | 3170 | ΔBstEII 2661–2955 |
| J | BstEII | 2661 | BstEII | 2955 | |
| K | KpnI | 3170 | ApaI | 3482 | |
| L | ApaI | 3482 | SmaI (/EcoRV) | 3772 | |
| M | (SmaI/) EcoRV | 3772 | BstEII | 4062 | |
| N | BstEII | 4062 | SmaI | 4348 | |

In Table 2 the restriction site positions are numbered by the first base of the palindrome; numbering begins at the NheI site.

TABLE 3

| Oligo' Name | Oligo' Length | Oligonucleotide Sequence |
|---|---|---|
| AM1Af1 | 118 | GTAGAATTCGTAGGCTAGCATGCAGATCGAGCTGAGCACCTGCTTCTTCCTGTGCCTGCTGCGCTTCTGCTTCAGCGCCACCCGCCGCTACTACCTGGGCGCCGTGGAGCTGAGCTGG (SEQ ID NO: 7) |
| AM1Af2 | 104 | GACTACATGCAGAGCGACCTGGGCGAGCTGCCCGTGGACGCCCGCTTCCCCCCCCGCGTGCCCAAGAGCTTCCCCTTCAACACCAGCGTGGTGTACAAGAAGAC (SEQ ID NO: 8) |
| AM1Af3 | 88 | CCTGTTCGTGGAGTTCACCGACCACCTGTTCAACATCGCCAAGCCCCGCCCCCCCTGGATGGGCCTGCTGGGCCCCTACAAGCTTTAC (SEQ ID NO: 9) |
| AM1Ar1 | 119 | GTAAAGCTTGTAGGGGCCCAGCAGGCCCATCCAGGGGGGGCGGGGCTTGGCGATGTTGAACAGGTGGTCGGTGAACTCCACGAACAGGGTCTTCTTGTACACCACGCTGGTGTTGAAGG (SEQ ID NO: 10) |
| AM1Ar2 | 107 | GGAAGCTCTTGGGCACGCGGGGGGGAAGCGGGCGTCCACGGGCAGCTCGCCCAGGTCGCTCTGCATGTAGTCCCAGCTCAGCTCCACGGCGCCCAGGTAGTAGCGG (SEQ ID NO: 11) |
| AM1Ar3 | 84 | CGGGTGGCGCTGAAGCAGAAGCGCAGCAGGCACAGGAAGAAGCAGGTGCTCAGCTCGATCTGCATGCTAGCCTACGAATTCTAC (SEQ ID NO: 12) |
| AM1Bf1 | 115 | GTAGAATTCGTAGGGGCCCCACCATCCAGGCCGAGGTGTACGACACCGTGGTGATCACCCTGAAGAACATGGCCAGCCACCCCGTGAGCCTGCACGCCGTGGGCGTGAGCTACTG (SEQ ID NO: 13) |
| AM1Bf2 | 103 | GAAGGCCAGCGAGGGCGCCGAGTACGACGACCAGACCAGCCAGCGCGAGAAGGAGGACGACAAGGTGTTCCCCGGCGGCAGCCACACCTACGTGTGGCAGGTG (SEQ ID NO: 14) |
| AM1Bf3 | 79 | CTGAAGGAGAACGGCCCCATGGCCAGCGACCCCCTGTGCCTGACCTACAGCTACCTGAGCCACGTGCTACAAGCTTTAC (SEQ ID NO: 15) |
| AM1Br1 | 107 | GTAAAGCTTGTAGCACGTGGCTCAGGTAGCTGTAGGTCAGGCACAGGGGGTCGCTGGCCATGGGGCCGTTCTCCTTCAGCACCTGCCACACGTAGGTGTGGCTGCCG(SEQ ID NO: 16) |
| AM1Br2 | 101 | CCGGGGAACACCTTGTCGTCCTCCTTCTCGCGCTGGCTGGTCTGGTCGTCGTACTCGGCGCCCTCGCTGGCCTTCCAGTAGCTCACGCCCACGGCGTGCAG (SEQ ID NO: 17) |
| AM1Br3 | 89 | GCTCACGGGGTGGCTGGCCATGTTCTTCAGGGTGATCACCACGGTGTCGTACACCTCGGCCTGGATGGTGGGGCCCCTACGAATTCTAC (SEQ ID NO: 18) |
| AM1Cf1 | 122 | GTAGAATTCGTAGCCACGTGGACCTGGTGAAGGACCTGAACAGCGGCCTGATCGGCGCCCTGCTGGTGTGCCGCGAGGGCAGCCTGGCCAAGGAGAAGACCCAGACCCTGCACAAGTTCATC (SEQ ID NO: 19) |
| AM1Cf2 | 110 | CTGCTGTTCGCCGTGTTCGACGAGGGCAAGAGCTGGCACAGCGAGACCAAGAACAGCCTGATGCAGGACCGCGACGCCGCCAGCGCCCGCGCCTGGCCCAAGATGCACAC (SEQ ID NO: 20) |
| AM1Cf3 | 86 | CGTGAACGGCTACGTGAACCGCAGCCTGCCCGGCCTGATCGGCTGCCACCGCAAGAGCGTGTACTGGCACGTGCTACAAGCTTTAC (SEQ ID NO: 21) |
| AM1Cr1 | 108 | GTAAAGCTTGTAGCACGTGCCAGTACACGCTCTTGCGGTGGCAGCCGATCAGGCCGGGCAGGCTGCGGTTCACGTAGCCGTTCACGGTGTGCATCTTGGGCCAGGCGC (SEQ ID NO: 22) |
| AM1Cr2 | 110 | GGGCGCTGGCGGCGTCGCGGTCCTGCATCAGGCTGTTCTTGGTCTCGCTGTGCCAGCTCTTGCCCTCGTCGAACACGGCGAACAGCAGGATGAACTTGTGCAGGGTCTGG (SEQ ID NO: 23) |
| AM1Cr3 | 100 | GTCTTCTCCTTGGCCAGGCTGCCCTCGCGGCACACCAGCAGGGCGCCGATCAGGCCGCTGTTCAGGTCCTTCACCAGGTCCACGTGGCTACGAATTCTAC (SEQ ID NO: 24) |
| AM1Df1 | 99 | GTAGAATTCGTAGCACGTGATCGGCATGGGCACCACCCCCGAGGTGCACGCATCTTCCTGGAGGGCCACACCTTCCTGGTGCGCAACCACCGCCAGGC (SEQ ID NO: 25) |
| AM1Df2 | 100 | CAGCCTGGAGATCAGCCCCATCACCTTCCTGACCGCCCAGACCCTGCTGATGGACCTGGGCCAGTTCCTGCTGTTCTGCCACATCAGCAGCCACCAGCAC (SEQ ID NO: 26) |
| AM1Df3 | 101 | GACGGCATGGAGGCCTACGTGAAGGTGGACAGCTGCCCCGAGGAGCCCCAGCTGCGCATGAAGAACAACGAGGAGGCCGAGGACTACGACGACGACCTGAC (SEQ ID NO: 27) |
| AM1Df4 | 84 | CGACAGCGAGATGGACGTGGTGCGCTTCGACGACGACAACAGCCCCAGCTTCATCCAGATCTCTACGGATCCTACAAGCTTTAC (SEQ ID NO: 28) |
| AM1Dr1 | 109 | GTAAAGCTTGTAGGATCCGTAGAGATCTGGATGAAGCTGGGGCTGTTGTCGTCGTCGAAGCGCACCACGTCCATCTCGCTGTCGGTCAGGTCGTCGTCGTAGTCCTCGG (SEQ ID NO: 29) |
| AM1Dr2 | 101 | CCTCCTCGTTGTTCTTCATGCGCAGCTGGGGCTCCTCGGGGCAGCTGTCCACCTTCACGTAGGCCTCCATGCCGTCGTGCTGGTGGCTGCTGATGTGGCAG (SEQ ID NO: 30) |
| AM1Dr3 | 102 | AACAGCAGGAACTGGCCCAGGTCCATCAGCAGGGTCTGGGCGGTCAGGAAGGTGATGGGGCTGATCTCCAGGCTGGCCTGGCGGTGGTTGCGCACCAGGAAG (SEQ ID NO: 31) |
| AM1Dr4 | 72 | GTGTGGCCCTCCAGGAAGATGCTGTGCACCTCGGGGGTGGTGCCCATGCCGATCACGTGCTACGAATTCTAC (SEQ ID NO: 32) |
| AM1Ef1 | 122 | GTAGAATTCGTAGGGATCCGCAGCGTGGCCAAGAAGCACCCCAAGACCTGGGTGCACTACATCGCCGCCGAGGAGGAGGACTGGGACTACGCCCCCCTGGTGCTGGCCCCCGACGACCGCAG (SEQ ID NO: 33) |
| AM1Ef2 | 120 | CTACAAGAGCCAGTACCTGAACAACGGCCCCAGCGCATCGGCCGCAAGTACAAGAAGGTGCGCTTCATGGCCTACACCGACGAGACCTTCAAGACCCGCGAGGCCATCCAGCACGAGAG (SEQ ID NO: 34) |
| AM1Ef3 | 115 | CGGCATCCTGGGCCCCCTGCTGTACGGCGAGGTGGGCGACACCCTGCTGATCATCTTCAAGAACCAGGCCAGCCGCCCCTACAACATCTACCCCCACGGCATCACCGACGTGCGC (SEQ ID NO: 35) |
| AM1Ef4 | 86 | CCCCTGTACAGCCGCCGCCTGCCCAAGGGCGTGAAGCACCTGAAGGACTTCCCCATCCTGCCCGGCGAGATCTCTACAAGCTTTAC (SEQ ID NO: 36) |
| AM1Er1 | 109 | GTAAAGCTTGTAGAGATCTCGCCGGGCAGGATGGGGAAGTCCTTCAGGTGCTTCACGCCCTTGGGCAGGCGGCGGCTGTACAGGGGGCGCACGTCGGTGATGCCGTGGG (SEQ ID NO: 37) |
| AM1Er2 | 114 | GGTAGATGTTGTAGGGGCGGCTGGCCTGGTTCTTGAAGATGATCAGCAGGGTGTCGCCCACCTCGCCGTACAGCAGGGGGCCCAGGATGCCGCTCTCGTGCTGGATGGCCTCGC (SEQ ID NO: 38) |
| AM1Er3 | 121 | GGGTCTTGAAGGTCTCGTCGGTGTAGGCCATGAAGCGCACCTTCTTGTACTTGCGGCCGATGCGCTGGGGGCCGTTGTTCAGGTACTGGCTCTTGTAGCTGCGGTCGTCGGGGGCCAGCAC (SEQ ID NO: 39) |

TABLE 3-continued

| Oligo' Name | Oligo' Length | Oligonucleotide Sequence |
|---|---|---|
| AM1Er4 | 99 | CAGGGGGGCGTAGTCCCAGTCCTCCTCCTCGGCGGCGATGTAGTGCACCCAGGTCTTGGG GTGCTTCTTGGCCACGCTGCGGATCCCTACGAATTCTAC (SEQ ID NO: 40) |
| AM1Ff1 | 102 | GTAGAATTCGTAGAGATCTTCAAGTACAAGTGGACCGTGACCGTGGAGGACGGCCCCAC CAAGAGCGACCCCCGCTGCCTGACCCGCTACTACAGCAGCTTC (SEQ ID NO: 41) |
| AM1Ff2 | 103 | GTGAACATGGAGCGCGACCTGGCCAGCGGCCTGATCGGCCCCCTGCTGATCTGCTACAAG GAGAGCGTGGACCAGCGCGGCAACCAGATCATGAGCGACAAGC (SEQ ID NO: 42) |
| AM1Ff3 | 61 | GCAACGTGATCCTGTTCAGCGTGTTCGACGAGAACCGCAGCTGGTACCCTACAAGCTTTA C (SEQ ID NO: 43) |
| AM1Fr1 | 87 | GTAAAGCTTGTAGGGTACCAGCTGCGGTTCTCGTCGAACACGCTGAACAGGATCACGTTG CGCTTGTCGCTCATGATCTGGTTGCCG (SEQ ID NO: 44) |
| AM1Fr2 | 101 | CGCTGGTCCACGCTCTCCTTGTAGCAGATCAGCAGGGGGCCGATCAGGCCGCTGGCCAGG TCGCGCTCCATGTTCACGAAGCTGCTGTAGTAGCGGGTCAG (SEQ ID NO: 45) |
| AM1Fr3 | 78 | GCAGCGGGGGTCGCTCTTGGTGGGGCCGTCCTCCACGGTCACGGTCCACTTGTACTTGAA GATCTCTACGAATTCTAC (SEQ ID NO: 46) |
| AM1Gf1 | 120 | GTAGAATTCGTAGGGTACCTGACCGAGAACATCCAGCGCTTCCTGCCCAACCCCGCCGGC GTGCAGCTGGAGGACCCCGAGTTCCAGGCCAGCAACATCATGCACAGCATCAACGGCTAC (SEQ ID NO: 47) |
| AM1Gf2 | 126 | GTGTTCGACAGCCTGCAGCTGAGCGTGTGCCTGCACGAGGTGGCCTACTGGTACATCCTG AGCATCGGCGCCCAGACCGACTTCCTGAGCGTGTTCTTCAGCGGCTACACCTTCAAGCACA AGATG (SEQ ID NO: 48) |
| AM1Gf3 | 95 | GTGTACGAGGACACCCTGACCCTGTTCCCCTTCAGCGGCGAGACCGTGTTCATGAGCATG GAGAACCCCGGCCTGTGGATCCCTACAAGCTTTAC (SEQ ID NO: 49) |
| AM1Gr1 | 119 | GTAAAGCTTGTAGGGATCCACAGGCCGGGGTTCTCCATGCTCATGAACACGGTCTCGCCG CTGAAGGGGAACAGGGTCAGGGTGTCCTCGTACACCATCTTGTGCTTGAAGGTGTAGCC (SEQ ID NO: 50) |
| AM1Gr2 | 124 | GCTGAAGAACACGCTCAGGAAGTCGGTCTGGGCGCCGATGCTCAGGATGTACCAGTAGG CCACCTCGTGCAGGCACACGCTCAGCTGCAGGCTGTCGAACACGTAGCCGTTGATGCTGTG CATG (SEQ ID NO: 51) |
| AM1Gr3 | 98 | ATGTTGCTGGCCTGGAACTCGGGGTCCTCCAGCTGCACGCCGGCGGGGTTGGGCAGGAA GCGCTGGATGTTCTCGGTCAGGTACCCTACGAATTCTAC (SEQ ID NO: 52) |
| AM1Hf1 | 111 | GTAGAATTCGTAGGGATCCTGGGCTGCCACAACAGCGACTTCCGCAACCGCGGCATGACC GCCCTGCTGAAGGTGAGCAGCTGCGACAAGAACACCGGCGACTACTACGAG (SEQ ID NO: 53) |
| AM1Hf2 | 102 | GACAGCTACGAGGACATCAGCGCCTACCTGCTGAGCAAGAACAACGCCATCGAGCCCCG CCTGGAGGAGATCACCCGCACCACCCTGCAGAGCGACCAGGAG (SEQ ID NO: 54) |
| AM1Hf3 | 105 | GAGATCGACTACGACGACACCATCAGCGTGGAGATGAAGAAGGAGGACTTCGACATCTA CGACGAGGACGAGAACCAGAGCCCCCGCAGCTTCCAGAAGAAGACC (SEQ ID NO: 55) |
| AM1Hf4 | 79 | CGCCACTACTTCATCGCCGCCGTGGAGCGCCTGTGGGACTACGGCATGAGCAGCAGCCCC CACGTGCTACAAGCTTTAC (SEQ ID NO: 56) |
| AM1Hr1 | 101 | GTAAAGCTTGTAGCACGTGGGGGCTGCTGCTCATGCCGTAGTCCCACAGGCGCTCCACGG CGGCGATGAAGTAGTGGCGGGTCTTCTTCTGGAAGCTGCGG (SEQ ID NO: 57) |
| AM1Hr2 | 105 | GGGCTCTGGTTCTCGTCCTCGTCGTAGATGTCGAAGTCCTCCTTCTTCATCTCCACGCTGA TGGTGTCGTCGTAGTCGATCTCCTCCTGGTCGCTCTGCAGGGTG (SEQ ID NO: 58) |
| AM1Hr3 | 108 | GTGCGGGTGATCTCCTCCAGGCGGGGCTCGATGGCGTTGTTCTTGCTCAGCAGGTAGGCG CTGATGTCCTCGTAGCTGTCCTCGTAGTAGTCGCCGGTGTTCTTGTCG (SEQ ID NO: 59) |
| AM1Hr4 | 83 | CAGCTGCTCACCTTCAGCAGGGCGGTCATGCCGCGGTTGCGGAAGTCGCTGTTGTGGCAG CCCAGGATCCCTACGAATTCTAC (SEQ ID NO: 60) |
| AM1If1 | 115 | GTAGAATTCGTAGCACGTGCTGCGCAACCGCGCCCAGAGCGGCAGCGTGCCCCAGTTCA AGAAGGTGGTGTTCCAGGAGTTCACCGACGGCAGCTTCACCCAGCCCCTGTACCGC (SEQ ID NO: 61) |
| AM1If2 | 111 | GGCGAGCTGAACGAGCACCTGGGCCTGCTGGGCCCCTACATCCGCGCCGAGGTGGAGGA CAACATCATGGTGACCGTGCAGGAGTTCGCCCTGTTCTTCACCATCTTCGAC (SEQ ID NO: 62) |
| AM1If3 | 106 | GAGACCAAGAGCTGGTACTTCACCGAGAACATGGAGCGCAACTGCCGCGCCCCCTGCAA CATCCAGATGGAGGACCCCACCTTCAAGGAGAACTACCGCTTCCACG (SEQ ID NO: 63) |
| AM1If4 | 85 | CCATCAACGGCTACATCATGGACACCCTGCCCGGCCTGGTGATGGCCCAGGACCAGCGCA TCCGCTGGTACCCTACAAGCTTTAC (SEQ ID NO: 64) |
| AM1Ir1 | 115 | GTAAAGCTTGTAGGGTACCAGCGGATGCGCTGGTCCTGGGCCATCACCAGGCCGGGCAG GGTGTCCATGATGTAGCCGTTGATGGCGTGGAAGCGGTAGTTCTCCTTGAAGGTGG (SEQ ID NO: 65) |
| AM1Ir2 | 99 | GGTCCTCCATCTGGATGTTGCAGGGGGCGCGGCAGTTGCGCTCCATGTTCTCGGTGAAGT ACCAGCTCTTGGTCTCGTCGAAGATGGTGAAGAACAGGG (SEQ ID NO: 66) |
| AM1Ir3 | 110 | CGAACTCCTGCACGGTCACCATGATGTTGTCCTCCACCTCGGCGCGGATGTAGGGGCCCA GCAGGCCCAGGTGCTCGTTCAGCTCGCCGCGGTACAGGGGCTGGGTGAAG (SEQ ID NO: 67) |
| AM1Ir4 | 93 | CTGCCGTCGGTGAACTCCTGGAACACCACCTTCTTGAACTGGGGCACGCTGCCGCTCTGG GCGCGGTTGCGCAGCACGTGCTACGAATTCTAC (SEQ ID NO: 68) |
| AM1Jf1 | 116 | GTAGAATTCGTAGGGTGACCTTCCGCAACCAGGCCAGCCGCCCCTACAGCTTCTACAGCA GCCTGATCAGCTACGAGGAGGACCAGCGCCAGGGCGCCGAGCCCCGCAAGAACTTC (SEQ ID NO: 69) |
| AM1Jf2 | 120 | GTGAAGCCCAACGAGACCAAGACCTACTTCTGGAAGGTGCAGCACCACATGGCCCCCAC CAAGGACGAGTTCGACTGCAAGGCCTGGGCCTACTTCAGCGACGTGGACCTGGAGAAGGA C (SEQ ID NO: 70) |
| AM1Jf3 | 91 | GTGCACAGCGGCCTGATCGGCCCCCTGCTGGTGTGCCACACCAACACCCTGAACCCCGCC CACGGCCGCCAGGTGACCCTACAAGCTTAC (SEQ ID NO: 71) |

TABLE 3-continued

| Oligo' Name | Oligo' Length | Oligonucleotide Sequence |
| --- | --- | --- |
| AM1Jr1 | 113 | GTAAAGCTTGTAGGGTCACCTGGCGGCCGTGGGCGGGGTTCAGGGTGTTGGTGTGGCACA CCAGCAGGGGGCCGATCAGGCCGCTGTGCACGTCCTTCTCCAGGTCCACGTCG (SEQ ID NO: 72) |
| AM1Jr2 | 121 | CTGAAGTAGGCCCAGGCCTTGCAGTCGAACTCGTCCTTGGTGGGGGCCATGTGGTGCTGC ACCTTCCAGAAGTAGGTCTTGGTCTCGTTGGGCTTCACGAAGTTCTTGCGGGGCTCGGCGC (SEQ ID NO: 73) |
| AM1Jr3 | 93 | CCTGGCGCTGGTCCTCCTCGTAGCTGATCAGGCTGCTGTAGAAGCTGTAGGGGCGGCTGG CCTGGTTGCGGAAGGTCACCCTACGAATTCTAC (SEQ ID NO: 74) |
| AM1Kf1 | 120 | GTAGAATTCGTAGGGTACCTGCTGAGCATGGGCAGCAACGAGAACATCCACAGCATCCA CTTCAGCGGCCACGTGTTCACCGTGCGCAAGAAGGAGGAGTACAAGATGGCCCTGTACAAC (SEQ ID NO: 75) |
| AM1Kf2 | 122 | CTGTACCCCGGCGTGTTCGAGACCGTGGAGATGCTGCCCAGCAAGGCCGGCATCTGGCGC GTGGAGTGCCTGATCGGCGAGCACCTGCACGCCGGCATGAGCACCCTGTTCCTGGTGTACA G (SEQ ID NO: 76) |
| AM1Kf3 | 102 | CAACAAGTGCCAGACCCCCCTGGGCATGGCCAGCGGCCACATCCGCGACTTCCAGATCAC CGCCAGCGGCCAGTACGGCCAGTGGGCCCCTACAAGCTTTAC (SEQ ID NO: 77) |
| AM1Kr1 | 123 | GTAAAGCTTGTAGGGGCCCACTGGCCGTACTGGCCGCTGGCGGTGATCTGGAAGTCGCGG ATGTGGCCGCTGGCCATGCCCAGGGGGGTCTGGCACTTGTTGCTGTACACCAGGAACAGGG TG (SEQ ID NO: 78) |
| AM1Kr2 | 125 | CTCATGCCGGCGTGCAGGTGCTCGCCGATCAGGCACTCCACGCGCCAGATGCCGGCCTTG CTGGGCAGCATCTCCACGGTCTCGAACACGCCGGGGTACAGGTTGTACAGGGCCATCTTGT ACTC (SEQ ID NO: 79) |
| AM1Kr3 | 96 | CTCCTTCTTGCGCACGGTGAACACGTGGCCGCTGAAGTGGATGCTGTGGATGTTCTCGTT GCTGCCCATGCTCAGCAGGTACCCTACGAATTCTAC (SEQ ID NO: 80) |
| AM1Lf1 | 120 | GTAGAATTCGTAGGGGCCCCCAAGCTGGCCCGCCTGCACTACAGCGGCAGCATCAACGC CTGGAGCACCAAGGAGCCCTTCAGCTGGATCAAGGTGGACCTGCTGGCCCCCATGATCATC (SEQ ID NO: 81) |
| AM1Lf2 | 116 | CACGGCATCAAGACCCAGGGCGCCCGCCAGAAGTTCAGCAGCCTGTACATCAGCCAGTT CATCATCATGTACAGCCTGGACGGCAAGAAGTGGCAGACCTACCGCGGCAACAGCAC (SEQ ID NO: 82) |
| AM1Lf3 | 86 | CGGCACCCTGATGGTGTTCTTCGGCAACGTGGACAGCAGCGGCATCAAGCACAACATCTT CAACCCCCCCGGGCTACAAGCTTTAC (SEQ ID NO: 83) |
| AM1Lr1 | 110 | GTAAAGCTTGTAGCCCGGGGGGGTTGAAGATGTTGTGCTTGATGCCGCTGCTGTCCACGT TGCCGAAGAACACCATCAGGGTGCCGGTGCTGTTGCCGCGGTAGGTCTGC (SEQ ID NO: 84) |
| AM1Lr2 | 113 | CACTTCTTGCCGTCCAGGCTGTACATGATGATGAACTGGCTGATGTACAGGCTGCTGAAC TTCTGGCGGGCGCCCTGGGTCTTGATGCCGTGGATGATCATGGGGGCCAGCAG (SEQ ID NO: 85) |
| AM1Lr3 | 99 | GTCCACCTTGATCCAGCTGAAGGGCTCCTTGGTGCTCCAGGCGTTGATGCTGCCGCTGTA GTGCAGGCGGGCCAGCTTGGGGGCCCCTACGAATTCTAC (SEQ ID NO: 86) |
| AM1Mf1 | 122 | GTAGAATTCGTAGGATATCATCGCCCGCTACATCCGCCTGCACCCCACCCACTACAGCAT CCGCAGCACCCTGCGCATGGAGCTGATGGGCTGCGACCTGAACAGCTGCAGCATGCCCCTG G (SEQ ID NO: 87) |
| AM1Mf2 | 112 | GCATGGAGAGCAAGGCCATCAGCGACGCCCAGATCACCGCCAGCAGCTACTTCACCAAC ATGTTCGCCACCTGGAGCCCCAGCAAGGCCCGCCTGCACCTGCAGGGCCGCAG (SEQ ID NO: 88) |
| AM1Mf3 | 89 | CAACGCCTGGCGCCCCCAGGTGAACAACCCCAAGGAGTGGCTGCAGGTGGACTTCCAGA AGACCATGAAGGTGACCCTACAAGCTTTAC (SEQ ID NO: 89) |
| AM1Mr1 | 112 | GTAAAGCTTGTAGGGTCACCTTCATGGTCTTCTGGAAGTCCACCTGCAGCCACTCCTTGG GGTTGTTCACCTGGGGGCGCCAGGCGTTGCTGCGGCCCTGCAGGTGCAGGCG (SEQ ID NO: 90) |
| AM1Mr2 | 114 | GGCCTTGCTGGGGCTCCAGGTGGCGAACATGTTGGTGAAGTAGCTGCTGGCGGTGATCTG GGCGTCGCTGATGGCCTTGCTCTCCATGCCCAGGGGCATGCTGCAGCTGTTCAG (SEQ ID NO: 91) |
| AM1Mr3 | 97 | GTCGCAGCCCATCAGCTCCATGCGCAGGGTGCTGCGGATGCTGTAGTGGGTGGGGTGCAG GCGGATGTAGCGGGCGATGATATCCTACGAATTCTAC (SEQ ID NO: 92) |
| AM1Nf1 | 122 | GTAGAATTCGTAGGGTGACCGGCGTGACCACCCAGGGCGTGAAGAGCCTGCTGACCAGC ATGTACGTGAAGGAGTTCCTGATCAGCAGCAGCCAGGACGGCCACCAGTGGACCCTGTTCT TC (SEQ ID NO: 93) |
| AM1Nf2 | 104 | CAGAACGGCAAGGTGAAGGTGTTCCAGGGCAACCAGGACAGCTTCACCCCCGTGGTGAA CAGCCTGGACCCCCCCCTGCTGACCCGCTACCTGCGCATCCACCC (SEQ ID NO: 94) |
| AM1Nf3 | 92 | CCAGAGCTGGGTGCACCAGATCGCCCTGCGCATGGAGGTGCTGGGCTGCGAGGCCCAGG ACCTGTACTAGCTGCCCGGGCTACAAGCTTTAC (SEQ ID NO: 95) |
| AM1Nr1 | 118 | GTAAAGCTTGTAGCCCGGGCAGCTAGTACAGGTCCTGGGCCTCGCAGCCCAGCACCTCCA TGCGCAGGGCGATCTGGTGCACCCAGCTCTGGGGGTGGATGCGCAGGTAGCGGGTCAG (SEQ ID NO: 96) |
| AM1Nr2 | 100 | CAGGGGGGGGTCCAGGCTGTTCACCACGGGGGTGAAGCTGTCCTGGTTGCCCTGGAACA CCTTCACCTTGCCGTTCTGGAAGAACAGGGTCCACTGGTGG (SEQ ID NO: 97) |
| AM1Nr3 | 100 | CCGTCCTGGCTGCTGCTGATCAGGAACTCCTTCACGTACATGCTGGTCAGCAGGCTCTTCA CGCCCTGGGTGGTCACGCCGGTCACCCTACGAATTCTAC (SEQ ID NO: 98) |

As noted in Table 2 and shown in FIGS. 5A–5N, fragment D was constructed with a Banc restriction site placed between the BglII site and the HindIII site at the 3' end of the fragment. Fragment I was constructed to carry the DNA from PmlI (2491) to BstEII (2661) followed immediately by the DNA from BstEII (2955) to KpnI (3170), so that the insertion of the BstEII fragment from pAMJ into the BstEII site of pAMI in the correct orientation will generate the desired sequences from 2491 to 3170. Plasmid pAM1B was digested with ApaI and HindIII and the insert was purified by agarose gel electrophoresis and inserted into plasmid pAM1A digested with ApaI and HindIII, generating plasmid pAM1AB. Plasmid pAM1D was digested with PmlI and HindIII and the insert was purified by agarose gel electrophoresis and inserted into plasmid pAM1AB digested with PmlI and HindIII, generating plasmid pAM1ABD. Plasmid pAM1C was digested with PmlI and the insert was purified by agarose gel electrophoresis and inserted into plasmid pAM1ABD digested with PmlI, generating plasmid pAM1ABCD, insert orientation was confirmed by the appearance of a diagnostic 111 bp fragment when digested with MscI. Plasmid pAM1F was digested with BglII and HindIII and the insert was purified by agarose gel electrophoresis and inserted into plasmid pAM1E digested with BglII and HindIII, generating plasmid pAM1EF. Plasmid pAM1G was digested with KpnI and HindIII and the insert was purified by agarose gel electrophoresis and inserted into plasmid pAM1EF digested with KpnI and HindIII, generating plasmid pAM1EFG. Plasmid pAM1J was digested with BstEII and the insert was purified by agarose gel electrophoresis and inserted into plasmid pAM1I digested with BstEII, generating plasmid pAM1IJ; orientation was confirmed by the appearance of a diagnostic 465 bp fragment when digested with EcoRI and EagI. Plasmid pAM1IJ was digested with PmlI and HindIII and the insert was purified by agarose gel electrophoresis and inserted into plasmid pAM1H digested with PmlI and HindIII, generating plasmid pAM1HIJ. Plasmid pAM1M was digested with EcoRI and BstEII and the insert was purified by agarose gel electrophoresis and inserted into plasmid pAM1N digested with EcoRI and BstEII, generating plasmid pAM1MN. Plasmid pAM1L was digested with EcoRI and SmaI and the insert was purified by agarose get electrophoresis and inserted into plasmid pAM1MN digested with EcoRI and EcoRV, generating plasmid pAM1LMN. Plasmid pAM1LMN was digested with ApaI and HindIII and the insert was purified by agarose gel electrophoresis and inserted into plasmid pAM1K digested with ApaI and HindIII, generating plasmid pAM1KLMN. Plasmid pAM1EFG was digested with BamHI and the insert was purified by agarose gel electrophoresis and inserted into plasmid pAM1ABCD digested with BamHI and BglII, generating plasmid pAM1ABCDEFG; orientation was confirmed by the appearance of a diagnostic 552 bp fragment when digested with BglII and HindIII. Plasmid pAM1KLMN was digested with KpnI and HindIII and the insert was purified by agarose gel electrophoresis and inserted into plasmid pAM1HIJ digested with KpnI and HindIII, generating plasmid pAM1HIJKLMN. Plasmid pAM1HIJKLMN was digested with BamHI and HindIII and the insert was purified by agarose gel electrophoresis and inserted into plasmid pAM1ABCDEFG digested with BamHI and HindIII, generating plasmid pAM1-1. These cloning steps are depicted in FIGS. 6A–6E. FIGS. 7A–7C shows the DNA sequence of the insert contained in pAM1-1 (SEQ ID NO:1). This insert can be cloned into any suitable expression vector as a NheI-SmaI fragment to generate an expression construct pXF8.61 (FIG. 4), pXF8.38 (FIG. 11) and pXF8.224 (FIG. 13) are examples of such a construct.

Construction of pXF8.186

Figure 8:
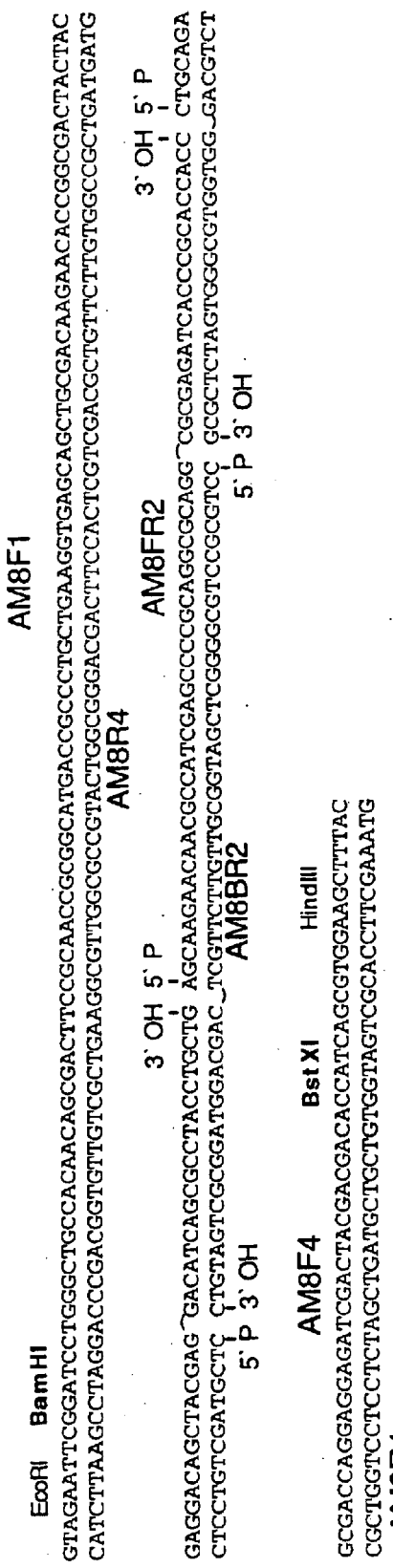
FIG. 8 is a schematic representation of the fragments assembled to construct pXF8.186.

The "LE" version of the B-domain-deleted-FVIII optimized cDNA contained in pAM1-1 was modified by replacing the Leu-Glu dipeptide (2284–2289) at the junction of the heavy and light chains with four Arginine residues, making a total of five consecutive Arginine residues (SEQ ID NO:2). This was achieved as follows. The six oligonucleotides shown in Table 4 were annealed, ligated, digested with EcoRI and HindIII and cloned into pUC 18 digested with EcoRI and HindIII, generating the plasmid pAM8B. FIG. 8 shows how these oligonucleotides anneal to form the requisite DNA sequence. pAM8B was digested with BamHI and BstXI and the 230 bp insert was purified by agarose gel electrophoresis and used to replace the BamHI(2126)–BstXI (2352) fragment of the "LE" version (See FIGS. 7A–7C). FIGS. 9A–9C shows the sequence of the resulting cDNA (SEQ ID NO:2). This "SArg" version of the B-domain-deleted-FVIII optimized cDNA can be cloned into any suitable expression vector as a NheI-SmaI fragment to generate an expression construct. pXF8.186 (FIG. 3) is an example of such a construct.

TABLE 4

| OLIGO' NAME | OLIGO' LENGTH | OLIGONUCLEOTIDE SEQUENCE |
|---|---|---|
| AM8F1 | 140 | GTAGAATTCGGATCCTGGGCTGCCACAACAGCGACTT CCGCAACCGCGGCATGACCGCCCTGCTGAAGGTGAGC AGCTGCGACAAGAACACCGGCGACTACTACGAGGAC AGCTACGAGGACATCAGCGCCTACCTGCTG (SEQ ID NO:99) |
| AM8BF2 | 57 | AGCAAGAACAACGCCATCGAGCCCCGCAGGCGCAGG CGCGAGATCACCCGCACCACC (SEQ ID NO:100) |
| AM8F4 | 58 | CTGCAGAGCGACCAGGAGGAGATCGACTACGACGAC ACCATCAGCGTGGAAGCTTTAC (SEQ ID NO:101) |
| AM8R1 | 79 | GTAAAGCTTCCACGCTGATGGTGTCGTCGTAGTCGAT CTCCTCCTGGTCGCTCTGCAGGGTGGTGCGGGTGATCT CGCG (SEQ ID NO:102) |
| AM8BR2 | 57 | CCTGCGCCTGCGGGGCTCGATGGCGTTGTTCTTGCTCA GCAGGTAGGCGCTGATGTC (SEQ ID NO:103) |

TABLE 4-continued

| OLIGO' NAME | OLIGO' LENGTH | OLIGONUCLEOTIDE SEQUENCE |
|---|---|---|
| AM8BR4 | 119 | CTCGTAGCTGTCCTCGTAGTAGTCGCCGGTGTTCTTGT CGCAGCTGCTCACCTTCAGCAGGGCGGTCATGCCGCG GTTGCGGAAGTCGCTGTTGTGGCAGCCCAGGATCCGA ATTCTAC (SEQ ID NO: 104) |

Construction of pXF8.36

The construct for expression of human Factor VIII, pXF8.36 (FIG. 10) is an 11.1 kilobase circular DNA plasmid which contains the following elements: A cytomegalovirus immediate early I gene (CMV) 5' flanking region comprised of a promoter sequence, a 5' untranslated sequence (5'UTS) and first intron sequence for initiation of transcription of the Factor VIII cDNA. The CMV region is next fused with a wild-type B domain-deleted Factor VIII cDNA sequence. The Factor VIII cDNA sequence is fused, at the 3' end, with a 0.3 kb fragment of the human growth hormone 3' untranslated sequence. A transcription termination signal and 3' untranslated sequence (3'UTS) of the human growth hormone gene is used to ensure processing of the message immediately following the stop codon. A selectable marker gene (the bacterial neomycin phosphotransferase (neo) gene) is inserted downstream of the Factor VIII cDNA to allow selection for stably transfected mammalian cells using the neomycin analog G418. Expression of the neo gene is under the control of the simian virus 40 (SV40) early promoter. The pUC 19-based amplicon carrying the pBR322-derived-α-lactamase (amp) and origin of replication (ori) allows for the uptake, selection and propagation of the plasmid in *E coli* K-12 strains. This region was derived from the plasmid pBSII SK+.

Construction of pXF8.38

The construct for expression of human Factor VIII, pXF8.38 (FIG. 11) is an 11.1 kilobase circular DNA plasmid which contains the following elements: A cytomegalovirus immediate early I gene (CMV) 5' flanking region comprised of a promoter sequence, 5' untranslated sequence (5'UTS) and first intron sequence for initiation of transcription of the Factor VIII cDNA. The CMV region is next fused with a synthetic, optimally configured B domain-deleted Factor VIII cDNA sequence. The Factor VIII cDNA sequence is fused, at the 3' end, with a 0.3 kb fragment of the human growth hormone 3' untranslated sequence. A transcription termination signal and 3' untranslated sequence (3'UTS) of the human growth hormone gene is used to ensure processing of the message immediately following the stop codon. A selectable marker gene (the bacterial neomycin phosphotransferase (neo) gene) to allow selection for stably transfected mammalian cells using the neomycin analog G418 is inserted downstream of the Factor VIII cDNA. Expression of the neo gene is under the control of the simian virus 40 (SV40) early promoter. The pUC 19-based amplicon carrying the pBR322-derived β-lactamase (amp) and origin of replication (ori) allows for the uptake, selection and propagation of the plasmid in *E coli* K-12 strains. This region was derived from the plasmid pBSII SK+.

pXF8.269 Construct

The construct for expression of human Factor VIII (FIG. 12), pXF8.269, is a 14.8 kilobase (kb) circular DNA plasmid which contains the following elements: A human collagen (I) α 2 promoter which contains 0.17 kb of 5' untranslated sequence (5'UTS), Aldolase A gene 5' untranslated sequence (5'UTS) and first intron sequence for initiation of transcription of the Factor VIII cDNA. The aldolase intron region is next fused with a synthetic, wild-type B domain-deleted Factor VIII cDNA sequence. A transcription termination signal and 3' untranslated sequence (3'UTS) of the human growth hormone gene to ensure processing of the message immediately following the stop codon. A selectable marker gene (the bacterial neomycin phosphotransferase (neo) gene) to allow selection for stably transfected mammalian cells using the neomycin analog G418 is inserted downstream of the Factor VIII cDNA. The expression of the neo gene is under the control of the SV40 promoter The pUC 19-based amplicon carrying the pBR322-derived β-lactamase (amp) and origin of replication (ori) allows for the uptake, selection and propagation of the plasmid in *E coli* K-12 strains. This region was derived from the plasmid pBSII SK+.

pXF8.224 Construct

The construct for expression of human Factor VIII, pXF8.224 (FIG. 13), is a 14.8 kilobase (kb) circular DNA plasmid which contains the following elements: A human collagen (I) α 2 promoter which contains 0.17 kb of 5' untranslated sequence (5'UTS), aldolase A gene 5' untranslated sequence (5'UTS) and first intron sequence for initiation of transcription of the Factor VIII cDNA. The aldolase intron region is next fused with a synthetic, optimally configured B domain-deleted Factor VIII cDNA sequence. A transcription termination signal and 3' untranslated sequence (3'UTS) of the human growth hormone gene is used to ensure processing of the message immediately following the stop codon. A selectable marker gene (the bacterial neomycin phosphotransferase (neo) gene) to allow selection for stably transfected mammalian cells using the neomycin analog G418 is inserted downstream of the Factor VIII cDNA. The expression of the neo gene is under the control of the SV40 promoter The pUC 19-based amplicon carrying the pBR322-derived-β-lactamase (amp) and origin of replication (ori) allows for the uptake, selection and propagation of the plasmid in *E coli* K-12 strains. This region was derived from the plasmid pBSII SK+.

Clotting Assay

A clotting assay based on an activated partial thromboplastin time (aPTT) (Proctor, et al., *Am. J. Clin. Path.*, 36:212–219, (1961)) was performed to analyze the biological activity of the BDD hFVIII molecules expressed by constructs in which BDD-FVIII coding region was optimized.

Biological Activity as Analyzed Using the Clotting Assay

The results of the aPTT-based clotting assay are presented in Table 5, below. Specific activity of the hFVIII preparations is presented as aPTT units per milligram hFVIII protein as determined by ELISA. Both of the human fibroblast-derived BDD hFVIII molecules (5R and LE) have high specific activity when measured the aPTT clotting assay. These specific activities have been determined to be up to 2- to 3-fold higher than those determined for CHO cell-derived full-length FVIII (as shown in Table 5). An average of multiple determinations of specific activities for various partially purified preparations of 5R and LE BDD hFVIII also shows consistently higher values for the BDD hFVIII molecules (11,622 Units/mg for 5R BDD hFVIII, and 14,561 Units/mg for LE BDD hFVIII as compared to 7097 Units/mg for full-length CHO cell-derived FVIII). An increased rate and/or extent of thrombin activation has been observed for various~BDD hFVIII molecules, possibly due to an effect of the B-domain to protect the heavy and light chains from thrombin cleavage and activation (Eaton et al., *Biochemistry*, 25:8343–8347, (1986), Meulien et al., *Protein Engineering*, 2:301–306, (1988)).

TABLE 5

Specific Activities of Various hFVIII Proteins

| hFVII Product | Concentration by ELISA (mg/mL) | aPTT Activity (aPTT U/mL) | Specific Activity (aPTT U/mg) |
|---|---|---|---|
| 5R BDD hFVIII | 0.050 | 1306 | 26,120 |
| LEBDD HFVIII | 0.124 | 2908 | 23,452 |
| Full-length (CHO-derived) FVIII | 0.158 | 1454 | 9202 |

Assay for Human Factor VIII in Transfected Cell Culture Supernatants.

Samples of cell culture, supernatants having cells transfected with wild-type, or optimized human BDD-human Factor VIII were assayed for human Factor VIII(hFVIII) content by using an enzyme-linked immunosorbent assay (ELISA). This assay is based on the use of two non-crossreacting monoclonal antibodies (mAb) in conjunction with samples consisting of cell culture media collected from the supernatants of transfected human fibroblast cells. Methods of transfection and identification of positively transfected cells are described in the U.S. Pat. No. 5,641,670, which is incorporated herein by reference.

TABLE 6

| Plasmid | Promoter/5' Untranslated sequence | Factor VIII cDNA Composition | Mean (FVIII mU/$10^6$ Cells/24 hr.) | Maximum (FVIII mU/$10^6$ Cells/24 hr.) | Number of Strains | Fold Increase |
|---|---|---|---|---|---|---|
| pXF8.36 | CMV IE1 | Wild Type | 567 | 2557 | 38 | — |
| pXF8.38 | CMV IE1 | Optimal Configuration | 5403 | 17106 | 24 | 9.5X |
| pXF8.269 | Collagen I□2/Aldolase Intron | Wild Type | 382 | 1227 | 18 | — |
| pXF8.224 | Collagen I□2/Aldolase Intron | Optimal Configuration | 2022 | 11930 | 218 | 5.3X |

ELISA units based on standard curves prepared from pooled normal plasma.

All patents and other references cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A synthetic nucleic acid sequence which encodes a human Factor VIII or, wherein at least one non-common codon or less-common codon has been replaced by a common codon encoding the same amino acid residue as the non-common or less-common codon and wherein the synthetic nucleic acid has a continuous stretch of at least 150 codons all of which are common codons, and wherein by a common codon is meant the most common codon encoding each particular amino acid residue in highly expressed human genes as shown in FIGS. 14A and 14B.

2. The synthetic nucleic acid sequence of claim 1 where the factor VIII protein has one or more of the following characteristics:
   a) the B domain is deleted (beta domain deleted (BDD) factor VIII);
   b) it has a recognition site for an intracellular protease of the PACE/furin class; or
   c) it is expressed in a non-transformed cell.

3. The synthetic nucleic acid sequence of claim 1, wherein the number of non-common or less-common codons replaced or remaining is between one and 15.

4. The synthetic nucleic acid sequence of claim 1, wherein all non-common and less-common codons are replaced with common codons.

5. A synthetic nucleic acid sequence which encodes a human Factor VIII, wherein at least one non-common codon or less-common codon has been replaced by a common codon encoding the same amino acid residue as the non-common or less-common codon and wherein the synthetic nucleic acid has a continuous stretch of common codons which comprise at least 60% of the codons of the synthetic nucleic acid sequence, and wherein by a common codon is meant the most common codon encoding each particular amino acid residue in highly expressed human genes as shown in FIGS. 14A and 14B.

6. The synthetic nucleic acid sequence of claim 5 where the factor VIII protein has one or more of the following characteristics:
   a) the B domain is deleted (BDD factor VIII);
   b) it has a recognition site for an intracellular protease of the PACE/furin class; or
   c) it is expressed in a non-transformed cell.

7. The synthetic nucleic acid sequence of claim 5, wherein the number of non-common or less-common codons replaced or remaining is between one and 15.

8. The synthetic nucleic acid sequence of claim 5, wherein all non-common and less-common codons are replaced with common codons.

9. A synthetic nucleic acid sequence which encodes a human Factor VIII, wherein at least one non-common codon or less-common codon has been replaced by a common codon encoding the same amino acid residue as the non-common or less-common codon and wherein at least 98% or more of the codons in the sequence encoding the Factor VIII are common codons and the Factor VIII is at least 90 amino acid residues in length, and wherein by a common codon is meant the most common codon encoding each particular amino acid residue in highly expressed human genes as shown in FIGS. 14A and 14B.

10. The synthetic nucleic acid sequence of claim 9 where the factor VIII protein has one or more of the following characteristics:

a) the B domain is deleted (BDD factor VIII;

b) it has a recognition site for an intracellular protease of the PACE/furin class; and c) it is expressed in a non-transformed cell.

11. The synthetic nucleic acid sequence of claim 9, wherein the number of non-common or less-common codons replaced or remaining is between one and 15.

12. The synthetic nucleic acid sequence of claim 9, wherein the number of non-common or less-common codons replaced or remaining, taken together, are equal or less than 2% of the codons in the synthetic nucleic acid sequence.

13. The synthetic nucleic acid sequence of claim 9, wherein all non-common and less-common codons are replaced with common codons.

14. The synthetic nucleic acid sequence of claim 9, wherein at least 99% of the codons in the synthetic nucleic acid sequence are common codons.

15. The synthetic nucleic acid sequence of claim 9, wherein all of the codons are replaced with common codons.

16. A synthetic nucleic acid sequence which encodes human Factor IX, wherein at least one non-common codon or less-common codon has been replaced by a common codon encoding the same amino acid residue as the non-common or less-common codon and wherein the synthetic nucleic acid has a continuous stretch of at least 150 codons all of which are common codons, and wherein by a common codon is meant the most common codon encoding each particular amino acid residue in highly expressed human genes as shown in FIGS. 14A and 14B.

17. The synthetic nucleic acid sequence of claim 16, wherein the Factor IX protein has one or more of the following characteristics:

a) it has a PACE/furin site at a pro-peptide mature protein junction; and b) is expressed in a non-transformed cell.

18. The synthetic nucleic acid sequence of claim 16, wherein the number of non-common or less-common codons replaced or remaining is between one and 15.

19. A synthetic nucleic acid sequence which encodes human Factor IX, wherein at least one non-common codon or less-common codon has been replaced by a common codon encoding the same amino acid residue as the non-common or less-common codon and wherein the synthetic nucleic acid has a continuous stretch of common codons which comprise at least 60% of the codons of the synthetic nucleic acid sequence, and wherein by a common codon is meant the most common codon encoding each particular amino acid residue in highly expressed human genes as shown in FIGS. 14A and 14B.

20. The synthetic nucleic acid sequence of claim 19, wherein the number of non-common or less-common codons replaced or remaining is between one and 15.

21. The synthetic nucleic acid sequence of claim 19, wherein the factor IX protein has one or more of the following characteristics:

a) it has a PACE/furin site at a pro-peptide mature protein junction; and b) is expressed in a non-transformed cell.

22. A synthetic nucleic acid sequence which encodes human Factor IX, wherein at least one non-common codon or less-common codon has been replaced by a common codon encoding the same amino acid residue as the non-common or less-common codon and wherein at least 98% or more of the codons in the sequence encoding the Factor IX are common codons and the Factor IX is at least 90 amino acid residues in length, and wherein by a common codon is meant the most common codon encoding each particular amino acid residue in highly expressed human genes as shown in FIGS. 14A and 14B.

23. The synthetic nucleic acid sequence of claim 22, wherein the factor IX protein has one or more of the following characteristics:

a) it has a PACE/furin site at a pro-peptide mature protein junction; and b) is expressed in a non-transformed cell.

24. The synthetic nucleic acid sequence of claim 22, wherein the number of non-common or less-common codons replaced or remaining is between one and 15.

25. The synthetic nucleic acid sequence of claim 22, wherein the number of non-common or less-common codons replaced or remaining, taken together, are equal or less then 2% of the codons in the synthetic nucleic acid sequence.

26. The synthetic nucleic acid sequence of claim 22, wherein all non-common and less-common codons are replaced with common codons.

27. The synthetic nucleic acid sequence of claim 22, wherein at least 99% of the codons in the synthetic nucleic acid sequence are common codons.

28. The synthetic nucleic acid sequence of claim 22, wherein all of the codons are replaced with common codons.

29. A vector comprising the synthetic nucleic acid sequence of claim 1, 5, 9, 16, 19 or 22.

30. A cell comprising the nucleic acid sequence of claim 1, 5, 9, 16, 19 or 22.

* * * * *

```
                              SEQUENCE LISTING

<160> NUMBER OF SEQ ID NOS: 136

<210> SEQ ID NO 1
<211> LENGTH: 4376
<212> TYPE: DNA
<213> ORGANISM: Artificial Sequence
<220> FEATURE:
<221> NAME/KEY: CDS
<222> LOCATION: (19)...(4353)
<223> OTHER INFORMATION: synthetically generated insert

<400> SEQUENCE: 1
tagaattcgt aggctagc atg cag atc gag ctg agc acc tgc ttc ttc ctg         51
                    Met Gln Ile Glu Leu Ser Thr Cys Phe Phe Leu
                     1               5                      10
tgc ctg ctg cgc ttc tgc ttc agc gcc acc cgc tac tac ctg ggc             99
Cys Leu Leu Arg Phe Cys Phe Ser Ala Thr Arg Arg Tyr Tyr Leu Gly
             15                  20                  25
gcc gtg gag ctg agc tgg gac tac atg cag agc gac ctg ggc gag ctg        147
Ala Val Glu Leu Ser Trp Asp Tyr Met Gln Ser Asp Leu Gly Glu Leu
         30                  35                  40
ccc gtg gac gcc cgc ttc ccc ccc cgc gtg ccc aag agc ttc ccc ttc        195
Pro Val Asp Ala Arg Phe Pro Pro Arg Val Pro Lys Ser Phe Pro Phe
     45                  50                  55
aac acc agc gtg gtg tac aag aag acc ctg ttc gtg gag ttc acc gac        243
Asn Thr Ser Val Val Tyr Lys Lys Thr Leu Phe Val Glu Phe Thr Asp
 60                  65                  70                  75
cac ctg ttc aac atc gcc aag ccc cgc ccc ccc tgg atg ggc ctg ctg        291
His Leu Phe Asn Ile Ala Lys Pro Arg Pro Pro Trp Met Gly Leu Leu
                 80                  85                  90
ggc ccc acc atc cag gcc gag gtg tac gac acc gtg gtg atc acc ctg        339
Gly Pro Thr Ile Gln Ala Glu Val Tyr Asp Thr Val Val Ile Thr Leu
             95                 100                 105
aag aac atg gcc agc cac ccc gtg agc ctg cac gcc gtg ggc gtg agc        387
Lys Asn Met Ala Ser His Pro Val Ser Leu His Ala Val Gly Val Ser
        110                 115                 120
tac tgg aag gcc agc gag ggc gcc gag tac gac gac cag acc agc cag        435
Tyr Trp Lys Ala Ser Glu Gly Ala Glu Tyr Asp Asp Gln Thr Ser Gln
    125                 130                 135
cgc gag aag gag gac gac aag gtg ttc ccc ggc ggc agc cac acc tac        483
Arg Glu Lys Glu Asp Asp Lys Val Phe Pro Gly Gly Ser His Thr Tyr
140                 145                 150                 155
gtg tgg cag gtg ctg aag gag aac ggc ccc atg gcc agc gac ccc ctg        531
Val Trp Gln Val Leu Lys Glu Asn Gly Pro Met Ala Ser Asp Pro Leu
                160                 165                 170
tgc ctg acc tac agc tac ctg agc cac gtg gac ctg gtg aag gac ctg        579
Cys Leu Thr Tyr Ser Tyr Leu Ser His Val Asp Leu Val Lys Asp Leu
            175                 180                 185
aac agc ggc ctg atc ggc gcc ctg ctg gtg tgc cgc gag ggc agc ctg        627
Asn Ser Gly Leu Ile Gly Ala Leu Leu Val Cys Arg Glu Gly Ser Leu
        190                 195                 200
gcc aag gag aag acc cag acc ctg cac aag ttc atc ctg ctg ttc gcc        675
Ala Lys Glu Lys Thr Gln Thr Leu His Lys Phe Ile Leu Leu Phe Ala
    205                 210                 215
gtg ttc gac gag ggc aag agc tgg cac agc gag acc aag aac agc ctg        723
Val Phe Asp Glu Gly Lys Ser Trp His Ser Glu Thr Lys Asn Ser Leu
220                 225                 230                 235
atg cag gac cgc gac gcc gcc agc gcc cgc gcc tgg ccc aag atg cac        771
Met Gln Asp Arg Asp Ala Ala Ser Ala Arg Ala Trp Pro Lys Met His
                240                 245                 250
acc gtg aac ggc tac gtg aac cgc agc ctg ccc ggc ctg atc ggc tgc        819
Thr Val Asn Gly Tyr Val Asn Arg Ser Leu Pro Gly Leu Ile Gly Cys
            255                 260                 265
cac cgc aag agc gtg tac tgg cac gtg atc ggc atg ggc acc acc ccc        867
His Arg Lys Ser Val Tyr Trp His Val Ile Gly Met Gly Thr Thr Pro
        270                 275                 280
gag gtg cac agc atc ttc ctg gag ggc cac acc ttc ctg gtg cgc aac        915
```

-continued

```
              Glu Val His Ser Ile Phe Leu Glu Gly His Thr Phe Leu Val Arg Asn
                  285                 290                 295
cac cgc cag gcc agc ctg gag atc agc ccc atc acc ttc ctg acc gcc            963
His Arg Gln Ala Ser Leu Glu Ile Ser Pro Ile Thr Phe Leu Thr Ala
300                 305                 310                 315
cag acc ctg ctg atg gac ctg ggc cag ttc ctg ctg ttc tgc cac atc           1011
Gln Thr Leu Leu Met Asp Leu Gly Gln Phe Leu Leu Phe Cys His Ile
                    320                 325                 330
agc agc cac cag cac gac ggc atg gag gcc tac gtg aag gtg gac agc           1059
Ser Ser His Gln His Asp Gly Met Glu Ala Tyr Val Lys Val Asp Ser
                335                 340                 345
tgc ccc gag gag ccc cag ctg cgc atg aag aac aac gag gag gcc gag           1107
Cys Pro Glu Glu Pro Gln Leu Arg Met Lys Asn Asn Glu Glu Ala Glu
            350                 355                 360
gac tac gac gac gac ctg acc gac agc gag atg gac gtg gtg cgc ttc           1155
Asp Tyr Asp Asp Asp Leu Thr Asp Ser Glu Met Asp Val Val Arg Phe
365                 370                 375
gac gac gac aac agc ccc agc ttc atc cag atc cgc agc gtg gcc aag           1203
Asp Asp Asp Asn Ser Pro Ser Phe Ile Gln Ile Arg Ser Val Ala Lys
380                 385                 390                 395
aag cac ccc aag acc tgg gtg cac tac atc gcc gcc gag gag gag gac           1251
Lys His Pro Lys Thr Trp Val His Tyr Ile Ala Ala Glu Glu Glu Asp
                    400                 405                 410
tgg gac tac gcc ccc ctg gtg ctg gcc ccc gac gac cgc agc tac aag           1299
Trp Asp Tyr Ala Pro Leu Val Leu Ala Pro Asp Asp Arg Ser Tyr Lys
                415                 420                 425
agc cag tac ctg aac aac ggc ccc cag cgc atc ggc cgc aag tac aag           1347
Ser Gln Tyr Leu Asn Asn Gly Pro Gln Arg Ile Gly Arg Lys Tyr Lys
            430                 435                 440
aag gtg cgc ttc atg gcc tac acc gac gag acc ttc aag acc cgc gag           1395
Lys Val Arg Phe Met Ala Tyr Thr Asp Glu Thr Phe Lys Thr Arg Glu
445                 450                 455
gcc atc cag cac gag agc ggc atc ctg ggc ccc ctg tac ggc gag               1443
Ala Ile Gln His Glu Ser Gly Ile Leu Gly Pro Leu Leu Tyr Gly Glu
460                 465                 470                 475
gtg ggc gac acc ctg ctg atc atc ttc aag aac cag gcc agc cgc ccc           1491
Val Gly Asp Thr Leu Leu Ile Ile Phe Lys Asn Gln Ala Ser Arg Pro
                    480                 485                 490
tac aac atc tac ccc cac ggc atc acc gac gtg cgc ccc ctg tac agc           1539
Tyr Asn Ile Tyr Pro His Gly Ile Thr Asp Val Arg Pro Leu Tyr Ser
                495                 500                 505
cgc cgc ctg ccc aag ggc gtg aag cac ctg aag gac ttc ccc atc ctg           1587
Arg Arg Leu Pro Lys Gly Val Lys His Leu Lys Asp Phe Pro Ile Leu
            510                 515                 520
ccc ggc gag atc ttc aag tac aag tgg acc gtg acc gtg gag gac ggc           1635
Pro Gly Glu Ile Phe Lys Tyr Lys Trp Thr Val Thr Val Glu Asp Gly
525                 530                 535
ccc acc aag agc gac ccc cgc tgc ctg acc cgc tac tac agc agc ttc           1683
Pro Thr Lys Ser Asp Pro Arg Cys Leu Thr Arg Tyr Tyr Ser Ser Phe
540                 545                 550                 555
gtg aac atg gag cgc gac ctg gcc agc ggc ctg atc ggc ccc ctg ctg           1731
Val Asn Met Glu Arg Asp Leu Ala Ser Gly Leu Ile Gly Pro Leu Leu
                    560                 565                 570
atc tgc tac aag gag agc gtg gac cag cgc ggc aac cag atc atg agc           1779
Ile Cys Tyr Lys Glu Ser Val Asp Gln Arg Gly Asn Gln Ile Met Ser
                575                 580                 585
gac aag cgc aac gtg atc ctg ttc agc gtg ttc gac gag aac cgc agc           1827
Asp Lys Arg Asn Val Ile Leu Phe Ser Val Phe Asp Glu Asn Arg Ser
            590                 595                 600
tgg tac ctg acc gag aac atc cag cgc ttc ctg ccc aac ccc gcc ggc           1875
Trp Tyr Leu Thr Glu Asn Ile Gln Arg Phe Leu Pro Asn Pro Ala Gly
605                 610                 615
gtg cag ctg gag gac ccc gag ttc cag gcc agc aac atc atg cac agc           1923
Val Gln Leu Glu Asp Pro Glu Phe Gln Ala Ser Asn Ile Met His Ser
620                 625                 630                 635
atc aac ggc tac gtg ttc gac agc ctg cag ctg agc gtg tgc ctg cac           1971
Ile Asn Gly Tyr Val Phe Asp Ser Leu Gln Leu Ser Val Cys Leu His
                    640                 645                 650
gag gtg gcc tac tgg tac atc ctg agc atc ggc gcc cag acc gac ttc           2019
Glu Val Ala Tyr Trp Tyr Ile Leu Ser Ile Gly Ala Gln Thr Asp Phe
                655                 660                 665
ctg agc gtg ttc ttc agc ggc tac acc ttc aag cac aag atg gtg tac           2067
Leu Ser Val Phe Phe Ser Gly Tyr Thr Phe Lys His Lys Met Val Tyr
            670                 675                 680
gag gac acc ctg acc ctg ttc ccc ttc agc ggc gag acc gtg ttc atg           2115
Glu Asp Thr Leu Thr Leu Phe Pro Phe Ser Gly Glu Thr Val Phe Met
685                 690                 695
agc atg gag aac ccc ggc ctg tgg atc ctg ggc tgc cac aac agc gac           2163
Ser Met Glu Asn Pro Gly Leu Trp Ile Leu Gly Cys His Asn Ser Asp
```

-continued

```
                700                 705                 710                 715
ttc cgc aac cgc ggc atg acc gcc ctg ctg aag gtg agc agc tgc gac       2211
Phe Arg Asn Arg Gly Met Thr Ala Leu Leu Lys Val Ser Ser Cys Asp
                    720                 725                 730
aag aac acc ggc gac tac tac gag gac agc tac gag gac atc agc gcc       2259
Lys Asn Thr Gly Asp Tyr Tyr Glu Asp Ser Tyr Glu Asp Ile Ser Ala
            735                 740                 745
tac ctg ctg agc aag aac aac gcc atc gag ccc cgc ctg gag gag atc       2307
Tyr Leu Leu Ser Lys Asn Asn Ala Ile Glu Pro Arg Leu Glu Glu Ile
                750                 755                 760
acc cgc acc acc ctg cag agc gac cag gag gag atc gac tac gac gac       2355
Thr Arg Thr Thr Leu Gln Ser Asp Gln Glu Glu Ile Asp Tyr Asp Asp
            765                 770                 775
acc atc agc gtg gag atg aag aag gag gac ttc gac atc tac gac gag       2403
Thr Ile Ser Val Glu Met Lys Lys Glu Asp Phe Asp Ile Tyr Asp Glu
                780                 785                 790                 795
gac gag aac cag agc ccc cgc agc ttc cag aag aag acc cgc cac tac       2451
Asp Glu Asn Gln Ser Pro Arg Ser Phe Gln Lys Lys Thr Arg His Tyr
                    800                 805                 810
ttc atc gcc gcc gtg gag cgc ctg tgg gac tac ggc atg agc agc agc       2499
Phe Ile Ala Ala Val Glu Arg Leu Trp Asp Tyr Gly Met Ser Ser Ser
            815                 820                 825
ccc cac gtg ctg cgc aac cgc gcc cag agc ggc agc gtg ccc cag ttc       2547
Pro His Val Leu Arg Asn Arg Ala Gln Ser Gly Ser Val Pro Gln Phe
                830                 835                 840
aag aag gtg gtg ttc cag gag ttc acc gac ggc agc ttc acc cag ccc       2595
Lys Lys Val Val Phe Gln Glu Phe Thr Asp Gly Ser Phe Thr Gln Pro
            845                 850                 855
ctg tac cgc ggc gag ctg aac gag cac ctg ggc ctg ctg ggc ccc tac       2643
Leu Tyr Arg Gly Glu Leu Asn Glu His Leu Gly Leu Leu Gly Pro Tyr
860                 865                 870                 875
atc cgc gcc gag gtg gag gac aac atc atg gtg acc ttc cgc aac cag       2691
Ile Arg Ala Glu Val Glu Asp Asn Ile Met Val Thr Phe Arg Asn Gln
                    880                 885                 890
gcc agc cgc ccc tac agc ttc tac agc agc ctg atc agc tac gag gag       2739
Ala Ser Arg Pro Tyr Ser Phe Tyr Ser Ser Leu Ile Ser Tyr Glu Glu
            895                 900                 905
gac cag cgc cag ggc gcc gag ccc cgc aag aac ttc gtg aag ccc aac       2787
Asp Gln Arg Gln Gly Ala Glu Pro Arg Lys Asn Phe Val Lys Pro Asn
                910                 915                 920
gag acc aag acc tac ttc tgg aag gtg cag cac cac atg gcc ccc acc       2835
Glu Thr Lys Thr Tyr Phe Trp Lys Val Gln His His Met Ala Pro Thr
            925                 930                 935
aag gac gag ttc gac tgc aag gcc tgg gcc tac ttc agc gac gtg gac       2883
Lys Asp Glu Phe Asp Cys Lys Ala Trp Ala Tyr Phe Ser Asp Val Asp
940                 945                 950                 955
ctg gag aag gac gtg cac agc ggc ctg atc ggg ccc ctg ctg gtg tgc       2931
Leu Glu Lys Asp Val His Ser Gly Leu Ile Gly Pro Leu Leu Val Cys
                    960                 965                 970
cac acc aac acc ctg aac ccc gcc cac ggc cgc cag gtg acc gtg cag       2979
His Thr Asn Thr Leu Asn Pro Ala His Gly Arg Gln Val Thr Val Gln
            975                 980                 985
gag ttc gcc ctg ttc ttc acc atc ttc gac gag acc aag agc tgg tac       3027
Glu Phe Ala Leu Phe Phe Thr Ile Phe Asp Glu Thr Lys Ser Trp Tyr
                990                 995                 1000
ttc acc gag aac atg gag cgc aac tgc cgc gcc ccc tgc aac atc cag       3075
Phe Thr Glu Asn Met Glu Arg Asn Cys Arg Ala Pro Cys Asn Ile Gln
            1005                1010                1015
atg gag gac ccc acc ttc aag gag aac tac cgc ttc cac gcc atc aac       3123
Met Glu Asp Pro Thr Phe Lys Glu Asn Tyr Arg Phe His Ala Ile Asn
1020                1025                1030                1035
ggc tac atc atg gac acc ctg aaa ggc ctg gtg atg gcc cag gac cag       3171
Gly Tyr Ile Met Asp Thr Leu Lys Gly Leu Val Met Ala Gln Asp Gln
                    1040                1045                1050
cgc atc cgc tgg tac ctg ctg agc atg ggc agc aac gag aac atc cac       3219
Arg Ile Arg Trp Tyr Leu Leu Ser Met Gly Ser Asn Glu Asn Ile His
            1055                1060                1065
agc atc cac ttc agc ggc cac gtg ttc acc gtg cgc aag aag gag gag       3267
Ser Ile His Phe Ser Gly His Val Phe Thr Val Arg Lys Lys Glu Glu
            1070                1075                1080
tac aag atg gcc ctg tac aac ctg tac ccc ggc gtg ttc gag acc gtg       3315
Tyr Lys Met Ala Leu Tyr Asn Leu Tyr Pro Gly Val Phe Glu Thr Val
            1085                1090                1095
gag atg ctg ccc agc aag gcc ggc atc tgg cgc gtg gag tgc ctg atc       3363
Glu Met Leu Pro Ser Lys Ala Gly Ile Trp Arg Val Glu Cys Leu Ile
1100                1105                1110                1115
ggc gag cac ctg cac gcc ggc atg agc acc ctg ttc ctg gtg tac agc       3411
Gly Glu His Leu His Ala Gly Met Ser Thr Leu Phe Leu Val Tyr Ser
                    1120                1125                1130
```

-continued

```
aac aag tgc cag acc ccc ctg ggc atg gcc agc ggc cac atc cgc gac     3459
Asn Lys Cys Gln Thr Pro Leu Gly Met Ala Ser Gly His Ile Arg Asp
            1135                1140                1145
ttc cag atc acc gcc agc ggc cag tac ggc cag tgg gcc ccc aag ctg     3507
Phe Gln Ile Thr Ala Ser Gly Gln Tyr Gly Gln Trp Ala Pro Lys Leu
        1150                1155                1160
gcc cgc ctg cac tac agc ggc agc atc aac gcc tgg agc acc aag gag     3555
Ala Arg Leu His Tyr Ser Gly Ser Ile Asn Ala Trp Ser Thr Lys Glu
    1165                1170                1175
ccc ttc agc tgg atc aag gtg gac ctg ctg gcc ccc atg atc atc cac     3603
Pro Phe Ser Trp Ile Lys Val Asp Leu Leu Ala Pro Met Ile Ile His
1180                1185                1190                1195
ggc atc aag acc cag ggc gcc cgc cag aac ttc agc agc ctg tac atc     3651
Gly Ile Lys Thr Gln Gly Ala Arg Gln Asn Phe Ser Ser Leu Tyr Ile
            1200                1205                1210
agc cag ttc atc atc atg tac agc ctg gac ggc aag aag tgg cag acc     3699
Ser Gln Phe Ile Ile Met Tyr Ser Leu Asp Gly Lys Lys Trp Gln Thr
        1215                1220                1225
tac cgc ggc aac agc acc ggc acc ctg atg gtg ttc ttc ggc aac gtg     3747
Tyr Arg Gly Asn Ser Thr Gly Thr Leu Met Val Phe Phe Gly Asn Val
    1230                1235                1240
gac agc agc ggc atc aag cac aac atc ttc aac ccc ccc atc atc gcc     3795
Asp Ser Ser Gly Ile Lys His Asn Ile Phe Asn Pro Pro Ile Ile Ala
1245                1250                1255
cgc tac atc cgc ctg cac ccc acc cac tac agc atc cgc agc acc ctg     3843
Arg Tyr Ile Arg Leu His Pro Thr His Tyr Ser Ile Arg Ser Thr Leu
1260                1265                1270                1275
cgc atg gag ctg atg ggc tgc gac ctg aac agc tgc agc atg ccc ctg     3891
Arg Met Glu Leu Met Gly Cys Asp Leu Asn Ser Cys Ser Met Pro Leu
            1280                1285                1290
ggc atg gag agc aag gcc atc agc gac gcc cag atc acc gcc agc agc     3939
Gly Met Glu Ser Lys Ala Ile Ser Asp Ala Gln Ile Thr Ala Ser Ser
        1295                1300                1305
tac ttc acc aac atg ttc gcc acc tgg agc ccc agc aag gcc cgc ctg     3987
Tyr Phe Thr Asn Met Phe Ala Thr Trp Ser Pro Ser Lys Ala Arg Leu
    1310                1315                1320
cac ctg cag ggc cgc agc aac gcc tgg cgc ccc cag gtg aac aac ccc     4035
His Leu Gln Gly Arg Ser Asn Ala Trp Arg Pro Gln Val Asn Asn Pro
1325                1330                1335
aag gag tgg ctg cag gtg gac ttc cag aag acc atg aag gtg acc ggc     4083
Lys Glu Trp Leu Gln Val Asp Phe Gln Lys Thr Met Lys Val Thr Gly
1340                1345                1350                1355
gtg acc acc cag ggc gtg aag agc ctg ctg acc agc atg tac gtg aag     4131
Val Thr Thr Gln Gly Val Lys Ser Leu Leu Thr Ser Met Tyr Val Lys
            1360                1365                1370
gag ttc ctg atc agc agc agc cag gac ggc cac cag tgg acc ctg ttc     4179
Glu Phe Leu Ile Ser Ser Ser Gln Asp Gly His Gln Trp Thr Leu Phe
        1375                1380                1385
ttc cag aac ggc aag gtg aag gtg ttc cag ggc aac cag gac agc ttc     4227
Phe Gln Asn Gly Lys Val Lys Val Phe Gln Gly Asn Gln Asp Ser Phe
    1390                1395                1400
acc ccc gtg gtg aac agc ctg gac ccc ccc ctg ctg acc cgc tac ctg     4275
Thr Pro Val Val Asn Ser Leu Asp Pro Pro Leu Leu Thr Arg Tyr Leu
1405                1410                1415
cgc atc cac ccc cag agc tgg gtg cac cag atc gcc ctg cgc atg gag     4323
Arg Ile His Pro Gln Ser Trp Val His Gln Ile Ala Leu Arg Met Glu
1420                1425                1430                1435
gtg ctg ggc tgc gag gcc cag gac ctg tac tagctgcccg ggctacaagc      4373
Val Leu Gly Cys Glu Ala Gln Asp Leu Tyr
            1440                1445
ttt                                                                 4376

<210> SEQ ID NO 2
<211> LENGTH: 4384
<212> TYPE: DNA
<213> ORGANISM: Artificial Sequence
<220> FEATURE:
<223> OTHER INFORMATION: synthetically generated insert
<220> FEATURE:
<221> NAME/KEY: CDS
<222> LOCATION: (19)...(4359)

<400> SEQUENCE: 2
tagaattcgt aggctagc atg cag atc gag ctg agc acc tgc ttc ttc ctg     51
                    Met Gln Ile Glu Leu Ser Thr Cys Phe Phe Leu
                     1               5                  10
tgc ctg ctg cgc ttc tgc ttc agc gcc acc cgc cgc tac tac ctg ggc     99
```

```
                Cys Leu Leu Arg Phe Cys Phe Ser Ala Thr Arg Arg Tyr Tyr Leu Gly
                                 15                  20                  25 gcc gtg gag ctg agc tgg gac tac atg cag agc gac ctg ggc gag ctg          147
Ala Val Glu Leu Ser Trp Asp Tyr Met Gln Ser Asp Leu Gly Glu Leu
             30                  35                  40 ccc gtg gac gcc cgc ttc ccc ccc cgc gtg ccc aag agc ttc ccc ttc          195
Pro Val Asp Ala Arg Phe Pro Pro Arg Val Pro Lys Ser Phe Pro Phe
     45                  50                  55 aac acc agc gtg gtg tac aag aag acc ctg ttc gtg gag ttc acc gac          243
Asn Thr Ser Val Val Tyr Lys Lys Thr Leu Phe Val Glu Phe Thr Asp
 60                  65                  70                  75 cac ctg ttc aac atc gcc aag ccc cgc ccc tgg atg ggc ctg ctg              291
His Leu Phe Asn Ile Ala Lys Pro Arg Pro Pro Trp Met Gly Leu Leu
                 80                  85                  90 ggc ccc acc atc cag gcc gag gtg tac gac acc gtg gtg atc acc ctg          339
Gly Pro Thr Ile Gln Ala Glu Val Tyr Asp Thr Val Val Ile Thr Leu
             95                 100                 105 aag aac atg gcc agc cac ccc gtg agc ctg cac gcc gtg ggc gtg agc          387
Lys Asn Met Ala Ser His Pro Val Ser Leu His Ala Val Gly Val Ser
    110                 115                 120 tac tgg aag gcc agc gag ggc gcc gag tac gac gac cag acc agc cag          435
Tyr Trp Lys Ala Ser Glu Gly Ala Glu Tyr Asp Asp Gln Thr Ser Gln
125                 130                 135 cgc gag aag gag gac gac aag gtg ttc ccc ggc ggc agc cac acc tac          483
Arg Glu Lys Glu Asp Asp Lys Val Phe Pro Gly Gly Ser His Thr Tyr
140                 145                 150                 155 gtg tgg cag gtg ctg aag gag aac ggc ccc atg gcc agc gac ccc ctg          531
Val Trp Gln Val Leu Lys Glu Asn Gly Pro Met Ala Ser Asp Pro Leu
                160                 165                 170 tgc ctg acc tac agc tac ctg agc cac gtg gac ctg gtg aag gac ctg          579
Cys Leu Thr Tyr Ser Tyr Leu Ser His Val Asp Leu Val Lys Asp Leu
            175                 180                 185 aac agc ggc ctg atc ggc gcc ctg ctg gtg tgc cgc gag ggc agc ctg          627
Asn Ser Gly Leu Ile Gly Ala Leu Leu Val Cys Arg Glu Gly Ser Leu
        190                 195                 200 gcc aag gag aag acc cag acc ctg cac aag ttc atc ctg ctg ttc gcc          675
Ala Lys Glu Lys Thr Gln Thr Leu His Lys Phe Ile Leu Leu Phe Ala
205                 210                 215 gtg ttc gac gag ggc aag agc tgg cac agc gag acc aag aac agc ctg          723
Val Phe Asp Glu Gly Lys Ser Trp His Ser Glu Thr Lys Asn Ser Leu
220                 225                 230                 235 atg cag gac cgc gac gcc gcc agc gcc cgc gcc tgg ccc aag atg cac          771
Met Gln Asp Arg Asp Ala Ala Ser Ala Arg Ala Trp Pro Lys Met His
                240                 245                 250 acc gtg aac ggc tac gtg aac cgc agc ctg ccc ggc ctg atc ggc tgc          819
Thr Val Asn Gly Tyr Val Asn Arg Ser Leu Pro Gly Leu Ile Gly Cys
            255                 260                 265 cac cgc aag agc gtg tac tgg cac gtg atc ggc atg ggc acc acc ccc          867
His Arg Lys Ser Val Tyr Trp His Val Ile Gly Met Gly Thr Thr Pro
        270                 275                 280 gag gtg cac agc atc ttc ctg gag ggc cac acc ttc ctg gtg cgc aac          915
Glu Val His Ser Ile Phe Leu Glu Gly His Thr Phe Leu Val Arg Asn
285                 290                 295 cac cgc cag gcc agc ctg gag atc agc ccc atc acc ttc ctg acc gcc          963
His Arg Gln Ala Ser Leu Glu Ile Ser Pro Ile Thr Phe Leu Thr Ala
300                 305                 310                 315 cag acc ctg ctg atg gac ctg ggc cag ttc ctg ctg ttc tgc cac atc         1011
Gln Thr Leu Leu Met Asp Leu Gly Gln Phe Leu Leu Phe Cys His Ile
                320                 325                 330 agc agc cac cag cac gac ggc atg gag gcc tac gtg aag gtg gac agc         1059
Ser Ser His Gln His Asp Gly Met Glu Ala Tyr Val Lys Val Asp Ser
            335                 340                 345 tgc ccc gag gag ccc cag ctg cgc atg aag aac aac gag gag gcc gag         1107
Cys Pro Glu Glu Pro Gln Leu Arg Met Lys Asn Asn Glu Glu Ala Glu
        350                 355                 360 gac tac gac gac gac ctg acc gac agc gag atg gac gtg gtg cgc ttc         1155
Asp Tyr Asp Asp Asp Leu Thr Asp Ser Glu Met Asp Val Val Arg Phe
365                 370                 375 gac gac gac aac agc ccc agc ttc atc cag atc cgc agc gtg gcc aag         1203
Asp Asp Asp Asn Ser Pro Ser Phe Ile Gln Ile Arg Ser Val Ala Lys
380                 385                 390                 395 aag cag ggg aag acc tgg gtg cac tac atc gcc gcc gag gag gag gac         1251
Lys Gln Gly Lys Thr Trp Val His Tyr Ile Ala Ala Glu Glu Glu Asp
                400                 405                 410 tgg gac tac gcc ccc ctg gtg ctg gcc ccc gac gac cgc agc tac aag         1299
Trp Asp Tyr Ala Pro Leu Val Leu Ala Pro Asp Asp Arg Ser Tyr Lys
            415                 420                 425 agc cag tac ctg aac aac ggc ccc cag cgc atc ggc cgc aag tac aag         1347
Ser Gln Tyr Leu Asn Asn Gly Pro Gln Arg Ile Gly Arg Lys Tyr Lys
```

-continued

```
          430                     435                     440
aag gtg cgc ttc atg gcc tac acc gac gag acc ttc aag acc cgc gag    1395
Lys Val Arg Phe Met Ala Tyr Thr Asp Glu Thr Phe Lys Thr Arg Glu
            445                     450                     455
gcc atc cag cac gag agc ggc atc ctg ggc ccc ctg ctg tac ggc gag    1443
Ala Ile Gln His Glu Ser Gly Ile Leu Gly Pro Leu Leu Tyr Gly Glu
460                     465                     470                     475
gtg ggc gac acc ctg ctc atc atc ttc aag aac cag gcc agc cgc ccc    1491
Val Gly Asp Thr Leu Leu Ile Ile Phe Lys Asn Gln Ala Ser Arg Pro
                480                     485                     490
tac aac atc tac ccc cac ggc atc acc gac gtg cgc ccc ctg tac agc    1539
Tyr Asn Ile Tyr Pro His Gly Ile Thr Asp Val Arg Pro Leu Tyr Ser
                    495                     500                     505
cgc cgc ctg ccc aag ggc gtg aag cac ctg aag gac ttc ccc atc ctg    1587
Arg Arg Leu Pro Lys Gly Val Lys His Leu Lys Asp Phe Pro Ile Leu
                        510                     515                     520
ccc ggc gag atc ttc aag tac aag tgg acc gtg acc gtg gag gac ggc    1635
Pro Gly Glu Ile Phe Lys Tyr Lys Trp Thr Val Thr Val Glu Asp Gly
525                     530                     535
ccc acc aag agc gac ccc cgc tgc ctg acc cgc tac tac agc agc ttc    1683
Pro Thr Lys Ser Asp Pro Arg Cys Leu Thr Arg Tyr Tyr Ser Ser Phe
540                     545                     550                     555
gtg aac atg gag cgc gac ctg gcc agc ggc ctg atc ggc ccc ctg ctg    1731
Val Asn Met Glu Arg Asp Leu Ala Ser Gly Leu Ile Gly Pro Leu Leu
                560                     565                     570
atc tgc tac aag gag agc gtg gac cag cgc ggc aac cag atc atg agc    1779
Ile Cys Tyr Lys Glu Ser Val Asp Gln Arg Gly Asn Gln Ile Met Ser
                    575                     580                     585
gac aag cgc aac gtg atc ctg ttc agc gtg ttc gac gag aac cgc agc    1827
Asp Lys Arg Asn Val Ile Leu Phe Ser Val Phe Asp Glu Asn Arg Ser
                        590                     595                     600
tgg tac ctg acc gag aac atc cag cgc ttc ctg ccc aac ccc gcc ggc    1875
Trp Tyr Leu Thr Glu Asn Ile Gln Arg Phe Leu Pro Asn Pro Ala Gly
605                     610                     615
gtg cag ctg gag gac ccc gag ttc cag gcc agc aac atc atg cac agc    1923
Val Gln Leu Glu Asp Pro Glu Phe Gln Ala Ser Asn Ile Met His Ser
620                     625                     630                     635
atc aac ggc tac gtg ttc gac agc ctg cag ctg agc gtg tgc ctg cac    1971
Ile Asn Gly Tyr Val Phe Asp Ser Leu Gln Leu Ser Val Cys Leu His
                640                     645                     650
gag gtg gcc tac tgg tac atc ctg agc atc ggc gcc cag acc gac ttc    2019
Glu Val Ala Tyr Trp Tyr Ile Leu Ser Ile Gly Ala Gln Thr Asp Phe
                    655                     660                     665
ctg agc gtg ttc ttc agc ggc tac acc ttc aag cac aag atg gtg tac    2067
Leu Ser Val Phe Phe Ser Gly Tyr Thr Phe Lys His Lys Met Val Tyr
                        670                     675                     680
gag gac acc ctg acc ctg ttc ccc ttc agc ggc gag acc gtg ttc atg    2115
Glu Asp Thr Leu Thr Leu Phe Pro Phe Ser Gly Glu Thr Val Phe Met
685                     690                     695
agc atg gag aac ccc ggc ctg tgg atc ctg ggc tgc cac aac agc gac    2163
Ser Met Glu Asn Pro Gly Leu Trp Ile Leu Gly Cys His Asn Ser Asp
700                     705                     710                     715
ttc cgc aac cgc ggc atg acc gcc ctg ctg aag gtg agc agc tgc gac    2211
Phe Arg Asn Arg Gly Met Thr Ala Leu Leu Lys Val Ser Ser Cys Asp
                720                     725                     730
aag aac acc ggc gac tac tac gag gac agc tac gag gac atc agc gcc    2259
Lys Asn Thr Gly Asp Tyr Tyr Glu Asp Ser Tyr Glu Asp Ile Ser Ala
                    735                     740                     745
tac ctg ctg agc aag aac aac gcc atc gag ccc cgc agg cgc agg cgc    2307
Tyr Leu Leu Ser Lys Asn Asn Ala Ile Glu Pro Arg Arg Arg Arg
                        750                     755                     760
gag atc acc cgc acc acc ctg cag agc gac cag gag gag atc gac tac    2355
Glu Ile Thr Arg Thr Thr Leu Gln Ser Asp Gln Glu Glu Ile Asp Tyr
765                     770                     775
gac gac acc atc agc gtg gag atg aag aag gag gac ttc gac atc tac    2403
Asp Asp Thr Ile Ser Val Glu Met Lys Lys Glu Asp Phe Asp Ile Tyr
780                     785                     790                     795
gac gag gac gag aac cag agc ccc cgc agc ttc cag aag aag acc cgc    2451
Asp Glu Asp Glu Asn Gln Ser Pro Arg Ser Phe Gln Lys Lys Thr Arg
                800                     805                     810
cac tac ttc atc gcc gcc gtg gag cgc ctg tgg gac tac ggc atg agc    2499
His Tyr Phe Ile Ala Ala Val Glu Arg Leu Trp Asp Tyr Gly Met Ser
                    815                     820                     825
agc agc ccc cac gtg ctg cgc aac cgc gcc cag agc ggc agc gtg ccc    2547
Ser Ser Pro His Val Leu Arg Asn Arg Ala Gln Ser Gly Ser Val Pro
                        830                     835                     840
cag ttc aag aag gtg gtg ttc cag gag ttc acc gac ggc agc ttc acc    2595
Gln Phe Lys Lys Val Val Phe Gln Glu Phe Thr Asp Gly Ser Phe Thr
845                     850                     855
```

-continued

| | |
|---|---|
| cag ccc ctg tac cgc ggc gag ctg aac gag cac ctg ggc ctg ctg ggc<br>Gln Pro Leu Tyr Arg Gly Glu Leu Asn Glu His Leu Gly Leu Leu Gly<br>860                 865               870               875 | 2643 |
| ccc tac atc cgc gcc gag gtg gag gac aac atc atg gtg acc ttc cgc<br>Pro Tyr Ile Arg Ala Glu Val Glu Asp Asn Ile Met Val Thr Phe Arg<br>               880                         885               890 | 2691 |
| aac cag gcc agc cgc ccc tac agc ttc tac agc agc ctg atc agc tac<br>Asn Gln Ala Ser Arg Pro Tyr Ser Phe Tyr Ser Ser Leu Ile Ser Tyr<br>                 895                   900               905 | 2739 |
| gag gag gac cag cgc cag ggc gcc gag ccc cgc aag aac ttc gtg aag<br>Glu Glu Asp Gln Arg Gln Gly Ala Glu Pro Arg Lys Asn Phe Val Lys<br>910                 915               920 | 2787 |
| ccc aac gag acc aag acc tac ttc tgg aag gtg cag cac cac atg gcc<br>Pro Asn Glu Thr Lys Thr Tyr Phe Trp Lys Val Gln His His Met Ala<br>925                 930               935 | 2835 |
| ccc acc aag gac gag ttc gac tgc aag gcc tgg gcc tac ttc agc gac<br>Pro Thr Lys Asp Glu Phe Asp Cys Lys Ala Trp Ala Tyr Phe Ser Asp<br>940                 945               950               955 | 2883 |
| gtg gac ctg gag aag gac gtg cac agc ggc ctg atc ggc ccc ctg ctg<br>Val Asp Leu Glu Lys Asp Val His Ser Gly Leu Ile Gly Pro Leu Leu<br>               960                         965 | 2931 |
| gtg tgc cac acc aac acc ctg aac ccc gcc cac ggc cgc cag gtg acc<br>Val Cys His Thr Asn Thr Leu Asn Pro Ala His Gly Arg Gln Val Thr<br>                 975                   980               985 | 2979 |
| gtg cag gag ttc gcc ctg ttc ttc acc atc ttc gac gag acc aag agc<br>Val Gln Glu Phe Ala Leu Phe Phe Thr Ile Phe Asp Glu Thr Lys Ser<br>         990                        995               1000 | 3027 |
| tgg tac ttc acc gag aac atg gag cgc aac tgc cgc gcc ccc tgc aac<br>Trp Tyr Phe Thr Glu Asn Met Glu Arg Asn Cys Arg Ala Pro Cys Asn<br>1005               1010               1015 | 3075 |
| atc cag atg gag gac ccc acc ttc aag gag aac tac cgc ttc cac gcc<br>Ile Gln Met Glu Asp Pro Thr Phe Lys Glu Asn Tyr Arg Phe His Ala<br>1020               1025               1030               1035 | 3123 |
| atc aac ggc tac atc atg gac acc ctg ccc ggc ctg gtg atg gcc cag<br>Ile Asn Gly Tyr Ile Met Asp Thr Leu Pro Gly Leu Val Met Ala Gln<br>                1040               1045               1050 | 3171 |
| gac cag cgc atc cgc tgg tac ctg ctg agc atg ggc agc aac gag aac<br>Asp Gln Arg Ile Arg Trp Tyr Leu Leu Ser Met Gly Ser Asn Glu Asn<br>                1055               1060               1065 | 3219 |
| atc cac agc atc cac ttc agc ggc cac gtg ttc acc gtg cgc aag aag<br>Ile His Ser Ile His Phe Ser Gly His Val Phe Thr Val Arg Lys Lys<br>         1070                       1075               1080 | 3267 |
| gag gag tac aag atg gcc ctg tac aac ctg tac ccc ggc gtg ttc gag<br>Glu Glu Tyr Lys Met Ala Leu Tyr Asn Leu Tyr Pro Gly Val Phe Glu<br>1085               1090               1095 | 3315 |
| acc gtg gag atg ctg ccc agc aag gcc ggc atc tgg cgc gtg gag tgc<br>Thr Val Glu Met Leu Pro Ser Lys Ala Gly Ile Trp Arg Val Glu Cys<br>1100               1105               1110               1115 | 3363 |
| ctg atc ggc gag cac ctg cac gcc ggc atg agc acc ctg ttc ctg gtg<br>Leu Ile Gly Glu His Leu His Ala Gly Met Ser Thr Leu Phe Leu Val<br>                1120               1125               1130 | 3411 |
| tac agc aac aag tgc cag acc ccc ctg ggc atg gcc agc ggc cac atc<br>Tyr Ser Asn Lys Cys Gln Thr Pro Leu Gly Met Ala Ser Gly His Ile<br>                   1135               1140               1145 | 3459 |
| cgc gac ttc cag atc acc gcc agc ggc cag tac ggc cag tgg gcc ccc<br>Arg Asp Phe Gln Ile Thr Ala Ser Gly Gln Tyr Gly Gln Trp Ala Pro<br>             1150               1155               1160 | 3507 |
| aag ctg gcc cgc ctg cac tac agc ggc agc atc aac gcc tgg agc acc<br>Lys Leu Ala Arg Leu His Tyr Ser Gly Ser Ile Asn Ala Trp Ser Thr<br>1165               1170               1175 | 3555 |
| aag gag ccc ttc agc tgg atc aag gtg gac ctg ctg gcc ccc atg atc<br>Lys Glu Pro Phe Ser Trp Ile Lys Val Asp Leu Leu Ala Pro Met Ile<br>1180               1185               1190               1195 | 3603 |
| atc cac ggc atc aag acc cag ggc gcc cgc cag aag ttc agc agc ctg<br>Ile His Gly Ile Lys Thr Gln Gly Ala Arg Gln Lys Phe Ser Ser Leu<br>1200               1205               1210 | 3651 |
| tac atc agc cag ttc atc atc atg tac agc ctg gac ggc aag aag tgg<br>Tyr Ile Ser Gln Phe Ile Ile Met Tyr Ser Leu Asp Gly Lys Lys Trp<br>                1215               1220               1225 | 3699 |
| cag acc tac cgc ggc aac agc acc ggc acc ctg atg gtg ttc ttc ggc<br>Gln Thr Tyr Arg Gly Asn Ser Thr Gly Thr Leu Met Val Phe Phe Gly<br>             1230               1235               1240 | 3747 |
| aac gtg gac agc agc ggc atc aag cac aac atc ttc aac ccc ccc atc<br>Asn Val Asp Ser Ser Gly Ile Lys His Asn Ile Phe Asn Pro Pro Ile<br>         1245                       1250               1255 | 3795 |
| atc gcc cgc tac atc cgc ctg cac ccc acc cac tac agc atc cgc agc<br>Ile Ala Arg Tyr Ile Arg Leu His Pro Thr His Tyr Ser Ile Arg Ser<br>1260               1265               1270               1275 | 3843 |
| acc ctg cgc atg gag ctg atg ggc tgc gac ctg aac agc tgc agc atg | 3891 |

-continued

```
Thr Leu Arg Met Glu Leu Met Gly Cys Asp Leu Asn Ser Cys Ser Met
                1280                1285                1290
ccc ctg ggc atg gag agc aag gcc atc agc gac gcc cag atc acc gcc    3939
Pro Leu Gly Met Glu Ser Lys Ala Ile Ser Asp Ala Gln Ile Thr Ala
                1295                1300                1305
agc agc tac ttc acc aac atg ttc gcc acc tgg agc ccc agc aag gcc    3987
Ser Ser Tyr Phe Thr Asn Met Phe Ala Thr Trp Ser Pro Ser Lys Ala
            1310                1315                1320
cgc ctg cac ctg cag ggc cgc agc aac gcc tgg cgc ccc cag gtg aac    4035
Arg Leu His Leu Gln Gly Arg Ser Asn Ala Trp Arg Pro Gln Val Asn
            1325                1330                1335
aac ccc aag gag tgg ctg cag gtg gac ttc cag aag acc atg aag gtg    4083
Asn Pro Lys Glu Trp Leu Gln Val Asp Phe Gln Lys Thr Met Lys Val
1340                1345                1350                1355
acc ggc gtg acc acc cag ggc gtg aag agc ctg ctg acc agc atg tac    4131
Thr Gly Val Thr Thr Gln Gly Val Lys Ser Leu Leu Thr Ser Met Tyr
                1360                1365                1370
gtg aag gag ttc ctg atc agc agc agc cag gac ggc cac cag tgg acc    4179
Val Lys Glu Phe Leu Ile Ser Ser Ser Gln Asp Gly His Gln Trp Thr
                1375                1380                1385
ctg ttc ttc cag aac ggc aag gtg aag gtg ttc cag ggc aac cag gac    4227
Leu Phe Phe Gln Asn Gly Lys Val Lys Val Phe Gln Gly Asn Gln Asp
            1390                1395                1400
agc ttc acc ccc gtg gtg aac agc ctg gac ccc ccc ctg ctg acc cgc    4275
Ser Phe Thr Pro Val Val Asn Ser Leu Asp Pro Pro Leu Leu Thr Arg
        1405                1410                1415
tac ctg cgc atc cac ccc cag agc tgg gtg cac cag atc gcc ctg cgc    4323
Tyr Leu Arg Ile His Pro Gln Ser Trp Val His Gln Ile Ala Leu Arg
1420                1425                1430                1435
atg gag gtg ctg ggc tgc gag gcc cag gac ctg tac tagctgccccg        4369
Met Glu Val Leu Gly Cys Glu Ala Gln Asp Leu Tyr
                1440                1445
ggctacaagc tttac                                                   4384

<210> SEQ ID NO 3
<211> LENGTH: 1445
<212> TYPE: PRT
<213> ORGANISM: Artificial Sequence
<220> FEATURE:
<223> OTHER INFORMATION: synthetically generated peptide

<400> SEQUENCE: 3

Met Gln Ile Glu Leu Ser Thr Cys Phe Phe Leu Cys Leu Leu Arg Phe
1               5                   10                  15
Cys Phe Ser Ala Thr Arg Arg Tyr Tyr Leu Gly Ala Val Glu Leu Ser
            20                  25                  30
Trp Asp Tyr Met Gln Ser Asp Leu Gly Glu Leu Pro Val Asp Ala Arg
        35                  40                  45
Phe Pro Pro Arg Val Pro Lys Ser Phe Pro Phe Asn Thr Ser Val Val
    50                  55                  60
Tyr Lys Lys Thr Leu Phe Val Glu Phe Thr Asp His Leu Phe Asn Ile
65                  70                  75                  80
Ala Lys Pro Arg Pro Pro Trp Met Gly Leu Leu Gly Pro Thr Ile Gln
                85                  90                  95
Ala Glu Val Tyr Asp Thr Val Val Ile Thr Leu Lys Asn Met Ala Ser
            100                 105                 110
His Pro Val Ser Leu His Ala Val Gly Val Ser Tyr Trp Lys Ala Ser
        115                 120                 125
Glu Gly Ala Glu Tyr Asp Asp Gln Thr Ser Gln Arg Glu Lys Glu Asp
    130                 135                 140
Asp Lys Val Phe Pro Gly Gly Ser His Thr Tyr Val Trp Gln Val Leu
145                 150                 155                 160
Lys Glu Asn Gly Pro Met Ala Ser Asp Pro Leu Cys Leu Thr Tyr Ser
                165                 170                 175
Tyr Leu Ser His Val Asp Leu Val Lys Asp Leu Asn Ser Gly Leu Ile
            180                 185                 190
Gly Ala Leu Leu Val Cys Arg Glu Gly Ser Leu Ala Lys Glu Lys Thr
        195                 200                 205
Gln Thr Leu His Lys Phe Ile Leu Leu Phe Ala Val Phe Asp Glu Gly
    210                 215                 220
Lys Ser Trp His Ser Glu Thr Lys Asn Ser Leu Met Gln Asp Arg Asp
225                 230                 235                 240
Ala Ala Ser Ala Arg Ala Trp Pro Lys Met His Thr Val Asn Gly Tyr
                245                 250                 255
Val Asn Arg Ser Leu Pro Gly Leu Ile Gly Cys His Arg Lys Ser Val
            260                 265                 270
Tyr Trp His Val Ile Gly Met Gly Thr Thr Pro Glu Val His Ser Ile
```

```
              275                 280                 285
    Phe Leu Glu Gly His Thr Phe Leu Val Arg Asn His Arg Gln Ala Ser
    290                 295                 300
    Leu Glu Ile Ser Pro Ile Thr Phe Leu Thr Ala Gln Thr Leu Leu Met
305                 310                 315                 320
    Asp Leu Gly Gln Phe Leu Leu Phe Cys His Ile Ser Ser His Gln His
                    325                 330                 335
    Asp Gly Met Glu Ala Tyr Val Lys Val Asp Ser Cys Pro Glu Glu Pro
                340                 345                 350
    Gln Leu Arg Met Lys Asn Asn Glu Glu Ala Glu Asp Tyr Asp Asp Asp
                355                 360                 365
    Leu Thr Asp Ser Glu Met Asp Val Val Arg Phe Asp Asp Asn Ser
        370                 375                 380
    Pro Ser Phe Ile Gln Ile Arg Ser Val Ala Lys Lys His Pro Lys Thr
    385                 390                 395                 400
    Trp Val His Tyr Ile Ala Ala Glu Glu Glu Asp Trp Asp Tyr Ala Pro
                    405                 410                 415
    Leu Val Leu Ala Pro Asp Asp Arg Ser Tyr Lys Ser Gln Tyr Leu Asn
                420                 425                 430
    Asn Gly Pro Gln Arg Ile Gly Arg Lys Tyr Lys Lys Val Arg Phe Met
                435                 440                 445
    Ala Tyr Thr Asp Glu Thr Phe Lys Thr Arg Glu Ala Ile Gln His Glu
        450                 455                 460
    Ser Gly Ile Leu Gly Pro Leu Leu Tyr Gly Glu Val Gly Asp Thr Leu
    465                 470                 475                 480
    Leu Ile Ile Phe Lys Asn Gln Ala Ser Arg Pro Tyr Asn Ile Tyr Pro
                    485                 490                 495
    His Gly Ile Thr Asp Val Arg Pro Leu Tyr Ser Arg Arg Leu Pro Lys
                500                 505                 510
    Gly Val Lys His Leu Lys Asp Phe Pro Ile Leu Pro Gly Glu Ile Phe
                515                 520                 525
    Lys Tyr Lys Trp Thr Val Thr Val Glu Asp Gly Pro Thr Lys Ser Asp
        530                 535                 540
    Pro Arg Cys Leu Thr Arg Tyr Tyr Ser Ser Phe Val Asn Met Glu Arg
    545                 550                 555                 560
    Asp Leu Ala Ser Gly Leu Ile Gly Pro Leu Leu Ile Cys Tyr Lys Glu
                    565                 570                 575
    Ser Val Asp Gln Arg Gly Asn Gln Ile Met Ser Asp Lys Arg Asn Val
                580                 585                 590
    Ile Leu Phe Ser Val Phe Asp Glu Asn Arg Ser Trp Tyr Leu Thr Glu
                595                 600                 605
    Asn Ile Gln Arg Phe Leu Pro Asn Pro Ala Gly Val Gln Leu Glu Asp
        610                 615                 620
    Pro Glu Phe Gln Ala Ser Asn Ile Met His Ser Ile Asn Gly Tyr Val
    625                 630                 635                 640
    Phe Asp Ser Leu Gln Leu Ser Val Cys Leu His Glu Val Ala Tyr Trp
                    645                 650                 655
    Tyr Ile Leu Ser Ile Gly Ala Gln Thr Asp Phe Leu Ser Val Phe Phe
                660                 665                 670
    Ser Gly Tyr Thr Phe Lys His Lys Met Val Tyr Glu Asp Thr Leu Thr
                675                 680                 685
    Leu Phe Pro Phe Ser Gly Glu Thr Val Phe Met Ser Met Glu Asn Pro
        690                 695                 700
    Gly Leu Trp Ile Leu Gly Cys His Asn Ser Asp Phe Arg Asn Arg Gly
    705                 710                 715                 720
    Met Thr Ala Leu Leu Lys Val Ser Ser Cys Asp Lys Asn Thr Gly Asp
                    725                 730                 735
    Tyr Tyr Glu Asp Ser Tyr Glu Asp Ile Ser Ala Tyr Leu Leu Ser Lys
                740                 745                 750
    Asn Asn Ala Ile Glu Pro Arg Leu Glu Glu Ile Thr Arg Thr Thr Leu
                755                 760                 765
    Gln Ser Asp Gln Glu Glu Ile Asp Tyr Asp Asp Thr Ile Ser Val Glu
        770                 775                 780
    Met Lys Lys Glu Asp Phe Asp Ile Tyr Asp Glu Asp Glu Asn Gln Ser
    785                 790                 795                 800
    Pro Arg Ser Phe Gln Lys Lys Thr Arg His Tyr Phe Ile Ala Ala Val
                    805                 810                 815
    Glu Arg Leu Trp Asp Tyr Gly Met Ser Ser Ser Pro His Val Leu Arg
                820                 825                 830
    Asn Arg Ala Gln Ser Gly Ser Val Pro Gln Phe Lys Lys Val Val Phe
                835                 840                 845
    Gln Glu Phe Thr Asp Gly Ser Phe Thr Gln Pro Leu Tyr Arg Gly Glu
        850                 855                 860
    Leu Asn Glu His Leu Gly Leu Leu Gly Pro Tyr Ile Arg Ala Glu Val
    865                 870                 875                 880
    Glu Asp Asn Ile Met Val Thr Phe Arg Asn Gln Ala Ser Arg Pro Tyr
                    885                 890                 895
    Ser Phe Tyr Ser Ser Leu Ile Ser Tyr Glu Glu Asp Gln Arg Gln Gly
                900                 905                 910
```

```
Ala Glu Pro Arg Lys Asn Phe Val Lys Pro Asn Glu Thr Lys Thr Tyr
        915                 920                 925
Phe Trp Lys Val Gln His His Met Ala Pro Thr Lys Asp Glu Phe Asp
        930                 935                 940
Cys Lys Ala Trp Ala Tyr Phe Ser Asp Val Asp Leu Glu Lys Asp Val
945                 950                 955                 960
His Ser Gly Leu Ile Gly Pro Leu Leu Val Cys His Thr Asn Thr Leu
            965                 970                 975
Asn Pro Ala His Gly Arg Gln Val Thr Val Gln Glu Phe Ala Leu Phe
        980                 985                 990
Phe Thr Ile Phe Asp Glu Thr Lys Ser Trp Tyr Phe Thr Glu Asn Met
    995                1000                1005
Glu Arg Asn Cys Arg Ala Pro Cys Asn Ile Gln Met Glu Asp Pro Thr
       1010                1015                1020
Phe Lys Glu Asn Tyr Arg Phe His Ala Ile Asn Gly Tyr Ile Met Asp
1025                1030                1035                1040
Thr Leu Lys Gly Leu Val Met Ala Gln Asp Gln Arg Ile Arg Trp Tyr
               1045                1050                1055
Leu Leu Ser Met Gly Ser Asn Glu Asn Ile His Ser Ile His Phe Ser
               1060                1065                1070
Gly His Val Phe Thr Val Arg Lys Lys Glu Glu Tyr Lys Met Ala Leu
       1075                1080                1085
Tyr Asn Leu Tyr Pro Gly Val Phe Glu Thr Val Glu Met Leu Pro Ser
       1090                1095                1100
Lys Ala Gly Ile Trp Arg Val Glu Cys Leu Ile Gly Glu His Leu His
1105                1110                1115                1120
Ala Gly Met Ser Thr Leu Phe Leu Val Tyr Ser Asn Lys Cys Gln Thr
                1125                1130                1135
Pro Leu Gly Met Ala Ser Gly His Ile Arg Asp Phe Gln Ile Thr Ala
                1140                1145                1150
Ser Gly Gln Tyr Gly Gln Trp Ala Pro Lys Leu Ala Arg Leu His Tyr
       1155                1160                1165
Ser Gly Ser Ile Asn Ala Trp Ser Thr Lys Glu Pro Phe Ser Trp Ile
1170                1175                1180
Lys Val Asp Leu Leu Ala Pro Met Ile Ile His Gly Ile Lys Thr Gln
1185                1190                1195                1200
Gly Ala Arg Gln Asn Phe Ser Ser Leu Tyr Ile Ser Gln Phe Ile Ile
                1205                1210                1215
Met Tyr Ser Leu Asp Gly Lys Lys Trp Gln Thr Tyr Arg Gly Asn Ser
       1220                1225                1230
Thr Gly Thr Leu Met Val Phe Phe Gly Asn Val Asp Ser Ser Gly Ile
       1235                1240                1245
Lys His Asn Ile Phe Asn Pro Pro Ile Ile Ala Arg Tyr Ile Arg Leu
       1250                1255                1260
His Pro Thr His Tyr Ser Ile Arg Ser Thr Leu Arg Met Glu Leu Met
1265                1270                1275                1280
Gly Cys Asp Leu Asn Ser Cys Ser Met Pro Leu Gly Met Glu Ser Lys
                1285                1290                1295
Ala Ile Ser Asp Ala Gln Ile Thr Ala Ser Ser Tyr Phe Thr Asn Met
                1300                1305                1310
Phe Ala Thr Trp Ser Pro Ser Lys Ala Arg Leu His Leu Gln Gly Arg
       1315                1320                1325
Ser Asn Ala Trp Arg Pro Gln Val Asn Pro Lys Glu Trp Leu Gln
       1330                1335                1340
Val Asp Phe Gln Lys Thr Met Lys Val Thr Gly Val Thr Thr Gln Gly
1345                1350                1355                1360
Val Lys Ser Leu Leu Thr Ser Met Tyr Val Lys Glu Phe Leu Ile Ser
               1365                1370                1375
Ser Ser Gln Asp Gly His Gln Trp Thr Leu Phe Phe Gln Asn Gly Lys
       1380                1385                1390
Val Lys Val Phe Gln Gly Asn Gln Asp Ser Phe Thr Pro Val Val Asn
       1395                1400                1405
Ser Leu Asp Pro Pro Leu Leu Thr Arg Tyr Leu Arg Ile His Pro Gln
       1410                1415                1420
Ser Trp Val His Gln Ile Ala Leu Arg Met Glu Val Leu Gly Cys Glu
1425                1430                1435                1440
Ala Gln Asp Leu Tyr
               1445
```

<210> SEQ ID NO 4
<211> LENGTH: 1447
<212> TYPE: PRT
<213> ORGANISM: Artificial Sequence
<220> FEATURE:
<223> OTHER INFORMATION: synthetically generated peptide

<400> SEQUENCE: 4

```
Met Gln Ile Glu Leu Ser Thr Cys Phe Phe Leu Cys Leu Leu Arg Phe
  1               5                  10                  15
Cys Phe Ser Ala Thr Arg Arg Tyr Tyr Leu Gly Ala Val Glu Leu Ser
             20                  25                  30
Trp Asp Tyr Met Gln Ser Asp Leu Gly Glu Leu Pro Val Asp Ala Arg
             35                  40                  45
Phe Pro Pro Arg Val Pro Lys Ser Phe Pro Phe Asn Thr Ser Val Val
         50                  55                  60
Tyr Lys Lys Thr Leu Phe Val Glu Phe Thr Asp His Leu Phe Asn Ile
 65              70                  75                  80
Ala Lys Pro Arg Pro Pro Trp Met Gly Leu Leu Gly Pro Thr Ile Gln
                 85                  90                  95
Ala Glu Val Tyr Asp Thr Val Ile Thr Leu Lys Asn Met Ala Ser
            100                 105                 110
His Pro Val Ser Leu His Ala Val Gly Val Ser Tyr Trp Lys Ala Ser
            115                 120                 125
Glu Gly Ala Glu Tyr Asp Asp Gln Thr Ser Gln Arg Glu Lys Glu Asp
            130                 135                 140
Asp Lys Val Phe Pro Gly Gly Ser His Thr Tyr Val Trp Gln Val Leu
        145                 150                 155                 160
Lys Glu Asn Gly Pro Met Ala Ser Asp Pro Leu Cys Leu Thr Tyr Ser
                165                 170                 175
Tyr Leu Ser His Val Asp Leu Val Lys Asp Leu Asn Ser Gly Leu Ile
            180                 185                 190
Gly Ala Leu Leu Val Cys Arg Glu Gly Ser Leu Ala Lys Glu Lys Thr
            195                 200                 205
Gln Thr Leu His Lys Phe Ile Leu Leu Phe Ala Val Phe Asp Glu Gly
            210                 215                 220
Lys Ser Trp His Ser Glu Thr Lys Asn Ser Leu Met Gln Asp Arg Asp
225                 230                 235                 240
Ala Ala Ser Ala Arg Ala Trp Pro Lys Met His Thr Val Asn Gly Tyr
            245                 250                 255
Val Asn Arg Ser Leu Pro Gly Leu Ile Gly Cys His Arg Lys Ser Val
            260                 265                 270
Tyr Trp His Val Ile Gly Met Gly Thr Thr Pro Glu Val His Ser Ile
            275                 280                 285
Phe Leu Glu Gly His Thr Phe Leu Val Arg Asn His Arg Gln Ala Ser
        290                 295                 300
Leu Glu Ile Ser Pro Ile Thr Phe Leu Thr Ala Gln Thr Leu Leu Met
305                 310                 315                 320
Asp Leu Gly Gln Phe Leu Leu Phe Cys His Ile Ser Ser His Gln His
                325                 330                 335
Asp Gly Met Glu Ala Tyr Val Lys Val Asp Ser Cys Pro Glu Glu Pro
            340                 345                 350
Gln Leu Arg Met Lys Asn Asn Glu Glu Ala Glu Asp Tyr Asp Asp Asp
            355                 360                 365
Leu Thr Asp Ser Glu Met Asp Val Val Arg Phe Asp Asp Asp Asn Ser
        370                 375                 380
Pro Ser Phe Ile Gln Ile Arg Ser Val Ala Lys Lys Gln Gly Lys Thr
385                 390                 395                 400
Trp Val His Tyr Ile Ala Ala Glu Glu Glu Asp Trp Asp Tyr Ala Pro
            405                 410                 415
Leu Val Leu Ala Pro Asp Asp Arg Ser Tyr Lys Ser Gln Tyr Leu Asn
            420                 425                 430
Asn Gly Pro Gln Arg Ile Gly Arg Lys Tyr Lys Lys Val Arg Phe Met
            435                 440                 445
Ala Tyr Thr Asp Glu Thr Phe Lys Thr Arg Glu Ala Ile Gln His Glu
            450                 455                 460
Ser Gly Ile Leu Gly Pro Leu Leu Tyr Gly Glu Val Gly Asp Thr Leu
465                 470                 475                 480
Leu Ile Ile Phe Lys Asn Gln Ala Ser Arg Pro Tyr Asn Ile Tyr Pro
                485                 490                 495
His Gly Ile Thr Asp Val Arg Pro Leu Tyr Ser Arg Arg Leu Pro Lys
            500                 505                 510
Gly Val Lys His Leu Lys Asp Phe Pro Ile Leu Pro Gly Glu Ile Phe
        515                 520                 525
Lys Tyr Lys Trp Thr Val Thr Val Glu Asp Gly Pro Thr Lys Ser Asp
        530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
            565                 570                 575
Ser Val Asp Gln Arg Gly Asn Gln Ile Met Ser Asp Lys Arg Asn Val
            580                 585                 590
Ile Leu Phe Ser Val Phe Asp Glu Asn Arg Ser Trp Tyr Leu Thr Glu
        595                 600                 605
Asn Ile Gln Arg Phe Leu Pro Asn Pro Ala Gly Val Gln Leu Glu Asp
        610                 615                 620
Pro Glu Phe Gln Ala Ser Asn Ile Met His Ser Ile Asn Gly Tyr Val
```

-continued

```
625                 630                 635                 640
Phe Asp Ser Leu Gln Leu Ser Val Cys Leu His Glu Val Ala Tyr Trp
                645                 650                 655
Tyr Ile Leu Ser Ile Gly Ala Gln Thr Asp Phe Leu Ser Val Phe Phe
                660                 665                 670
Ser Gly Tyr Thr Phe Lys His Lys Met Val Tyr Glu Asp Thr Leu Thr
                675                 680                 685
Leu Phe Pro Phe Ser Gly Glu Thr Val Phe Met Ser Met Glu Asn Pro
            690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                725                 730                 735
Tyr Tyr Glu Asp Ser Tyr Glu Asp Ile Ser Ala Tyr Leu Leu Ser Lys
                740                 745                 750
Asn Asn Ala Ile Glu Pro Arg Arg Arg Arg Glu Ile Thr Arg Thr
                755                 760                 765
Thr Leu Gln Ser Asp Gln Glu Glu Ile Asp Tyr Asp Asp Thr Ile Ser
            770                 775                 780
Val Glu Met Lys Lys Glu Asp Phe Asp Ile Tyr Asp Glu Asp Glu Asn
785                 790                 795                 800
Gln Ser Pro Arg Ser Phe Gln Lys Lys Thr Arg His Tyr Phe Ile Ala
                805                 810                 815
Ala Val Glu Arg Leu Trp Asp Tyr Gly Met Ser Ser Ser Pro His Val
                820                 825                 830
Leu Arg Asn Arg Ala Gln Ser Gly Ser Val Pro Gln Phe Lys Lys Val
                835                 840                 845
Val Phe Gln Glu Phe Thr Asp Gly Ser Phe Thr Gln Pro Leu Tyr Arg
            850                 855                 860
Gly Glu Leu Asn Glu His Leu Gly Leu Leu Gly Pro Tyr Ile Arg Ala
865                 870                 875                 880
Glu Val Glu Asp Asn Ile Met Val Thr Phe Arg Asn Gln Ala Ser Arg
                885                 890                 895
Pro Tyr Ser Phe Tyr Ser Ser Leu Ile Ser Tyr Glu Glu Asp Gln Arg
                900                 905                 910
Gln Gly Ala Glu Pro Arg Lys Asn Phe Val Lys Pro Asn Glu Thr Lys
            915                 920                 925
Thr Tyr Phe Trp Lys Val Gln His His Met Ala Pro Thr Lys Asp Glu
            930                 935                 940
Phe Asp Cys Lys Ala Trp Ala Tyr Phe Ser Asp Val Asp Leu Glu Lys
945                 950                 955                 960
Asp Val His Ser Gly Leu Ile Gly Pro Leu Leu Val Cys His Thr Asn
                965                 970                 975
Thr Leu Asn Pro Ala His Gly Arg Gln Val Thr Val Gln Glu Phe Ala
            980                 985                 990
Leu Phe Phe Thr Ile Phe Asp Glu Thr Lys Ser Trp Tyr Phe Thr Glu
            995                 1000                1005
Asn Met Glu Arg Asn Cys Arg Ala Pro Cys Asn Ile Gln Met Glu Asp
1010                1015                1020
Pro Thr Phe Lys Glu Asn Tyr Arg Phe His Ala Ile Asn Gly Tyr Ile
1025                1030                1035                1040
Met Asp Thr Leu Pro Gly Leu Val Met Ala Gln Asp Gln Arg Ile Arg
                1045                1050                1055
Trp Tyr Leu Leu Ser Met Gly Ser Asn Glu Asn Ile His Ser Ile His
                1060                1065                1070
Phe Ser Gly His Val Phe Thr Val Arg Lys Lys Glu Glu Tyr Lys Met
            1075                1080                1085
Ala Leu Tyr Asn Leu Tyr Pro Gly Val Phe Glu Thr Val Glu Met Leu
    1090                1095                1100
Pro Ser Lys Ala Gly Ile Trp Arg Val Glu Cys Leu Ile Gly Glu His
1105                1110                1115                1120
Leu His Ala Gly Met Ser Thr Leu Phe Leu Val Tyr Ser Asn Lys Cys
                1125                1130                1135
Gln Thr Pro Leu Gly Met Ala Ser Gly His Ile Arg Asp Phe Gln Ile
            1140                1145                1150
Thr Ala Ser Gly Gln Tyr Gly Gln Trp Ala Pro Lys Leu Ala Arg Leu
            1155                1160                1165
His Tyr Ser Gly Ser Ile Asn Ala Trp Ser Thr Lys Glu Pro Phe Ser
            1170                1175                1180
Trp Ile Lys Val Asp Leu Leu Ala Pro Met Ile Ile His Gly Ile Lys
1185                1190                1195                1200
Thr Gln Gly Ala Arg Gln Lys Phe Ser Ser Leu Tyr Ile Ser Gln Phe
                1205                1210                1215
Ile Ile Met Tyr Ser Leu Asp Gly Lys Lys Trp Gln Thr Tyr Arg Gly
                1220                1225                1230
Asn Ser Thr Gly Thr Leu Met Val Phe Phe Gly Asn Val Asp Ser Ser
                1235                1240                1245
Gly Ile Lys His Asn Ile Phe Asn Pro Pro Ile Ile Ala Arg Tyr Ile
            1250                1255                1260
```

-continued

```
Arg Leu His Pro Thr His Tyr Ser Ile Arg Ser Thr Leu Arg Met Glu
1265                1270                1275                1280
Leu Met Gly Cys Asp Leu Asn Ser Cys Ser Met Pro Leu Gly Met Glu
            1285                1290                1295
Ser Lys Ala Ile Ser Asp Ala Gln Ile Thr Ala Ser Ser Tyr Phe Thr
        1300                1305                1310
Asn Met Phe Ala Thr Trp Ser Pro Ser Lys Ala Arg Leu His Leu Gln
    1315                1320                1325
Gly Arg Ser Asn Ala Trp Arg Pro Gln Val Asn Asn Pro Lys Glu Trp
  1330                1335                1340
Leu Gln Val Asp Phe Gln Lys Thr Met Lys Val Thr Gly Val Thr Thr
1345                1350                1355                1360
Gln Gly Val Lys Ser Leu Leu Thr Ser Met Tyr Val Lys Glu Phe Leu
            1365                1370                1375
Ile Ser Ser Ser Gln Asp Gly His Gln Trp Thr Leu Phe Phe Gln Asn
        1380                1385                1390
Gly Lys Val Lys Val Phe Gln Gly Asn Gln Asp Ser Phe Thr Pro Val
    1395                1400                1405
Val Asn Ser Leu Asp Pro Pro Leu Leu Thr Arg Tyr Leu Arg Ile His
    1410                1415                1420
Pro Gln Ser Trp Val His Gln Ile Ala Leu Arg Met Glu Val Leu Gly
1425                1430                1435                1440
Cys Glu Ala Gln Asp Leu Tyr
            1445

<210> SEQ ID NO 5
<211> LENGTH: 16
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (7)...(16)
<223> OTHER INFORMATION: n = a, g, c, or t

<400> SEQUENCE: 5
gaggagnnnn nnnnnn                                                    16

<210> SEQ ID NO 6
<211> LENGTH: 16
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (7)...(16)
<223> OTHER INFORMATION: n = a, g, c, or t

<400> SEQUENCE: 6
ctcctcnnnn nnnnnn                                                    16

<210> SEQ ID NO 7
<211> LENGTH: 118
<212> TYPE: DNA
<213> ORGANISM: Homo sapiens

<400> SEQUENCE: 7
gtagaattcg taggctagca tgcagatcga gctgagcacc tgcttcttcc tgtgcctgct    60
gcgcttctgc ttcagcgcca cccgccgcta ctacctgggc gccgtggagc tgagctgg     18

<210> SEQ ID NO 8
<211> LENGTH: 104
<212> TYPE: DNA
<213> ORGANISM: Homo sapiens

<400> SEQUENCE: 8
gactacatgc agagcgacct gggcgagctg cccgtggacg cccgcttccc ccccgcgtg    60
```

-continued

```
cccaagagct tccccttcaa caccagcgtg gtgtacaaga agac            04
```

<210> SEQ ID NO 9
<211> LENGTH: 88
<212> TYPE: DNA
<213> ORGANISM: Homo sapiens

<400> SEQUENCE: 9

```
cctgttcgtg gagttcaccg accacctgtt caacatcgcc aagccccgcc ccccctggat    60
gggcctgctg ggcccctaca agctttac                                       88
```

<210> SEQ ID NO 10
<211> LENGTH: 119
<212> TYPE: DNA
<213> ORGANISM: Homo sapiens

<400> SEQUENCE: 10

```
gtaaagcttg tagggcccca gcaggcccat ccaggggggg cggggcttgg cgatgttgaa    60
caggtggtcg gtgaactcca cgaacagggt cttcttgtac accacgctgg tgttgaagg    19
```

<210> SEQ ID NO 11
<211> LENGTH: 107
<212> TYPE: DNA
<213> ORGANISM: Homo sapiens

<400> SEQUENCE: 11

```
ggaagctctt gggcacgcgg ggggggaagc gggcgtccac gggcagctcg cccaggtcgc    60
tctgcatgta gtcccagctc agctccacgg cgcccaggta gtagcgg                  07
```

<210> SEQ ID NO 12
<211> LENGTH: 84
<212> TYPE: DNA
<213> ORGANISM: Homo sapiens

<400> SEQUENCE: 12

```
cgggtggcgc tgaagcagaa gcgcagcagg cacaggaaga agcaggtgct cagctcgatc    60
tgcatgctag cctacgaatt ctac                                           84
```

<210> SEQ ID NO 13
<211> LENGTH: 115
<212> TYPE: DNA
<213> ORGANISM: Homo sapiens

<400> SEQUENCE: 13

```
gtagaattcg tagggcccc accatccagg ccgaggtgta cgacaccgtg gtgatcaccc     60
tgaagaacat ggccagccac cccgtgagcc tgcacgccgt gggcgtgagc tactg         15
```

<210> SEQ ID NO 14
<211> LENGTH: 103
<212> TYPE: DNA
<213> ORGANISM: Homo sapiens

<400> SEQUENCE: 14

```
gaaggccagc gagggcgccg agtacgacga ccagaccagc cagcgcgaga aggaggacga    60
caaggtgttc cccggcggca gccacaccta cgtgtggcag gtg                      103
```

<210> SEQ ID NO 15
<211> LENGTH: 79
<212> TYPE: DNA
<213> ORGANISM: Homo sapiens

<400> SEQUENCE: 15
ctgaaggaga acggccccat ggccagcgac cccctgtgcc tgacctacag ctacctgagc    60
cacgtgctac aagctttac                                                 79

<210> SEQ ID NO 16
<211> LENGTH: 107
<212> TYPE: DNA
<213> ORGANISM: Homo sapiens

<400> SEQUENCE: 16
gtaaagcttg tagcacgtgg ctcaggtagc tgtaggtcag gcacaggggg tcgctggcca    60
tggggccgtt ctccttcagc acctgccaca cgtaggtgtg gctgccg                 107

<210> SEQ ID NO 17
<211> LENGTH: 101
<212> TYPE: DNA
<213> ORGANISM: Homo sapiens

<400> SEQUENCE: 17
ccggggaaca ccttgtcgtc ctccttctcg cgctggctgg tctggtcgtc gtactcggcg    60
ccctcgctgg ccttccagta gctcacgccc acggcgtgca g                       101

<210> SEQ ID NO 18
<211> LENGTH: 89
<212> TYPE: DNA
<213> ORGANISM: Homo sapiens

<400> SEQUENCE: 18
gctcacgggg tggctggcca tgttcttcag ggtgatcacc acggtgtcgt acacctcggc    60
ctggatggtg gggcccctac gaattctac                                      89

<210> SEQ ID NO 19
<211> LENGTH: 122
<212> TYPE: DNA
<213> ORGANISM: Homo sapiens

<400> SEQUENCE: 19
gtagaattcg tagccacgtg gacctggtga aggacctgaa cagcggcctg atcggcgccc    60
tgctggtgtg ccgcgagggc agcctggcca aggagaagac ccagaccctg cacaagttca   120
tc                                                                  122

<210> SEQ ID NO 20
<211> LENGTH: 110
<212> TYPE: DNA
<213> ORGANISM: Homo sapiens

<400> SEQUENCE: 20
ctgctgttcg ccgtgttcga cgagggcaag agctggcaca gcgagaccaa gaacagcctg    60
atgcaggacc gcgacgccgc cagcgcccgc gcctggccca agatgcacac               110

<210> SEQ ID NO 21
<211> LENGTH: 86
<212> TYPE: DNA
<213> ORGANISM: Homo sapiens

<400> SEQUENCE: 21
cgtgaacggc tacgtgaacc gcagcctgcc cggcctgatc ggctgccacc gcaagagcgt    60

-continued

```
gtactggcac gtgctacaag ctttac                                           86

<210> SEQ ID NO 22
<211> LENGTH: 108
<212> TYPE: DNA
<213> ORGANISM: Homo sapiens

<400> SEQUENCE: 22
gtaaagcttg tagcacgtgc cagtacacgc tcttgcggtg gcagccgatc aggccgggca      60
ggctgcggtt cacgtagccg ttcacggtgt gcatcttggg ccaggcgc                  108

<210> SEQ ID NO 23
<211> LENGTH: 110
<212> TYPE: DNA
<213> ORGANISM: Homo sapiens

<400> SEQUENCE: 23
gggcgctggc ggcgtcgcgg tcctgcatca ggctgttctt ggtctcgctg tgccagctct      60
tgccctcgtc gaacacggcg aacagcagga tgaacttgtg cagggtctgg                110

<210> SEQ ID NO 24
<211> LENGTH: 100
<212> TYPE: DNA
<213> ORGANISM: Homo sapiens

<400> SEQUENCE: 24
gtcttctcct tggccaggct gccctcgcgg cacaccagca gggcgccgat caggccgctg      60
ttcaggtcct tcaccaggtc cacgtggcta cgaattctac                           100

<210> SEQ ID NO 25
<211> LENGTH: 99
<212> TYPE: DNA
<213> ORGANISM: Homo sapiens

<400> SEQUENCE: 25
gtagaattcg tagcacgtga tcggcatggg caccaccccc gaggtgcaca gcatcttcct      60
ggagggccac accttcctgg tgcgcaacca ccgccaggc                             99

<210> SEQ ID NO 26
<211> LENGTH: 100
<212> TYPE: DNA
<213> ORGANISM: Homo sapiens

<400> SEQUENCE: 26
cagcctggag atcagcccca tcaccttcct gaccgcccag accctgctga tggacctggg      60
ccagttcctg ctgttctgcc acatcagcag ccaccagcac                           100

<210> SEQ ID NO 27
<211> LENGTH: 101
<212> TYPE: DNA
<213> ORGANISM: Homo sapiens

<400> SEQUENCE: 27
gacggcatgg aggcctacgt gaaggtggac agctgccccg aggagcccca gctgcgcatg      60
aagaacaacg aggaggccga ggactacgac gacgacctga c                         101

<210> SEQ ID NO 28
<211> LENGTH: 84
<212> TYPE: DNA
<213> ORGANISM: Homo sapiens
```

<400> SEQUENCE: 28
cgacagcgag atggacgtgg tgcgcttcga cgacgacaac agccccagct tcatccagat    60
ctctacggat cctacaagct ttac                                            84

<210> SEQ ID NO 29
<211> LENGTH: 109
<212> TYPE: DNA
<213> ORGANISM: Homo sapiens

<400> SEQUENCE: 29
gtaaagcttg taggatccgt agagatctgg atgaagctgg gctgttgtc gtcgtcgaag      60 cgcaccacgt ccatctcgct gtcggtcagg tcgtcgtcgt agtcctcgg               109

<210> SEQ ID NO 30
<211> LENGTH: 101
<212> TYPE: DNA
<213> ORGANISM: Homo sapiens

<400> SEQUENCE: 30
cctcctcgtt gttcttcatg cgcagctggg gctcctcggg gcagctgtcc accttcacgt    60
aggcctccat gccgtcgtgc tggtggctgc tgatgtggca g                       101

<210> SEQ ID NO 31
<211> LENGTH: 102
<212> TYPE: DNA
<213> ORGANISM: Homo sapiens

<400> SEQUENCE: 31
aacagcagga actggcccag gtccatcagc agggtctggg cggtcaggaa ggtgatgggg    60
ctgatctcca ggctggcctg gcggtggttg cgcaccagga ag                      102

<210> SEQ ID NO 32
<211> LENGTH: 72
<212> TYPE: DNA
<213> ORGANISM: Homo sapiens

<400> SEQUENCE: 32
gtgtggccct ccaggaagat gctgtgcacc tcggggtgg tgcccatgcc gatcacgtgc     60
tacgaattct ac                                                        72

<210> SEQ ID NO 33
<211> LENGTH: 122
<212> TYPE: DNA
<213> ORGANISM: Homo sapiens

<400> SEQUENCE: 33
gtagaattcg tagggatccg cagcgtggcc aagaagcacc ccaagacctg ggtgcactac    60
atcgccgccg aggaggagga ctgggactac gccccctgg tgctggcccc cgacgaccgc   120
ag                                                                  122

<210> SEQ ID NO 34
<211> LENGTH: 120
<212> TYPE: DNA
<213> ORGANISM: Homo sapiens

<400> SEQUENCE: 34
ctacaagagc cagtacctga caacggccc ccagcgcatc ggccgcaagt acaagaaggt    60

-continued

```
gcgcttcatg gcctacaccg acgagacctt caagacccgc gaggccatcc agcacgagag      120
```

<210> SEQ ID NO 35
<211> LENGTH: 115
<212> TYPE: DNA
<213> ORGANISM: Homo sapiens

<400> SEQUENCE: 35

```
cggcatcctg ggcccctgc tgtacggcga ggtgggcgac accctgctga tcatcttcaa       60
gaaccaggcc agccgcccct acaacatcta ccccacggc atcaccgacg tgcgc           115
```

<210> SEQ ID NO 36
<211> LENGTH: 86
<212> TYPE: DNA
<213> ORGANISM: Homo sapiens

<400> SEQUENCE: 36

```
cccctgtaca gccgccgcct gcccaagggc gtgaagcacc tgaaggactt ccccatcctg      60
cccggcgaga tctctacaag ctttac                                          86
```

<210> SEQ ID NO 37
<211> LENGTH: 109
<212> TYPE: DNA
<213> ORGANISM: Homo sapiens

<400> SEQUENCE: 37

```
gtaaagcttg tagagatctc gccgggcagg atggggaagt ccttcaggtg cttcacgccc      60
ttgggcaggc ggcggctgta caggggcgc acgtcggtga tgccgtggg              109
```

<210> SEQ ID NO 38
<211> LENGTH: 114
<212> TYPE: DNA
<213> ORGANISM: Homo sapiens

<400> SEQUENCE: 38

```
ggtagatgtt gtaggggcgg ctggcctggt tcttgaagat gatcagcagg gtgtcgccca      60
cctcgccgta cagcaggggg cccaggatgc cgctctcgtg ctggatggcc tcgc          114
```

<210> SEQ ID NO 39
<211> LENGTH: 121
<212> TYPE: DNA
<213> ORGANISM: Homo sapiens

<400> SEQUENCE: 39

```
gggtcttgaa ggtctcgtcg gtgtaggcca tgaagcgcac cttcttgtac ttgcggccga      60
tgcgctgggg gccgttgttc aggtactggc tcttgtagct gcggtcgtcg ggggccagca     120
c                                                                    121
```

<210> SEQ ID NO 40
<211> LENGTH: 99
<212> TYPE: DNA
<213> ORGANISM: Homo sapiens

<400> SEQUENCE: 40

```
caggggggcg tagtcccagt cctcctcctc ggcggcgatg tagtgcaccc aggtcttggg      60
gtgcttcttg gccacgctgc ggatccctac gaattctac                            99
```

<210> SEQ ID NO 41
<211> LENGTH: 102

```
<212> TYPE: DNA
<213> ORGANISM: Homo sapiens

<400> SEQUENCE: 41
gtagaattcg tagagatctt caagtacaag tggaccgtga ccgtggagga cggccccacc    60
aagagcgacc cccgctgcct gacccgctac tacagcagct tc                      102

<210> SEQ ID NO 42
<211> LENGTH: 103
<212> TYPE: DNA
<213> ORGANISM: Homo sapiens

<400> SEQUENCE: 42
gtgaacatgg agcgcgacct ggccagcggc ctgatcggcc ccctgctgat ctgctacaag    60
gagagcgtgg accagcgcgg caaccagatc atgagcgaca agc                     103

<210> SEQ ID NO 43
<211> LENGTH: 61
<212> TYPE: DNA
<213> ORGANISM: Homo sapiens

<400> SEQUENCE: 43
gcaacgtgat cctgttcagc gtgttcgacg agaaccgcag ctggtaccct acaagcttta    60
c                                                                   61

<210> SEQ ID NO 44
<211> LENGTH: 87
<212> TYPE: DNA
<213> ORGANISM: Homo sapiens

<400> SEQUENCE: 44
gtaaagcttg tagggtacca gctgcggttc tcgtcgaaca cgctgaacag gatcacgttg    60
cgcttgtcgc tcatgatctg gttgccg                                       87

<210> SEQ ID NO 45
<211> LENGTH: 101
<212> TYPE: DNA
<213> ORGANISM: Homo sapiens

<400> SEQUENCE: 45
cgctggtcca cgctctcctt gtagcagatc agcaggggc cgatcaggcc gctggccagg     60
tcgcgctcca tgttcacgaa gctgctgtag tagcgggtca g                       101

<210> SEQ ID NO 46
<211> LENGTH: 78
<212> TYPE: DNA
<213> ORGANISM: Homo sapiens

<400> SEQUENCE: 46
gcagcggggg tcgctcttgg tggggccgtc ctccacggtc acggtccact tgtacttgaa    60
gatctctacg aattctac                                                 78

<210> SEQ ID NO 47
<211> LENGTH: 120
<212> TYPE: DNA
<213> ORGANISM: Homo sapiens

<400> SEQUENCE: 47
gtagaattcg tagggtacct gaccgagaac atccagcgct tcctgcccaa ccccgccggc    60
```

```
gtgcagctgg aggaccccga gttccaggcc agcaacatca tgcacagcat caacggctac      120
```

<210> SEQ ID NO 48
<211> LENGTH: 126
<212> TYPE: DNA
<213> ORGANISM: Homo sapiens

<400> SEQUENCE: 48

```
gtgttcgaca gcctgcagct gagcgtgtgc ctgcacgagg tggcctactg gtacatcctg      60
agcatcggcg cccagaccga cttcctgagc gtgttcttca gcggctacac cttcaagcac     120
aagatg                                                                126
```

<210> SEQ ID NO 49
<211> LENGTH: 95
<212> TYPE: DNA
<213> ORGANISM: Homo sapiens

<400> SEQUENCE: 49

```
gtgtacgagg acaccctgac cctgttcccc ttcagcggcg agaccgtgtt catgagcatg      60 gagaacccccg gcctgtggat ccctacaagc tttac                                95
```

<210> SEQ ID NO 50
<211> LENGTH: 119
<212> TYPE: DNA
<213> ORGANISM: Homo sapiens

<400> SEQUENCE: 50

```
gtaaagcttg tagggatcca caggccgggg ttctccatgc tcatgaacac ggtctcgccg      60
ctgaagggga cagggtcag ggtgtcctcg tacaccatct tgtgcttgaa ggtgtagcc      119
```

<210> SEQ ID NO 51
<211> LENGTH: 124
<212> TYPE: DNA
<213> ORGANISM: Homo sapiens

<400> SEQUENCE: 51

```
gctgaagaac acgctcagga agtcggtctg ggcgccgatg ctcaggatgt accagtaggc      60
cacctcgtgc aggcacacgc tcagctgcag gctgtcgaac acgtagccgt tgatgctgtg     120
catg                                                                  124
```

<210> SEQ ID NO 52
<211> LENGTH: 98
<212> TYPE: DNA
<213> ORGANISM: Homo sapiens

<400> SEQUENCE: 52

```
atgttgctgg cctggaactc ggggtcctcc agctgcacgc cggcggggtt gggcaggaag      60
cgctggatgt tctcggtcag gtaccctacg aattctac                              98
```

<210> SEQ ID NO 53
<211> LENGTH: 111
<212> TYPE: DNA
<213> ORGANISM: Homo sapiens

<400> SEQUENCE: 53

```
gtagaattcg tagggatcct gggctgccac aacagcgact ccgcaaccg cggcatgacc      60 gccctgctga aggtgagcag ctgcgacaag aacaccggcg actactacga g              111
```

```
<210> SEQ ID NO 54
<211> LENGTH: 102
<212> TYPE: DNA
<213> ORGANISM: Homo sapiens

<400> SEQUENCE: 54
gacagctacg aggacatcag cgcctacctg ctgagcaaga acaacgccat cgagccccgc      60
ctggaggaga tcacccgcac caccctgcag agcgaccagg ag                        102

<210> SEQ ID NO 55
<211> LENGTH: 105
<212> TYPE: DNA
<213> ORGANISM: Homo sapiens

<400> SEQUENCE: 55
gagatcgact acgacgacac catcagcgtg gagatgaaga aggaggactt cgacatctac      60
gacgaggacg agaaccagag cccccgcagc ttccagaaga agacc                     105

<210> SEQ ID NO 56
<211> LENGTH: 79
<212> TYPE: DNA
<213> ORGANISM: Homo sapiens

<400> SEQUENCE: 56
cgccactact tcatcgccgc cgtggagcgc ctgtgggact acggcatgag cagcagcccc      60
cacgtgctac aagctttac                                                   79

<210> SEQ ID NO 57
<211> LENGTH: 101
<212> TYPE: DNA
<213> ORGANISM: Homo sapiens

<400> SEQUENCE: 57
gtaaagcttg tagcacgtgg gggctgctgc tcatgccgta gtcccacagg cgctccacgg      60
cggcgatgaa gtagtggcgg gtcttcttct ggaagctgcg g                         101

<210> SEQ ID NO 58
<211> LENGTH: 105
<212> TYPE: DNA
<213> ORGANISM: Homo sapiens

<400> SEQUENCE: 58
gggctctggt tctcgtcctc gtcgtagatg tcgaagtcct ccttcttcat ctccacgctg      60
atggtgtcgt cgtagtcgat ctcctcctgg tcgctctgca gggtg                     105

<210> SEQ ID NO 59
<211> LENGTH: 108
<212> TYPE: DNA
<213> ORGANISM: Homo sapiens

<400> SEQUENCE: 59
gtgcgggtga tctcctccag gcggggctcg atggcgttgt tcttgctcag caggtaggcg      60
ctgatgtcct cgtagctgtc ctcgtagtag tcgccggtgt tcttgtcg                  108

<210> SEQ ID NO 60
<211> LENGTH: 83
<212> TYPE: DNA
<213> ORGANISM: Homo sapiens

<400> SEQUENCE: 60
```

```
cagctgctca ccttcagcag ggcggtcatg ccgcggttgc ggaagtcgct gttgtggcag      60
cccaggatcc ctacgaattc tac                                             83

<210> SEQ ID NO 61
<211> LENGTH: 115
<212> TYPE: DNA
<213> ORGANISM: Homo sapiens

<400> SEQUENCE: 61
gtagaattcg tagcacgtgc tgcgcaaccg cgcccagagc ggcagcgtgc cccagttcaa     60
gaaggtggtg ttccaggagt tcaccgacgg cagcttcacc cagcccctgt accgc         115

<210> SEQ ID NO 62
<211> LENGTH: 111
<212> TYPE: DNA
<213> ORGANISM: Homo sapiens

<400> SEQUENCE: 62
ggcgagctga acgagcacct gggcctgctg gcccctaca tccgcgccga ggtggaggac     60
aacatcatgg tgaccgtgca ggagttcgcc ctgttcttca ccatcttcga c             111

<210> SEQ ID NO 63
<211> LENGTH: 106
<212> TYPE: DNA
<213> ORGANISM: Homo sapiens

<400> SEQUENCE: 63
gagaccaaga gctggtactt caccgagaac atggagcgca actgccgcgc ccctgcaac     60 atccagatgg aggaccccac cttcaaggag aactaccgct ccacg                    106

<210> SEQ ID NO 64
<211> LENGTH: 85
<212> TYPE: DNA
<213> ORGANISM: Homo sapiens

<400> SEQUENCE: 64
ccatcaacgg ctacatcatg gacaccctgc ccggcctggt gatggcccag gaccagcgca    60
tccgctggta ccctacaagc tttac                                          85

<210> SEQ ID NO 65
<211> LENGTH: 115
<212> TYPE: DNA
<213> ORGANISM: Homo sapiens

<400> SEQUENCE: 65
gtaaagcttg tagggtacca gcggatgcgc tggtcctggg ccatcaccag gccgggcagg    60
gtgtccatga tgtagccgtt gatggcgtgg aagcggtagt tctccttgaa ggtgg         115

<210> SEQ ID NO 66
<211> LENGTH: 99
<212> TYPE: DNA
<213> ORGANISM: Homo sapiens

<400> SEQUENCE: 66
ggtcctccat ctggatgttg caggggcgc ggcagttgcg ctccatgttc tcggtgaagt     60
accagctctt ggtctcgtcg aagatggtga agaacaggg                           99

<210> SEQ ID NO 67
<211> LENGTH: 110
```

```
<212> TYPE: DNA
<213> ORGANISM: Homo sapiens

<400> SEQUENCE: 67
cgaactcctg cacggtcacc atgatgttgt cctccacctc ggcgcggatg tagggccca      60 gcaggcccag gtgctcgttc agctcgccgc ggtacagggg ctgggtgaag              110

<210> SEQ ID NO 68
<211> LENGTH: 93
<212> TYPE: DNA
<213> ORGANISM: Homo sapiens

<400> SEQUENCE: 68
ctgccgtcgg tgaactcctg gaacaccacc ttcttgaact ggggcacgct gccgctctgg    60
gcgcggttgc gcagcacgtg ctacgaattc tac                                93

<210> SEQ ID NO 69
<211> LENGTH: 116
<212> TYPE: DNA
<213> ORGANISM: Homo sapiens

<400> SEQUENCE: 69
gtagaattcg tagggtgacc ttccgcaacc aggccagccg ccctacagc ttctacagca     60 gcctgatcag ctacgaggag gaccagcgcc agggcgccga gccccgcaag aacttc       116

<210> SEQ ID NO 70
<211> LENGTH: 120
<212> TYPE: DNA
<213> ORGANISM: Homo sapiens

<400> SEQUENCE: 70
gtgaagccca acgagaccaa gacctacttc tggaaggtgc agcaccacat ggcccccacc    60
aaggacgagt tcgactgcaa ggcctgggcc tacttcagcg acgtggacct ggagaaggac  120

<210> SEQ ID NO 71
<211> LENGTH: 91
<212> TYPE: DNA
<213> ORGANISM: Homo sapiens

<400> SEQUENCE: 71
gtgcacagcg gcctgatcgg cccctgctg gtgtgccaca ccaacaccct gaaccccgcc    60
cacggccgcc aggtgaccct acaagcttta c                                  91

<210> SEQ ID NO 72
<211> LENGTH: 113
<212> TYPE: DNA
<213> ORGANISM: Homo sapiens

<400> SEQUENCE: 72
gtaaagcttg tagggtcacc tggcggccgt gggcggggtt cagggtgttg gtgtggcaca   60
ccagcagggg gccgatcagg ccgctgtgca cgtccttctc caggtccacg tcg         113

<210> SEQ ID NO 73
<211> LENGTH: 121
<212> TYPE: DNA
<213> ORGANISM: Homo sapiens

<400> SEQUENCE: 73
ctgaagtagg cccaggcctt gcagtcgaac tcgtccttgg tggggccat gtggtgctgc    60
```

```
accttccaga agtaggtctt ggtctcgttg ggcttcacga agttcttgcg gggctcggcg      120
c                                                                      121

<210> SEQ ID NO 74
<211> LENGTH: 93
<212> TYPE: DNA
<213> ORGANISM: Homo sapiens

<400> SEQUENCE: 74
cctggcgctg gtcctcctcg tagctgatca ggctgctgta gaagctgtag gggcggctgg      60
cctggttgcg gaaggtcacc ctacgaattc tac                                   93

<210> SEQ ID NO 75
<211> LENGTH: 120
<212> TYPE: DNA
<213> ORGANISM: Homo sapiens

<400> SEQUENCE: 75
gtagaattcg tagggtacct gctgagcatg ggcagcaacg agaacatcca cagcatccac      60
ttcagcggcc acgtgttcac cgtgcgcaag aaggaggagt acaagatggc cctgtacaac      120

<210> SEQ ID NO 76
<211> LENGTH: 122
<212> TYPE: DNA
<213> ORGANISM: Homo sapiens

<400> SEQUENCE: 76
ctgtaccccg gcgtgttcga gaccgtggag atgctgccca gcaaggccgg catctggcgc      60
gtggagtgcc tgatcggcga gcacctgcac gccggcatga gcaccctgtt cctggtgtac      120
ag                                                                     122

<210> SEQ ID NO 77
<211> LENGTH: 102
<212> TYPE: DNA
<213> ORGANISM: Homo sapiens

<400> SEQUENCE: 77
caacaagtgc cagaccccccc tgggcatggc cagcggccac atccgcgact tccagatcac      60
cgccagcggc cagtacggcc agtgggcccc tacaagcttt ac                         102

<210> SEQ ID NO 78
<211> LENGTH: 123
<212> TYPE: DNA
<213> ORGANISM: Homo sapiens

<400> SEQUENCE: 78
gtaaagcttg taggggccca ctggccgtac tggccgctgg cggtgatctg gaagtcgcgg      60
atgtggccgc tggccatgcc caggggggtc tggcacttgt tgctgtacac caggaacagg      120
gtg                                                                    123

<210> SEQ ID NO 79
<211> LENGTH: 125
<212> TYPE: DNA
<213> ORGANISM: Homo sapiens

<400> SEQUENCE: 79
ctcatgccgg cgtgcaggtg ctcgccgatc aggcactcca cgcgccagat gccggccttg      60
ctgggcagca tctccacggt ctcgaacacg ccggggtaca ggttgtacag gccatcttg       120
```

```
                                              -continued tactc                                                                 125

<210> SEQ ID NO 80
<211> LENGTH: 96
<212> TYPE: DNA
<213> ORGANISM: Homo sapiens

<400> SEQUENCE: 80
ctccttcttg cgcacggtga acacgtggcc gctgaagtgg atgctgtgga tgttctcgtt     60
gctgcccatg ctcagcaggt accctacgaa ttctac                               96

<210> SEQ ID NO 81
<211> LENGTH: 120
<212> TYPE: DNA
<213> ORGANISM: Homo sapiens

<400> SEQUENCE: 81
gtagaattcg tagggccccc caagctggcc cgcctgcact acagcggcag catcaacgcc     60
tggagcacca aggagccctt cagctggatc aaggtggacc tgctggcccc catgatcatc    120

<210> SEQ ID NO 82
<211> LENGTH: 116
<212> TYPE: DNA
<213> ORGANISM: Homo sapiens

<400> SEQUENCE: 82
cacggcatca agacccaggg cgcccgccag aagttcagca gcctgtacat cagccagttc     60
atcatcatgt acagcctgga cggcaagaag tggcagacct accgcggcaa cagcac        116

<210> SEQ ID NO 83
<211> LENGTH: 86
<212> TYPE: DNA
<213> ORGANISM: Homo sapiens

<400> SEQUENCE: 83
cggcaccctg atggtgttct tcggcaacgt ggacagcagc ggcatcaagc acaacatctt     60 caacccccc gggctacaag ctttac                                           86

<210> SEQ ID NO 84
<211> LENGTH: 110
<212> TYPE: DNA
<213> ORGANISM: Homo sapiens

<400> SEQUENCE: 84
gtaaagcttg tagcccgggg gggttgaaga tgttgtgctt gatgccgctg ctgtccacgt     60
tgccgaagaa caccatcagg gtgccggtgc tgttgccgcg gtaggtctgc                110

<210> SEQ ID NO 85
<211> LENGTH: 113
<212> TYPE: DNA
<213> ORGANISM: Homo sapiens

<400> SEQUENCE: 85
cacttcttgc cgtccaggct gtacatgatg atgaactggc tgatgtacag gctgctgaac     60
ttctggcggg cgccctgggt cttgatgccg tggatgatca tgggggccag cag           113

<210> SEQ ID NO 86
<211> LENGTH: 99
<212> TYPE: DNA
```

<213> ORGANISM: Homo sapiens

<400> SEQUENCE: 86

```
gtccaccttg atccagctga agggctcctt ggtgctccag gcgttgatgc tgccgctgta      60
gtgcaggcgg gccagcttgg gggcccctac gaattctac                             99
```

<210> SEQ ID NO 87
<211> LENGTH: 122
<212> TYPE: DNA
<213> ORGANISM: Homo sapiens

<400> SEQUENCE: 87

```
gtagaattcg taggatatca tcgcccgcta catccgcctg caccccaccc actacagcat      60
ccgcagcacc ctgcgcatgg agctgatggg ctgcgaccta acagctgca gcatgcccct     120
gg                                                                    122
```

<210> SEQ ID NO 88
<211> LENGTH: 112
<212> TYPE: DNA
<213> ORGANISM: Homo sapiens

<400> SEQUENCE: 88

```
gcatggagag caaggccatc agcgacgccc agatcaccgc cagcagctac ttcaccaaca      60
tgttcgccac ctggagcccc agcaaggccc gcctgcacct gcagggccgc ag            112
```

<210> SEQ ID NO 89
<211> LENGTH: 89
<212> TYPE: DNA
<213> ORGANISM: Homo sapiens

<400> SEQUENCE: 89

```
caacgcctgg cgcccccagg tgaacaaccc caaggagtgg ctgcaggtgg acttccagaa      60
gaccatgaag gtgaccctac aagctttac                                       89
```

<210> SEQ ID NO 90
<211> LENGTH: 112
<212> TYPE: DNA
<213> ORGANISM: Homo sapiens

<400> SEQUENCE: 90

```
gtaaagcttg tagggtcacc ttcatggtct tctggaagtc cacctgcagc cactccttgg      60
ggttgttcac ctgggggcgc caggcgttgc tgcggccctg caggtgcagg cg            112
```

<210> SEQ ID NO 91
<211> LENGTH: 114
<212> TYPE: DNA
<213> ORGANISM: Homo sapiens

<400> SEQUENCE: 91

```
ggccttgctg gggctccagg tggcgaacat gttggtgaag tagctgctgg cggtgatctg      60
ggcgtcgctg atggccttgc tctccatgcc caggggcatg ctgcagctgt tcag          114
```

<210> SEQ ID NO 92
<211> LENGTH: 97
<212> TYPE: DNA
<213> ORGANISM: Homo sapiens

<400> SEQUENCE: 92

```
gtcgcagccc atcagctcca tgcgcagggt gctgcggatg ctgtagtggg tggggtgcag      60
```

```
gcggatgtag cgggcgatga tatcctacga attctac                              97

<210> SEQ ID NO 93
<211> LENGTH: 122
<212> TYPE: DNA
<213> ORGANISM: Homo sapiens

<400> SEQUENCE: 93
gtagaattcg tagggtgacc ggcgtgacca cccagggcgt gaagagcctg ctgaccagca    60
tgtacgtgaa ggagttcctg atcagcagca gccaggacgg ccaccagtgg accctgttct   120
tc                                                                   122

<210> SEQ ID NO 94
<211> LENGTH: 104
<212> TYPE: DNA
<213> ORGANISM: Homo sapiens

<400> SEQUENCE: 94
cagaacggca aggtgaaggt gttccagggc aaccaggaca gcttcacccc cgtggtgaac    60
agcctggacc cccccctgct gacccgctac ctgcgcatcc accc                    104

<210> SEQ ID NO 95
<211> LENGTH: 92
<212> TYPE: DNA
<213> ORGANISM: Homo sapiens

<400> SEQUENCE: 95
ccagagctgg gtgcaccaga tcgccctgcg catggaggtg ctgggctgcg aggcccagga    60
cctgtactag ctgcccgggc tacaagcttt ac                                  92

<210> SEQ ID NO 96
<211> LENGTH: 118
<212> TYPE: DNA
<213> ORGANISM: Homo sapiens

<400> SEQUENCE: 96
gtaaagcttg tagcccgggc agctagtaca ggtcctgggc ctcgcagccc agcacctcca    60
tgcgcagggc gatctggtgc acccagctct gggggtggat gcgcaggtag cgggtcag    118

<210> SEQ ID NO 97
<211> LENGTH: 100
<212> TYPE: DNA
<213> ORGANISM: Homo sapiens

<400> SEQUENCE: 97 caggggggggg tccaggctgt tcaccacggg ggtgaagctg tcctggttgc cctggaacac   60
cttcaccttg ccgttctgga agaacagggt ccactggtgg                         100

<210> SEQ ID NO 98
<211> LENGTH: 100
<212> TYPE: DNA
<213> ORGANISM: Homo sapiens

<400> SEQUENCE: 98
ccgtcctggc tgctgctgat caggaactcc ttcacgtaca tgctggtcag caggctcttc    60
acgccctggg tggtcacgcc ggtcaccta cgaattctac                          100

<210> SEQ ID NO 99
```

```
<211> LENGTH: 140
<212> TYPE: DNA
<213> ORGANISM: Homo sapiens

<400> SEQUENCE: 99
gtagaattcg gatcctgggc tgccacaaca gcgacttccg caaccgcggc atgaccgccc      60
tgctgaaggt gagcagctgc gacaagaaca ccggcgacta ctacgaggac agctacgagg     120
acatcagcgc ctacctgctg                                                 140

<210> SEQ ID NO 100
<211> LENGTH: 57
<212> TYPE: DNA
<213> ORGANISM: Homo sapiens

<400> SEQUENCE: 100 gcaagaaca acgccatcga gccccgcagg cgcaggcgcg agatcacccg caccacc          57

<210> SEQ ID NO 101
<211> LENGTH: 58
<212> TYPE: DNA
<213> ORGANISM: Homo sapiens

<400> SEQUENCE: 101
ctgcagagcg accaggagga gatcgactac gacgacacca tcagcgtgga agctttac    58

<210> SEQ ID NO 102
<211> LENGTH: 79
<212> TYPE: DNA
<213> ORGANISM: Homo sapiens

<400> SEQUENCE: 102
gtaaagcttc cacgctgatg gtgtcgtcgt agtcgatctc ctcctggtcg ctctgcaggg   60
    tggtgcgggt gatctcgcg                                                79

<210> SEQ ID NO 103
<211> LENGTH: 57
<212> TYPE: DNA
<213> ORGANISM: Homo sapiens

<400> SEQUENCE: 103
cctgcgcctg cggggctcga tggcgttgtt cttgctcagc aggtaggcgc tgatgtc      57

<210> SEQ ID NO 104
<211> LENGTH: 119
<212> TYPE: DNA
<213> ORGANISM: Homo sapiens

<400> SEQUENCE: 104
ctcgtagctg tcctcgtagt agtcgccggt gttcttgtcg cagctgctca ccttcagcag   60
    ggcggtcatg ccgcggttgc ggaagtcgct gttgtggcag cccaggatcc gaattctac   119

<210> SEQ ID NO 105
<211> LENGTH: 310
<212> TYPE: DNA
<213> ORGANISM: Artificial Sequence
<220> FEATURE:
<223> OTHER INFORMATION: synthetically generated construct

<400> SEQUENCE: 105
gtagaattcg taggctagca tgcagatcga gctgagcacc tgcttcttcc tgtgcctgct   60
    gcgcttctgc ttcagcgcca cccgccgcta ctacctgggc gccgtggagc tgagctggga  120
    ctacatgcag agcgacctgg gcgagctgcc cgtggacgcc cgcttccccc ccgcgtgcc   180
    caagagcttc cccttcaaca ccagcgtggt gtacaagaag accctgttcg tggagttcac  240
    cgaccacctg ttcaacatcg ccaagcccgg cccccctgg atgggcctgc tgggcccta    300
```

```
                                        caagctttac                                    310

<210> SEQ ID NO 106
<211> LENGTH: 297
<212> TYPE: DNA
<213> ORGANISM: Artificial Sequence
<220> FEATURE:
<223> OTHER INFORMATION: synthetically generated construct

<400> SEQUENCE: 106
gtagaattcg tagggggcccc accatccagg ccgaggtgta cgacaccgtg gtgatcaccc     60
      tgaagaacat ggccagccac cccgtgagcc tgcacgccgt gggcgtgagc tactggaagg    120
      ccagcgaggg cgccgagtac gacgaccaga ccagccagcg cgagaaggag gacgacaagg    180
      tgttccccgg cggcagccac acctacgtgt ggcaggtgct gaaggagaac ggccccatgg    240
      ccagcgaccc cctgtgcctg acctacagct acctgagcca cgtgctacaa gctttac      297

<210> SEQ ID NO 107
<211> LENGTH: 318
<212> TYPE: DNA
<213> ORGANISM: Artificial Sequence
<220> FEATURE:
<223> OTHER INFORMATION: synthetically generated construct

<400> SEQUENCE: 107
gtagaattcg tagccacgtg gacctggtga aggacctgaa cagcggcctg atcggcgccc     60
      tgctggtgtg ccgcgagggc agcctggcca aggagaagac ccagaccctg cacaagttca    120
      tcctgctgtt cgccgtgttc gacgagggca gagctggca cagcgagacc aagaacagcc    180
      tgatgcagga ccgcgacgcc gccagcgccc gcgcctggcc caagatgcac ccgtgaacg    240
      gctacgtgaa ccgcagcctg cccggcctga tcggctgcca ccgcaagagc gtgtactggc    300
      acgtgctaca agctttac                                                  318

<210> SEQ ID NO 108
<211> LENGTH: 384
<212> TYPE: DNA
<213> ORGANISM: Artificial Sequence
<220> FEATURE:
<223> OTHER INFORMATION: synthetically generated construct

<400> SEQUENCE: 108
gtagaattcg tagcacgtga tcggcatggg caccacccc gaggtgcaca gcatcttcct     60
      ggagggccac accttcctgg tgcgcaacca ccgccaggcc agcctggaga tcagccccat    120
      caccttcctg accgcccaga ccctgctgat ggacctgggc cagttcctgc tgttctgcca    180
      catcagcagc caccagcacg acggcatgga ggcctacgtg aaggtggaca gctgccccga    240
      ggagcccag ctgcgcatga agaacaacga ggaggccgag gactacgacg acgacctgac    300
      cgacagcgag atggacgtgg tgcgcttcga cgacgacaac agccccagct tcatccagat    360
      ctctacggat cctacaagct ttac                                          384

<210> SEQ ID NO 109
<211> LENGTH: 443
<212> TYPE: DNA
<213> ORGANISM: Artificial Sequence
<220> FEATURE:
<223> OTHER INFORMATION: synthetically generated construct

<400> SEQUENCE: 109
gtagaattcg tagggatccg cagcgtggcc aagaagcacc ccaagacctg ggtgcactac     60
      atcgccgccg aggaggagga ctgggactac gcccccctgg tgctggcccc cgacgaccgc    120
      agctacaaga gccagtacct gaacaacggc cccagcgca tcggccgcaa gtacaagaag    180
      gtgcgcttca tggcctacac cgacgagacc ttcaagaccc gcgaggccat ccagcacgag    240
      agcggcatcc tgggcccct gctgtacggc gaggtgggcg acaccctgct gatcatcttc    300
      aagaaccagg ccagccgccc ctacaacatc taccccccacg gcatcaccga cgtgcgcccc    360
      ctgtacagcc gccgcctgcc caagggcgtg aagcacctga aggacttccc catcctgccc    420
      ggcgagatct ctacaagctt tac                                           443

<210> SEQ ID NO 110
<211> LENGTH: 266
<212> TYPE: DNA
<213> ORGANISM: Artificial Sequence
<220> FEATURE:
<223> OTHER INFORMATION: synthetically generated construct
```

<400> SEQUENCE: 110

```
     gtaaagcttg tagggtacca gctgcggttc tcgtcgaaca cgctgaacag gatcacgttg      60
     cgcttgtcgc tcatgatctg gttgccgcgc tggtccacgc tctccttgta gcagatcagc     120
     aggggggccga tcaggccgct ggccaggtcg cgctccatgt tcacgaagct gctgtagtag     180
     cgggtcaggc agcggggtc gctcttggtg gggccgtcct ccacggtcac ggtccacttg       240
     tacttgaaga tctctacgaa ttctac                                           266
```

<210> SEQ ID NO 111
<211> LENGTH: 341
<212> TYPE: DNA
<213> ORGANISM: Artificial Sequence
<220> FEATURE:
<223> OTHER INFORMATION: synthetically generated construct

<400> SEQUENCE: 111

```
     gtagaattcg tagggtacct gaccgagaac atccagcgct tcctgcccaa cccgccggc       60
     gtgcagctgg aggaccccga gttccaggcc agcaacatca tgcacagcat caacggctac    120
     gtgttcgaca gcctgcagct gagcgtgtgc ctgcacgagg tggcctactg gtacatcctg    180
     agcatcggcg cccagaccga cttcctgagc gtgttcttca gcggctacac cttcaagcac    240
     aagatggtgt acgaggacac cctgaccctg ttccccttca gcggcgagac cgtgttcatg    300
     agcatggaga accccggcct gtggatccct acaagcttta c                        341
```

<210> SEQ ID NO 112
<211> LENGTH: 397
<212> TYPE: DNA
<213> ORGANISM: Artificial Sequence
<220> FEATURE:
<223> OTHER INFORMATION: synthetically generated construct

<400> SEQUENCE: 112

```
     gtagaattcg tagggatcct gggctgccac aacagcgact tccgcaaccg cggcatgacc      60
     gccctgctga aggtgagcag ctgcgacaag aacaccggcg actactacga ggacagctac    120
     gaggacatca gcgcctacct gctgagcaag aacaacgcca tcgagccccg cctggaggag    180
     atcaccccgca ccaccctgca gagcgaccgg aggagatcg actacgacga ccaccatcagc   240
     gtggagatga agaaggagga cttcgacatc tacgacgagg acgagaacca gagcccccgc    300
     agcttccaga agaagacccg ccactacttc atcgccgcg tggagcgcct gtgggactac     360
     ggcatgagca gcagccccca cgtgctacaa gctttac                              397
```

<210> SEQ ID NO 113
<211> LENGTH: 417
<212> TYPE: DNA
<213> ORGANISM: Artificial Sequence
<220> FEATURE:
<223> OTHER INFORMATION: synthetically generated construct

<400> SEQUENCE: 113

```
     gtagaattcg tagcacgtgc tgcgcaaccg cgcccagagc ggcagcgtgc cccagttcaa       60
     gaaggtggtg ttccaggagt tcaccgacgg cagcttcacc cagcccctgt accgcggcga    120
     gctgaacgag cacctgggcc tgctgggccc ctacatccgc gccgaggtgg aggacaacat    180
     catggtgacc gtgcaggagt tcgccctgtt cttccaccatc ttcgacgaga ccaagagctg    240
     gtacttcacc gagaacatgg agcgcaactg ccgcgccccc tgcaacatcc agatggagga    300
     ccccaccttc aaggagaact accgcttcca cgccatcaac ggctacatca tggacaccct    360
     gccccggcctg gtgatggccc aggaccagcg catccgctgg tacccctacaa gctttac     417
```

<210> SEQ ID NO 114
<211> LENGTH: 327
<212> TYPE: DNA
<213> ORGANISM: Artificial Sequence
<220> FEATURE:
<223> OTHER INFORMATION: synthetically generated construct

<400> SEQUENCE: 114

```
     gtagaattcg tagggtgacc ttccgcaacc aggccagccg ccctacagc ttctacagca        60
     gcctgatcag ctacgaggag gaccagcgcc agggcgccga gccccgcaag aacttcgtga    120
     agcccaacga gaccaagacc tactctggga aggtgcagca ccacatggcc cccaccaagg    180
     acgagttcga ctgcaaggcc tgggcctact tcagcgacgt ggacctggag aaggacgtgc    240
     acagcggcct gatcggcccc ctgctggtgt gccacaccaa caccctgaac ccgcccacg    300
     gccgccaggt gaccctacaa gctttac                                         327
```

```
<210> SEQ ID NO 115
<211> LENGTH: 344
<212> TYPE: DNA
<213> ORGANISM: Artificial Sequence
<220> FEATURE:
<223> OTHER INFORMATION: synthetically generated construct

<400> SEQUENCE: 115
gtagaattcg tagggtacct gctgagcatg ggcagcaacg agaacatcca cagcatccac      60
    ttcagcggcc acgtgttcac cgtgcgcaag aaggaggagt acaagatggc cctgtacaac     120
    ctgtaccccg cgtgttcga ccgtggag atgctgccca gcaaggccgc catctggcgc        180
    gtggagtgcc tgatcggcga gcacctgcac gccggcatga gcaccctgtt cctggtgtac     240
    agcaacaagt gccagacccc cctgggcatg gccagcggcc acatccgcga cttccagatc     300
    accgccagcg gccagtacgg ccagtgggcc cctacaagct ttac                      344

<210> SEQ ID NO 116
<211> LENGTH: 322
<212> TYPE: DNA
<213> ORGANISM: Artificial Sequence
<220> FEATURE:
<223> OTHER INFORMATION: synthetically generated construct

<400> SEQUENCE: 116
gtagaattcg taggggcccc caagctggcc cgcctgcact acagcggcag catcaacgcc      60
    tggagcacca aggagcccctt cagctggatc aaggtgacc tgctggcccc catgatcatc     120
    cacggcatca agacccaggg cgcccgccag aagttcagca gcctgtacat cagccagttc     180
    atcatcatgt acagcctgga cggcaagaag tggcagacct accgcggcaa cagcaccggc     240
    acctgatgg tgttcttcgg caacgtggac agcagcggca tcaagcacaa catcttcaac      300
    cccccgggc tacaagcttt ac                                               322

<210> SEQ ID NO 117
<211> LENGTH: 323
<212> TYPE: DNA
<213> ORGANISM: Artificial Sequence
<220> FEATURE:
<223> OTHER INFORMATION: synthetically generated construct

<400> SEQUENCE: 117
gtagaattcg taggatatca tcgcccgcta catccgcctg caccccaccc actacagcat      60
    ccgcagcacc ctgcgcatgg agctgatggg ctgcgacctg aacagctgca gcatgcccct    120
    gggcatggag agcaaggcca tcagcgacgc ccagatcacc gccagcagct acttcaccaa    180
    catgttcgcc acctggagcc ccagcaaggc ccgcctgcac ctgcagggcc gcagcaacgc    240
    ctggcgcccc caggtgaaca accccaagga gtggctgcag gtggacttcc agaagaccat    300
    gaaggtgacc ctacaagctt tac                                            323

<210> SEQ ID NO 118
<211> LENGTH: 318
<212> TYPE: DNA
<213> ORGANISM: Artificial Sequence
<220> FEATURE:
<223> OTHER INFORMATION: synthetically generated construct

<400> SEQUENCE: 118
gtagaattcg tagggtgacc ggcgtgacca cccagggcgt gaagagcctg ctgaccagca      60
    tgtacgtgaa ggagttcctg atcagcagca gccaggacgg ccaccagtgg accctgttct    120
    tccagaacgg caaggtgaag gtgttccagg gcaaccagga cagcttcacc cccgtggtga    180
    acagcctgga ccccccctg ctgacccgct acctgcgcat ccaccccag agctgggtgc      240
    accagatcgc cctgcgcatg gaggtgctgg gctgcgaggc ccaggacctg tactagctgc    300
    ccgggctaca agctttac                                                  318

<210> SEQ ID NO 119
<211> LENGTH: 310
<212> TYPE: DNA
<213> ORGANISM: Artificial Sequence
<220> FEATURE:
<223> OTHER INFORMATION: synthetically generated construct

<400> SEQUENCE: 119
gtaaagcttg taggggccca gcaggcccat ccagggggg cggggcttgg cgatgttgaa      60
```

```
caggtggtcg gtgaactcca cgaacagggt cttccttgtac accacgctgg tgttgaaggg    120
gaagctcttg ggcacgcggg gggggaagcg ggcgtccacg ggcagctcgc ccaggtcgct    180
ctgcatgtag tcccagctca gctccacggc gcccaggtag tagcggcggg tggcgctgaa    240
gcagaagcgc agcaggcaca ggaagaagca ggtgctcagc tcgatctgca tgctagccta    300
cgaattctac                                                          310
```

<210> SEQ ID NO 120
<211> LENGTH: 297
<212> TYPE: DNA
<213> ORGANISM: Artificial Sequence
<220> FEATURE:
<223> OTHER INFORMATION: synthetically generated construct

<400> SEQUENCE: 120

```
gtaaagcttg tagcacgtgg ctcaggtagc tgtaggtcag gcacaggggg tcgctggcca     60
tggggccgtt ctccttcagc acctgccaca cgtaggtgtg gctgccgccg gggaacacct    120
tgtcgtcctc cttctcgcgc tggctggtct ggtcgtcgta ctcggcgccc tcgctggcct    180
tccagtagct cacgcccacg gcgtgcaggc tcacgggtg gctggccatg ttcttcaggg     240
tgatcaccac ggtgtcgtac acctcggcct ggatggtggg gcccctacga attctac       297
```

<210> SEQ ID NO 121
<211> LENGTH: 318
<212> TYPE: DNA
<213> ORGANISM: Artificial Sequence
<220> FEATURE:
<223> OTHER INFORMATION: synthetically generated construct

<400> SEQUENCE: 121

```
gtaaagcttg tagcacgtgc cagtacacgc tcttgcggtg cagccgatc aggccgggca      60
ggctgcggtt cacgtagccg ttcacggtgt gcatcttggg ccaggcgcgc gcgctggcgg    120
cgtcgcggtc ctgcatcagg ctgttcttgg tctcgctgtg ccagctcttg ccctcgtcga    180
acacgcgaa cagcaggatg aacttgtgca gggtctgggt cttctccttg gccaggctgc     240
cctcgcggca caccagcagg gcgccgatca ggccgctgtt caggtccttc accaggtcca    300
cgtggctacg aattctac                                                  318
```

<210> SEQ ID NO 122
<211> LENGTH: 384
<212> TYPE: DNA
<213> ORGANISM: Artificial Sequence
<220> FEATURE:
<223> OTHER INFORMATION: synthetically generated construct

<400> SEQUENCE: 122

```
gtaaagcttg taggatccgt agagatctgg atgaagctgg ggctgttgtc gtcgtcgaag     60
cgcaccacgt ccatctcgct gtcggtcagg tcgtcgtcgt agtcctcggc ctcctcgttg    120
ttcttcatgc gcagctgggg ctcctcgggg cagctgtcca ccttcacgta ggcctccatg    180
ccgtcgtgct ggtggctgct gatgtgcag aacagcagga actgcccag gtccatcagc      240
agggtctggg cggtcaggaa ggtgatgggg ctgatctcca ggctggcctg gcggtggttg    300
cgcaccagga aggtgtggcc ctccaggaag atgctgtgca cctcgggggt ggtgcccatg    360
ccgatcacgt gctacgaatt ctac                                           384
```

<210> SEQ ID NO 123
<211> LENGTH: 443
<212> TYPE: DNA
<213> ORGANISM: Artificial Sequence
<220> FEATURE:
<223> OTHER INFORMATION: synthetically generated construct

<400> SEQUENCE: 123

```
gtaaagcttg tagagatctc gccgggcagg atgggaagt ccttcaggtg cttcacgccc      60
ttgggcaggc ggcggctgta caggggggcgc acgtcggtga tgccgtgggg gtagatgttg    120
taggggcggc tggcctggtt cttgaagatg atcagcaggg tgtcgcccac ctcgccgtac    180
agcagggggc ccaggatgcc gctctcgtgc tggatggcct cgcgggtctt gaaggtctcg    240
tcggtgtagg ccatgaagcg caccttcttg tacttgcggc cgatgcgctg ggggccgttg    300
ttcaggtact ggctcttgta gctgcggtcg tcggggccg gcaccagggg ggcgtagtcc      360
cagtcctcct cctcggcggc gatgtagtgc acccaggtct ggggtgctt cttggccacg     420
ctgcggatcc ctacgaattc tac                                            443
```

<210> SEQ ID NO 124
<211> LENGTH: 266

```
<212> TYPE: DNA
<213> ORGANISM: Artificial Sequence
<220> FEATURE:
<223> OTHER INFORMATION: synthetically generated construct

<400> SEQUENCE: 124
gtagaattcg tagagatctt caagtacaag tggaccgtga ccgtggagga cggccccacc      60
     aagagcgacc cccgctgcct gacccgctac tacagcagct tcgtgaacat ggagcgcgac     120
     ctggccagcg gcctgatcgg ccccctgctg atctgctaca aggagagcgt ggaccagcgc     180
     ggcaaccaga tcatgagcga caagcgcaac gtgatcctgt tcagcgtgtt cgacgagaac     240
     cgcagctggt accctacaag ctttac                                          266

<210> SEQ ID NO 125
<211> LENGTH: 341
<212> TYPE: DNA
<213> ORGANISM: Artificial Sequence
<220> FEATURE:
<223> OTHER INFORMATION: synthetically generated construct

<400> SEQUENCE: 125
gtaaagcttg tagggatcca caggccgggg ttctccatgc tcatgaacac ggtctcgccg      60
     ctgaagggga acagggtcag ggtgtcctcg tacaccatct tgtgcttgaa ggtgtagccg     120
     ctgaagaaca cgctcaggaa gtcggtctgg gcgccgatgc tcaggatgta ccagtaggcc     180
     acctcgtgca ggcacacgct cagctgcagg ctgtcgaaca cgtagccgtt gatgctgtgc     240
     atgatgttgc tggcctggaa ctcggggtcc tccagctgca cgccggcggg gttgggcagg     300
     aagcgctgga tgttctcggt caggtaccct acgaattcta c                         341

<210> SEQ ID NO 126
<211> LENGTH: 397
<212> TYPE: DNA
<213> ORGANISM: Artificial Sequence
<220> FEATURE:
<223> OTHER INFORMATION: synthetically generated construct

<400> SEQUENCE: 126
gtaaagcttg tagcacgtgg gggctgctgc tcatgccgta gtcccacagg cgctccacgg      60
     cggcgatgaa gtagtggcgg gtcttcttct ggaagctgcg ggggctctgg ttctcgtcct     120
     cgtcgtagat gtcgaagtcc tccttcttca tctccacgct gatggtgtcg tcgtagtcga     180
     tctcctcctg gtcgctctgc agggtggtgc gggtgatctc ctccaggcgg ggctcgatgg     240
     cgttgttctt gctcagcagg taggcgctga tgtcctcgta gctgtcctcg tagtagtcgc     300
     cggtgttctt gtcgcagctg ctcaccttca gcagggcggt catgccgcgg ttgcggaagt     360
     cgctgttgtg gcagcccagg atccctacga attctac                              397

<210> SEQ ID NO 127
<211> LENGTH: 417
<212> TYPE: DNA
<213> ORGANISM: Artificial Sequence
<220> FEATURE:
<223> OTHER INFORMATION: synthetically generated construct

<400> SEQUENCE: 127
gtaaagcttg tagggtacca gcggatgcgc tggtcctggg ccatcaccag gccgggcagg      60
     gtgtccatga tgtagccgtt gatggcgtgg aagcggtagt tctccttgaa ggtggggtcc     120
     tccatctgga tgttgcaggg ggcgcgcag ttgcgctcca tgttctcggt gaagtaccag     180
     ctcttggtct cgtcgaagat ggtgaagaac agggcgaact cctgcacggt caccatgatg     240
     ttgtcctcca cctcggcgcg gatgtagggg cccagcaggc ccaggtgctc gttcagctcg     300
     ccgcggtaca ggggctgggt gaagctgccg tcggtgaact cctggaacac caccttcttg     360
     aactggggca cgctgccgct ctgggcgcgg ttgcgcagca cgtgctacga attctac        417

<210> SEQ ID NO 128
<211> LENGTH: 327
<212> TYPE: DNA
<213> ORGANISM: Artificial Sequence
<220> FEATURE:
<223> OTHER INFORMATION: synthetically generated construct

<400> SEQUENCE: 128
gtaaagcttg tagggtcacc tggcggccgt gggcggggtt cagggtgttg gtgtggcaca      60
     ccagcagggg gccgatcagg ccgctgtgca cgtccttctc caggtccacg tcgctgaagt     120
     aggcccaggc cttgcagtcg aactcgtcct tggtggggc catgtggtgc tgcaccttcc     180
```

```
agaagtaggt cttggtctcg ttgggcttca cgaagttctt gcggggctcg gcgccctggc      240
gctggtcctc ctcgtagctg atcaggctgc tgtagaagct gtaggggcgg ctggcctggt      300
tgcggaaggt caccctacga attctac                                          327
```

<210> SEQ ID NO 129
<211> LENGTH: 344
<212> TYPE: DNA
<213> ORGANISM: Artificial Sequence
<220> FEATURE:
<223> OTHER INFORMATION: synthetically generated construct

<400> SEQUENCE: 129

```
gtaaagcttg taggggccca ctggccgtac tggccgctgg cggtgatctg gaagtcgcgg      60
atgtggccgc tggccatgcc caggggggtc tggcacttgt tgctgtacac caggaacagg      120
gtgctccatgc cggcgtgcag gtgctcgccg atcaggcact ccacgcgcca gatgccggcc    180
ttgctgggca gcatctccac ggtctcgaac acgccggggt acaggttgta cagggccatc     240
ttgtactcct ccttcttgcg cacggtgaac acgtggccgc tgaagtggat gctgtggatg    300
ttctcgttgc tgcccatgct cagcaggtac cctacgaatt ctac                     344
```

<210> SEQ ID NO 130
<211> LENGTH: 322
<212> TYPE: DNA
<213> ORGANISM: Artificial Sequence
<220> FEATURE:
<223> OTHER INFORMATION: synthetically generated construct

<400> SEQUENCE: 130

```
gtaaagcttg tagcccgggg gggttgaaga tgttgtgctt gatgccgctg ctgtccacgt      60
tgccgaagaa caccatcagg gtgccggtgc tgttgccgcg gtaggtctgc cacttcttgc     120
cgtccaggct gtacatgatg atgaactggc tgatgtacag gctgctgaac ttctggcggg    180
cgccctgggt cttgatgccg tggatgatca tggggccag caggtccacc ttgatccagc     240
tgaagggctc cttggtgctc caggcgttga tgctgccgct gtagtgcagg cgggccagct    300
tgggggcccc tacgaattct ac                                              322
```

<210> SEQ ID NO 131
<211> LENGTH: 323
<212> TYPE: DNA
<213> ORGANISM: Artificial Sequence
<220> FEATURE:
<223> OTHER INFORMATION: synthetically generated construct

<400> SEQUENCE: 131

```
gtaaagcttg tagggtcacc ttcatggtct tctggaagtc cacctgcagc cactccttgg     60
ggttgttcac ctgggggcgc caggcgttgc tgcggccctg caggtgcggc caggccttgc    120
tggggctcca ggtggcgaac atgttggtga agtagctgct ggcggtgatc tgggcgtcgc    180
tgatggcctt gctctccatg cccaggggca tgctgcagct gttcaggtcg cagcccatca    240
gctccatgcg cagggtgctg cggatgctgt agtgggtggg gtgcaggcgg atgtagcggg    300
cgatgatatc ctacgaattc tac                                             323
```

<210> SEQ ID NO 132
<211> LENGTH: 318
<212> TYPE: DNA
<213> ORGANISM: Artificial Sequence
<220> FEATURE:
<223> OTHER INFORMATION: synthetically generated construct

<400> SEQUENCE: 132

```
gtaaagcttg tagcccgggc agctagtaca ggtcctgggc ctcgcagccc agcacctcca      60
tgcgcagggc gatctggtgc acccagctct gggggtggat gcgcaggtag cgggtcagca    120
gggggggggtc caggctgttc accacggggg tgaagctgtc ctggttgccc tggaacacct   180
tcaccttgcc gttctggaag aacagggtcc actggtggcc gtcctggctg ctgctgatca    240
ggaactcctt cacgtacatg ctggtcagca ggctcttcac gccctgggtg gtcacgccgg    300
tcaccctacg aattctac                                                   318
```

<210> SEQ ID NO 133
<211> LENGTH: 255
<212> TYPE: DNA
<213> ORGANISM: Artificial Sequence
<220> FEATURE:
<223> OTHER INFORMATION: synthetically generated construct

<400> SEQUENCE: 133

```
gtagaattcg gatcctgggc tgccacaaca gcgacttccg caaccgcggc atgaccgccc      60
tgctgaaggt gagcagctgc gacaagaaca ccggcgacta ctacgaggac agctacgagg    120
acatcagcgc ctacctgctg agcaagaaca acgccatcga gccccgcagg cgcaggcgcg    180
agatcacccg caccaccctg cagagcgacc aggaggagat cgactacgac gacaccatca    240
gcgtggaagc tttac                                                      255
```

<210> SEQ ID NO 134
<211> LENGTH: 255
<212> TYPE: DNA
<213> ORGANISM: Artificial Sequence
<220> FEATURE:
<223> OTHER INFORMATION: synthetically generated construct

<400> SEQUENCE: 134

```
gtaaagcttc cacgctgatg gtgtcgtcgt agtcgatctc ctcctggtcg ctctgcaggg      60
tggtgcgggt gatctcgcgc ctgcgcctgc ggggctcgat ggcgttgttc ttgctcagca    120
ggtaggcgct gatgtcctcg tagctgtcct cgtagtagtc gccggtgttc ttgtcgcagc    180
tgctcacctt cagcagggcg gtcatgccgc ggttgcggaa gtcgctgttg tggcagccca    240
ggatccgaat tctac                                                      255
```

<210> SEQ ID NO 135
<211> LENGTH: 4
<212> TYPE: PRT
<213> ORGANISM: Homo sapiens

<400> SEQUENCE: 135

```
Arg Arg Arg Arg
  1
```

<210> SEQ ID NO 136
<211> LENGTH: 5
<212> TYPE: PRT
<213> ORGANISM: Homo sapiens

<400> SEQUENCE: 136

```
Arg Arg Arg Arg Arg
  1               5
```